(12) United States Patent
Elmore et al.

(10) Patent No.: US 7,585,858 B2
(45) Date of Patent: Sep. 8, 2009

(54) N-SULFONYLCARBOXIMIDAMIDE APOPTOSIS PROMOTERS

(75) Inventors: Steven W. Elmore, Gurnee, IL (US); Milan Bruncko, Green Oaks, IL (US); Cheol-Min Park, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 388 days.

(21) Appl. No.: 11/138,717

(22) Filed: May 26, 2005

(65) Prior Publication Data

US 2005/0272744 A1 Dec. 8, 2005

Related U.S. Application Data

(60) Provisional application No. 60/574,500, filed on May 26, 2004.

(51) Int. Cl.
| | |
|---|---|
| *A61K 31/5377* | (2006.01) |
| *A61K 31/451* | (2006.01) |
| *C07D 211/14* | (2006.01) |
| *C07D 211/48* | (2006.01) |
| *C07D 211/70* | (2006.01) |
| *C07D 413/12* | (2006.01) |
| *A61K 31/495* | (2006.01) |
| *C07D 295/195* | (2006.01) |

(52) U.S. Cl. .................. 514/235.5; 514/326; 514/331; 514/255.01; 514/235.8; 544/129; 544/121; 544/392; 544/398; 546/213; 546/216; 546/231

(58) Field of Classification Search ........................ None
See application file for complete search history.

(56) References Cited

U.S. PATENT DOCUMENTS

2002/0086887 A1 7/2002 Augeri et al.

FOREIGN PATENT DOCUMENTS

| WO | 03/080586 | 1/2003 |
| WO | 03080586 A1 | 10/2003 |

OTHER PUBLICATIONS

Khorchid et al. Expert Opin. Ther. Patents vol. 14, p. 805-818 (2004).*
Petros, A.M., et al., "Solution structure of the antiapoptotic protein bcl-2", *PNAS*, 98(6):3012-3017 (2001).
Sattler, M., et al., "Structure of Bcl-xL-Bak Peptide Complex: Recognition Between Regulators of Apoptosis", *Science*, 275:983-986 (1997).
U.S. Appl. No. 09/957,265, filed Sep. 20, 2001.
U.S. Appl. No. 10/269,739, filed Oct. 14, 2002.

* cited by examiner

*Primary Examiner*—Emily Bernhardt
(74) *Attorney, Agent, or Firm*—Patricia Coleman James

(57) ABSTRACT

Compounds having the formula

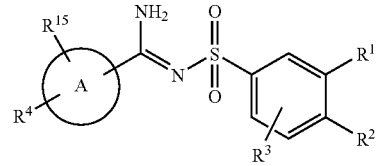

are apoptosis promoters. Also disclosed are methods of making the compounds, compositions containing the compounds, and methods of treatment using the compounds.

4 Claims, No Drawings

N-SULFONYLCARBOXIMIDAMIDE APOPTOSIS PROMOTERS

This application claims benefit to provisional application No. 60/574,500, filed May 26, 2004.

TECHNICAL FIELD

The present invention relates to substituted N-sulfonylcarboximidamides which are useful for promoting apoptosis, methods of making the compounds, compositions containing the compounds, and methods of treatment using the compounds.

BACKGROUND OF THE INVENTION

Apoptosis is a mode of cell death in which the cell commits suicide either to ensure proper development of the organism or to destroy cells that represent a threat to the organism's integrity. Morphologically, apoptosis is characterized by blebbing of the plasma membrane, shrinking of the cytoplasm and nucleus, and fragmenting into particles which are engulfed by phagocytic cells. Although apoptosis plays a critical role in normal development, its impairment is thought to be a significant factor in the etiology of such diseases as cancer, autoimmune disorders, inflammatory diseases, and viral infections. Conversely, increased apoptosis has been linked to AIDS and neurodegenerative diseases such as Parkinson's disease, stroke, and Alzheimer's disease.

Bcl-$X_L$ is a protein which, in healthy cells, is expressed in the outer membranes of the mitochondria, the endoplasmic reticulum, and the nuclear envelope. Its function is to bind to specific protein/protease complexes and prevent cell apoptosis. Upon internal damage to the cell the protein/protease complexes are released, and cause the process of apoptosis to begin. An over-expression of Bcl-$X_L$, often present in cancerous and other diseased cells, results in the blocking of apoptotic signals and allows the cells to proliferate. It is believed that by blocking Bcl-$X_L$, apoptosis can be induced in diseased cells, and can provide an effective therapy for cancer and other diseases caused by the impairment of the apoptotic process. Based on these findings and the absence of small molecule Bcl-$X_L$ inhibitors from current cancer therapies, there is a continuing need for compounds which can trigger apoptosis through the inhibition of the Bcl family of proteins.

SUMMARY OF THE INVENTION

In its principle embodiment the present invention provides a compound of formula (I)

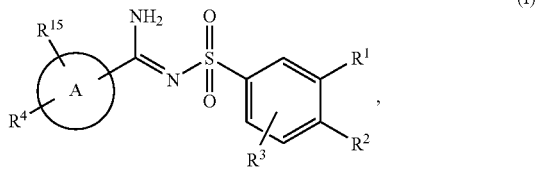

(I)

or a therapeutically acceptable salt thereof, wherein

A is a five-, six-, or seven-membered aromatic or non-aromatic ring wherein from zero to three carbon atoms are replaced by a heteroatom selected from the group consisting of nitrogen, oxygen, and sulfur;

$R^1$ is selected from the group consisting of alkyl, cyano, halo, haloalkyl, nitro, and —$NR^5R^6$;

$R^2$, and $R^3$ are independently selected from the group consisting of hydrogen, alkenyl, alkoxy, alkyl, alkylcarbonyloxy, alkylsulfanyl, alkynyl, aryl, arylalkoxy, aryloxy, aryloxyalkoxy, arylsulfanyl, arylsulfanylalkoxy, cycloalkylalkoxy, cycloalkyloxy, halo, haloalkoxy, haloalkyl, heterocyclyl, heterocyclyloxy, hydroxy, nitro, and —$NR^5R^6$;

$R^4$ is selected from the group consisting of aryl, arylalkenyl, arylalkoxy, cycloalkenyl, cycloalkyl, heterocyclyl, and heterocyclylalkoxy;

$R^5$ and $R^6$ are independently selected from the group consisting of hydrogen, alkenyl, alkoxyalkyl, alkoxycarbonylalkyl, alkyl, alkylsulfanylalkyl, alkylsulfonylalkyl, aryl, arylalkyl, arylalkylsulfanylalkyl, aryloxyalkyl, arylsulfanylalkyl, arylsulfinylalkyl, arylsulfonylalkyl, carboxyalkyl, cycloalkenyl, cycloalkenylalkyl, cycloalkyl, (cycloalkyl)alkyl, cycloalkylcarbonyl, heterocyclyl, heterocyclylalkyl, heterocyclylsulfanylalkyl, hydroxyalkyl, and a nitrogen protecting group; or $R^5$ and $R^6$, together with the nitrogen atom to which they are attached, form a ring selected from the group consisting of imidazolyl, morpholinyl, piperazinyl, piperidinyl, pyrrolidinyl, pyrrolyl, thiomorpholinyl, and thiomorpholinyl dioxide; and $R^{15}$ is selected from the group consisting of hydrogen, alkoxy, alkyl, and halo.

In a preferred embodiment the present invention provides a compound of formula (I) where $R^3$ and $R^{15}$ are hydrogen.

In another preferred embodiment the present invention provides a compound of formula (I) where $R^3$ and $R^{15}$ are hydrogen and $R^2$ is —$NR^5R^6$.

In another preferred embodiment the present invention provides a compound of formula (I) where $R^3$ and $R^{15}$ are hydrogen, $R^2$ is —$NR^5R^6$, one of $R^5$ and $R^6$ is hydrogen and the other is arylsulfanylalkyl.

In another preferred embodiment the present invention provides a compound of formula (I) where $R^3$ and $R^{15}$ are hydrogen, $R^2$ is —$NR^5R^6$, one of $R^5$ and $R^6$ is hydrogen and the other is arylsulfanylalkyl, and A is piperazinyl.

Examples of compounds supporting this embodiment are
4-(4-benzyl-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide;

N-((4-(((1R)-3-(dimethylamino)-1-((phenylsulfanyl)methyl)propyl)amino)-3-nitrophenyl)sulfonyl)-4-phenyl-1-piperazinecarboximidamide;

N-((4-(((1R)-3-(dimethylamino)-1-((phenylsulfanyl)methyl)propyl)amino)-3-nitrophenyl)sulfonyl)-4-(4-methoxy-4-(2-methylbenzyl)cyclohexyl)-1-piperazinecarboximidamide;

4-(4-(2-chlorobenzyl)-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide;

N-((4-(((1R)-3-(dimethylamino)-1-((phenylsulfanyl)methyl)propyl)amino)-3-nitrophenyl)sulfonyl)-4-(4-(2-fluorobenzyl)-4-methoxycyclohexyl)-1-piperazinecarboximidamide; and 4-(4-(2-bromobenzyl)-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide.

In another preferred embodiment the present invention provides a compound of formula (I) where $R^3$ and $R^{15}$ are hydrogen, $R^2$ is —$NR^5R^6$, one of $R^5$ and $R^6$ is hydrogen and the other is arylsulfanylalkyl, and A is phenyl.

In another preferred embodiment the present invention provides a compound of formula (I) where $R^3$ and $R^{15}$ are hydrogen, $R^2$ is —$NR^5R^6$, one of $R^5$ and $R^6$ is hydrogen and the other is arylsulfanylalkyl, A is phenyl, and $R^4$ is piperidinyl.

EXAMPLEs of compounds supporting this embodiment are

N-((4-(((1R)-3-(dimethylamino)-1-((phenylsulfanyl)methyl)propyl)amino)-3-nitrophenyl)sulfonyl)-4-(4-(2-fluorobenzyl)-4-methoxy-1-piperidinyl)benzenecarboximidamide;

N-((4-(((1R)-3-(dimethylamino)-1-((phenylsulfanyl)methyl)propyl)amino)-3-nitrophenyl)sulfonyl)-4-(4,4-dimethyl-1-piperidinyl)benzenecarboximidamide;

N-((4-(((1R)-5-(dimethylamino)-1-((phenylsulfanyl)methyl)pentyl)amino)-3-nitrophenyl)sulfonyl)-4-(4,4-dimethyl-1-piperidinyl)benzenecarboximidamide;

4-(4,4-dimethyl-1-piperidinyl)-N-((3-nitro-4-((2-(phenylsulfanyl)ethyl)amino)phenyl)sulfonyl)benzenecarboximidamide;

4-(4-benzyl-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide;

4-(4-(cyclohexylmethyl)-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide;

4-(4-(2,4-difluorobenzyl)-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide;

N-((4-(((1R)-3-(dimethylamino)-1-((phenylsulfanyl)methyl)propyl)amino)-3-nitrophenyl)sulfonyl)-4-(4-methoxy-4-(2-methylbenzyl)-1-piperidinyl)benzenecarboximidamide;

N-((4-(((1R)-3-(dimethylamino)-1-((phenylsulfanyl)methyl)propyl)amino)-3-nitrophenyl)sulfonyl)-4-(4-(4-fluorobenzylidene)-1-piperidinyl)benzenecarboximidamide;

N-((4-(((1R)-3-(dimethylamino)-1-((phenylsulfanyl)methyl)propyl)amino)-3-nitrophenyl)sulfonyl)-4-(4-(2-(trifluoromethyl)benzylidene)-1-piperidinyl)benzenecarboximidamide;

N-((4-(((1R)-3-(dimethylamino)-1-((phenylsulfanyl)methyl)propyl)amino)-3-nitrophenyl)sulfonyl)-4-(4-(3-thienylmethylene)-1-piperidinyl)benzenecarboximidamide;

4-(4-methoxy-4-(2-methylbenzyl)-1-piperidinyl)-N-((3-nitro-4-((2-(phenylsulfanyl)ethyl)amino)phenyl)sulfonyl)benzenecarboximidamide;

N-((4-((1,1-dimethyl-2-(phenylsulfanyl)ethyl)amino)-3-nitrophenyl)sulfonyl)-4-(4-methoxy-4-(2-methylbenzyl)-1-piperidinyl)benzenecarboximidamide;

4-(4-methoxy-4-(2-methylbenzyl)-1-piperidinyl)-N-((4-(((1R)-3-(4-morpholinyl)-1-((phenylsulfanyl)methyl)propyl)amino)-3-nitrophenyl)sulfonyl)benzenecarboximidamide;

4-(4-(1,1'-biphenyl-2-ylmethyl)-4-methoxy-1-piperidinyl)-N-((3-nitro-4-((2-(phenylsulfanyl)ethyl)amino)phenyl)sulfonyl)benzenecarboximidamide;

4-(4-(1,1'-biphenyl-2-ylmethyl)-4-methoxy-1-piperidinyl)-N-((4-((1,1-dimethyl-2-(phenylsulfanyl)ethyl)amino)-3-nitrophenyl)sulfonyl)benzenecarboximidamide;

4-(4-(1,1'-biphenyl-2-ylmethyl)-4-methoxy-1-piperidinyl)-N-((4-(((1R)-3-(4-morpholinyl)-1-((phenylsulfanyl)methyl)propyl)amino)-3-nitrophenyl)sulfonyl)benzenecarboximidamide;

4-(4-(1,1'-biphenyl-2-ylmethylene)-1-piperidinyl)-N'-((3-nitro-4-((2-(phenylsulfanyl)ethyl)amino)phenyl)sulfonyl)benzenecarboximidamide;

4-(4-(1,1'-biphenyl-2-ylmethylene)-1-piperidinyl)-N'-((4-((1,1-dimethyl-2-(phenylsulfanyl)ethyl)amino)-3-nitrophenyl)sulfonyl)benzenecarboximidamide;

4-(4-(1,1'-biphenyl-2-ylmethylene)-1-piperidinyl)-N'-((4-(((1R)-3-(4-morpholinyl)-1-((phenylsulfanyl)methyl)propyl)amino)-3-nitrophenyl)sulfonyl)benzenecarboximidamide;

N'-((3-nitro-4-((2-(phenylsulfanyl)ethyl)amino)phenyl)sulfonyl)-4-(4-(2-(trifluoromethyl)benzylidene)-1-piperidinyl)benzenecarboximidamide;

N'-((4-((1,1-dimethyl-2-(phenylsulfanyl)ethyl)amino)-3-nitrophenyl)sulfonyl)-4-(4-(2-(trifluoromethyl)benzylidene)-1-piperidinyl)benzenecarboximidamide; and N'-((4-(((1R)-3-(4-morpholinyl)-1-((phenylsulfanyl)methyl)propyl)amino)-3-nitrophenyl)sulfonyl)-4-(4-(2-(trifluoromethyl)benzylidene)-1-piperidinyl)benzenecarboximidamide.

In another preferred embodiment the present invention provides a compound of formula (I) where $R^3$ and $R^{15}$ are hydrogen, $R^2$ is —$NR^5R^6$, one of $R^5$ and $R^6$ is hydrogen and the other is arylsulfanylalkyl, A is phenyl, and $R^4$ is piperazinyl.

EXAMPLEs of compounds supporting this embodiment are

N-((4-(((1R)-3-(dimethylamino)-1-((phenylsulfanyl)methyl)propyl)amino)-3-nitrophenyl)sulfonyl)-4-(4-(3,3-diphenyl-2-propenyl)-1-piperazinyl)benzenecarboximidamide;

4-(4-((4'-chloro-1,1'-biphenyl-2-yl)methyl)-1-piperazinyl)-N-((3-nitro-4-((2-(phenylsulfanyl)ethyl)amino)phenyl)sulfonyl)benzenecarboximidamide;

4-(4-((4'-chloro-1,1'-biphenyl-2-yl)methyl)-1-piperazinyl)-N-((4-((1,1-dimethyl-2-(phenylsulfanyl)ethyl)amino)-3-nitrophenyl)sulfonyl)benzenecarboximidamide;

4-(4-((4'-chloro-1,1'-biphenyl-2-yl)methyl)-1-piperazinyl)-N-((4-(((1R)-3-(4-morpholinyl)-1-((phenylsulfanyl)methyl)propyl)amino)-3-nitrophenyl)sulfonyl)benzenecarboximidamide;

4-(4-(3,3-diphenyl-2-propenyl)-1-piperazinyl)-N'-((3-nitro-4-((2-(phenylsulfanyl)ethyl)amino)phenyl)sulfonyl)benzenecarboximidamide;

N'-((4-((1,1-dimethyl-2-(phenylsulfanyl)ethyl)amino)-3-nitrophenyl)sulfonyl)-4-(4-(3,3-diphenyl-2-propenyl)-1-piperazinyl)benzenecarboximidamide; and 4-(4-(3,3-diphenyl-2-propenyl)-1-piperazinyl)-N'-((4-(((1R)-3-(4-morpholinyl)-1-((phenylsulfanyl)methyl)propyl)amino)-3-nitrophenyl)sulfonyl)benzenecarboximidamide.

In another embodiment, the present invention discloses a pharmaceutical composition comprising a compound of formula (I), or a therapeutically acceptable salt thereof, in combination with a therapeutically acceptable carrier.

In another embodiment, the present invention discloses a method of promoting apoptosis in a mammal in recognized need of such treatment comprising administering to the mammal a therapeutically acceptable amount of a compound of formula (I), or a therapeutically acceptable salt thereof.

DETAILED DESCRIPTION OF THE INVENTION

Compounds of the present invention comprise substituted N-sulfonylcarboximidamides which are useful for the treatment of apoptosis-mediated diseases.

All patents, patent applications, and literature references cited in the specification are herein incorporated by reference in their entirety. In the case of inconsistencies, the present disclosure, including definitions, will prevail.

As used in the present specification the following terms have the meanings indicated:

The term "alkenyl," as used herein, refers to a straight or branched chain group of one to twelve carbon atoms derived from a straight or branched chain hydrocarbon containing at least one carbon-carbon double bond.

The term "alkenylene," as used herein, refers to a group of two to six atoms derived from an unsaturated straight or branched chain hydrocarbon.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxyalkyl," as used herein, refers to an alkyl group substituted with one, two, or three alkoxyalkoxy groups.

The term "alkoxyalkoxycarbonyl," as used herein, refers to an alkoxyalkoxy group attached to the parent molecular moiety through a carbonyl group.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group of one to twelve carbon atoms derived from a straight or branched chain saturated hydrocarbon.

The term "alkylcarbonyl," as used herein, refers to an alkyl group attached to the parent molecular moiety through a carbonyl group. The alkylcarbonyl groups of this invention can be optionally substituted with one or two groups independently selected from the group consisting of hydroxy and —$NR^5R^6$, wherein $R^5$ and $R^6$ are as previously defined.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylene," as used herein, refers to a group of two to six atoms derived from a saturated straight or branched chain hydrocarbon.

The term "alkylidene," as used herein, refers to an alkenyl group in which one carbon atom of the carbon-carbon double bond belongs to the moiety to which the alkenyl group is attached.

The term "alkylsulfanyl," as used herein, refers to an alkyl group attached to the parent molecular moiety through a sulfur atom.

The term "alkylsulfanylalkyl," as used herein, refers to an alkyl group substituted with one, two, or three alkylsulfanyl groups.

The term "alkylsulfonyl," as used herein, refers to an alkyl group attached to the parent molecular moiety through a sulfonyl group.

The term "alkylsulfonylalkyl," as used herein, refers to an alkyl group substituted with one, two, or three alkylsulfonyl groups.

The term "alkynyl," as used herein, refers to a straight or branched chain group of one to twelve carbon atoms containing at least one carbon-carbon triple bond.

The term "aryl," as used herein, refers to a phenyl group, or a bicyclic or tricyclic fused ring system wherein one or more of the rings is a phenyl group. Bicyclic fused ring systems consist of a phenyl group fused to a monocyclic cycloalkenyl group, a monocyclic cycloalkyl group, or another phenyl group. Tricyclic fused ring systems consist of a bicyclic fused ring system fused to a monocyclic cycloalkenyl group, a monocyclic cycloalkyl group, or another phenyl group. The aryl groups of the present invention can be attached to the parent molecular moiety through any substitutable carbon atom in the group. Representative EXAMPLEs of aryl groups include, but are not limited to, anthracenyl, azulenyl, fluorenyl, indanyl, indenyl, naphthyl, phenyl, and tetrahydronaphthyl. Preferred aryl groups of the present invention include phenyl. The aryl groups of the present invention can be optionally substituted with one, two, three, four, or five substituents independently selected from the group consisting of alkenyl, alkoxy, alkoxyalkyl, alkoxyalkylcarbonyl, alkoxycarbonyl, alkoxycarbonylalkyl, alkyl, alkylcarbonyl, alkylcarbonyloxy, alkynyl, a second aryl group, arylalkoxy, aryloxy, arylsulfanyl, cyano, halo, haloalkoxy, haloalkyl, heterocyclyl, heterocyclylalkyl, heterocyclylcarbonylalkenyl, heterocyclylcarbonylalkyl, hydroxy, hydroxyalkyl, nitro, —$NR^aR^b$, ($NR^aR^b$)alkyl, ($NR^aR^b$)carbonyl, ($NR^aR^b$)carbonylalkyl, ($NR^aR^b$)sulfonyl, oxo, and —$C(NH)NH_2$, wherein the second aryl group; the aryl part of the arylalkoxy, the aryloxy, and the arylsulfanyl; the heterocyclyl; and the heterocyclyl part of the heterocyclylalkyl, the heterocyclylcarbonylalkenyl, and the heterocyclylcarbonylalkyl can be further optionally substituted with one, two, or three substituents independently selected from the group consisting of alkoxyalkylcarbonyl, alkoxycarbonyl, alkyl, alkylsulfonyl, cyano, halo, haloalkoxy, haloalkyl, hydroxy, nitro, ($NR^aR^b$)carbonyl, ($NR^aR^b$)sulfonyl, oxo, and —$C(NH)NH_2$. In addition, the heterocyclyl and the heterocyclyl part of the heterocyclylalkyl, the heterocyclylcarbonylalkenyl, and the heterocyclylcarbonylalkyl can be further optionally substituted with an additional aryl group, wherein the additional aryl group can be optionally substituted with one, two, or three substituents independently selected from the group consisting of alkoxy, alkyl, cyano, halo, hydroxy, and nitro.

The term "arylalkenyl," as used herein, refers to an alkenyl group substituted by one, two, or three aryl groups.

The term "arylalkoxy," as used herein, refers to an arylalkyl group attached to the parent molecular moiety through an oxygen atom.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl can be optionally substituted with one or two —$NR^aR^b$ groups.

The term "arylalkylcarbonyl," as used herein, refers to an arylalkyl group attached to the parent molecular moiety through a carbonyl group.

The term "arylalkylidene," as used herein, refers to an aryl group attached to the parent molecular moiety through an alkylidene group.

The term "arylalkylsulfanyl," as used herein, refers to an arylalkyl group attached to the parent molecular moiety through a sulfur atom.

The term "arylalkylsulfanylalkyl," as used herein, refers to an alkyl group substituted with one, two, or three arylalkylsulfanyl groups.

The term "arylalkylsulfonyl," as used herein, refers to an arylalkyl group attached to the parent molecular moiety through a sulfonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkoxy," as used herein, refers to an aryloxy group attached to the parent molecular moiety through an alkoxy group.

The term "aryloxyalkyl," as used herein, refers to an alkyl group substituted with one, two, or three aryloxy groups.

The term "aryloxyalkylcarbonyl," as used herein, refers to an aryloxyalkyl group attached to the parent molecular moiety through a carbonyl group.

The term "arylsulfanyl," as used herein, refers to an aryl group attached to the parent molecular moiety through a sulfur atom.

The term "arylsulfanylalkoxy," as used herein, refers to an arylsulfanyl group attached to the parent molecular moiety through an alkoxy group. The alkoxy part of the arylsulfanylalkoxy can be optionally substituted with one or two —$NR^aR^b$ groups.

The term "arylsulfanylalkyl," as used herein, refers to an alkyl group substituted with one, two, or three arylsulfanyl group. The alkyl part of the arylsulfanylalkyl can be further optionally substituted with one or two substituents independently selected from the group consisting of alkoxy, alkoxycarbonyl, arylalkoxy, azido, carboxy, cycloalkyl, halo, heterocyclyl, heterocyclylalkoxy, heterocyclylcarbonyl, hydroxy, —$NR^aR^b$, ($NR^aR^b$)alkoxy, and ($NR^aR^b$)carbonyl.

The term "arylsulfinyl," as used herein, refers to an aryl group attached to the parent molecular moiety through a sulfinyl group.

The term "arylsulfinylalkyl," as used herein, refers to an alkyl group substituted with one, two, or three arylsulfinyl groups. The alkyl part of the arylsulfinylalkyl can be further optionally substituted with one or two —$NR^aR^b$ groups.

The term "arylsulfonyl," as used herein, refers to an aryl group attached to the parent molecular moiety through a sulfonyl group.

The term "arylsulfonylalkyl," as used herein, refers to an alkyl group substituted with one, two, or three arylsulfonyl groups. The alkyl part of the arylsulfonylalkyl can be further optionally substituted with one or two —$NR^aR^b$ groups.

The term "azido," as used herein, refers to —$N_3$.

The term "carbonyl," as used herein, refers to —C(O)—.

The term "carboxy," as used herein, refers to —$CO_2H$.

The term "carboxyalkyl," as used herein, refers to an alkyl group substituted with one, two, or three carboxy groups.

The term "cyano," as used herein, refers to —CN.

The term "cyanoalkyl," as used herein, refers to an alkyl group substituted with one, two, or three cyano groups.

The term "cycloalkenyl," as used herein, refers to a non-aromatic, partially unsaturated monocyclic, bicyclic, or tricyclic ring system having three to fourteen carbon atoms and zero heteroatoms. Representative EXAMPLEs of cycloalkenyl groups include, but are not limited to, cyclohexenyl, octahydronaphthalenyl, and norbornylenyl. The cycloalkenyl groups of this invention can be optionally substituted with one, two, three, four, or five substituents independently selected from the group consisting of alkoxy, alkoxycarbonyl, alkyl, arylalkoxy, aryloxy, arylsulfanyl, halo, haloalkoxy, haloalkyl, hydroxy, and ($NR^aR^b$)alkyl, wherein the aryl part of the arylalkoxy, the aryloxy, the arylsulfanyl, and the arylsulfanylalkyl can be further optionally substituted with one, two, or three substituents independently selected from the group consisting of alkoxy, alkyl, halo, haloalkoxy, haloalkyl, and hydroxy.

The term "cycloalkenylalkyl," as used herein, refers to an alkyl group substituted with one, two, or three cycloalkenyl groups.

The term "cycloalkyl," as used herein, refers to a saturated monocyclic, bicyclic, or tricyclic hydrocarbon ring system having three to fourteen carbon atoms and zero heteroatoms. Representative EXAMPLEs of cycloalkyl groups include, but are not limited to, cyclopropyl, cyclopentyl, bicyclo (3.1.1)heptyl, and adamantyl. The cycloalkyl groups of this invention can be optionally substituted with one, two, three, four, or five substituents independently selected from the group consisting of alkoxy, alkoxycarbonyl, alkyl, alkylidene, aryl, arylalkenyl, arylalkoxy, arylalkyl, arylalkylidene, aryloxy, arylsulfanyl, arylsulfanylalkyl, a second cycloalkyl group, (cycloalkyl)alkyl, cycloalkylalkylidene, halo, haloalkoxy, haloalkyl, heterocyclyl, heterocyclylalkoxy, heterocyclylalkyl, heterocyclylalkylidene, hydroxy, —$NR^aR^b$, ($NR^aR^b$)alkoxy, ($NR^aR^b$)alkyl, spirocyclyl, and spiroheterocyclyl; wherein the aryl; the aryl part of the arylalkenyl, the arylalkoxy, the arylalkyl, the arylalkylidene, the aryloxy, the arylsulfanyl, and the arylsulfanylalkyl; the second cycloalkyl group, the cycloalkyl part of the (cycloalkyl) alkyl and the cycloalkylalkylidene; the heterocyclyl; and the heterocyclyl part of the heterocyclylalkoxy, the heterocyclylalkyl, and the heterocyclylalkylidene can be further optionally substituted with one, two, or three substituents independently selected from the group consisting of alkoxy, alkyl, unsubstituted aryl, cyano, halo, haloalkoxy, haloalkyl, and hydroxy.

The term "cycloalkylalkoxy," as used herein, refers to a cycloalkyl group attached to the parent molecular moiety through an alkoxy group.

The term "(cycloalkyl)alkyl," as used herein, refers to an alkyl group substituted with one, two, or three cycloalkyl groups.

The term "cycloalkylalkylidene," as used herein, refers to a cycloalkyl group attached to the parent molecular moiety through an alkylidene group.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "dialkylamino," as used herein, refers to —$N(R^{14})_2$, wherein $R^{14}$ is alkyl.

The term "dialkylaminoalkyl," as used herein, refers to an alkyl group substituted with one, two, or three dialkylamino groups.

The term "dialkylaminocarbonyl," as used herein, refers to an dialkylamino group attached to the parent molecular moiety through a carbonyl group.

The term "dialkylaminocarbonylalkyl," as used herein, refers to an alkyl group substituted with one, two, or three dialkylaminocarbonyl groups.

The term "formyl," as used herein, refers to —CHO.

The term "formylalkyl," as used herein, refers to an alkyl group substituted with one, two, or three formyl groups.

The term "halo," as used herein, refers to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylcarbonyl," as used herein, refers to a haloalkyl group attached to the parent molecular moiety through a carbonyl group.

The term "heteroalkenylene," as used herein, refers to an unsaturated group of two to six atoms containing one or two heteroatoms independently selected from the group consisting of nitrogen, oxygen, and sulfur, wherein the remaining atoms are carbon. The heteroalkylene groups of the present invention can be attached to the parent molecular moiety through the carbon atoms or the heteroatoms in the chain.

The term "heteroalkylene," as used herein, refers to a saturated group of two to six atoms containing one or two heteroatoms independently selected from the group consisting of nitrogen, oxygen, and sulfur, wherein the remaining atoms are carbon. The heteroalkylene groups of the present invention can be attached to the parent molecular moiety through the carbon atoms or the heteroatoms in the chain.

The term "heterocyclyl," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group; and tricyclic groups in which a bicyclic system is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. EXAMPLEs of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present invention can be optionally substituted with one, two, three, four, or five substituents independently selected from the group consisting of alkenyl, alkoxy, alkoxyalkoxycarbonyl, alkoxyalkyl, alkoxycarbonyl, alkoxycarbonylalkyl, alkyl, alkylcarbonyl, alkylcarbonylalkyl, alkylcarbonyloxy, alkylsulfanylalkyl, alkynyl, aryl, arylalkenyl, arylalkoxyalkyl, arylalkoxyalkylcarbonyl, arylalkoxycarbonyl, arylalkyl, arylalkylcarbonyl, arylalkylidene, arylalkylsulfonyl, arylcarbonyl, aryloxy, aryloxyalkylcarbonyl, arylsulfanyl, arylsulfanylalkyl, arylsulfonyl, carboxy, cyano, cyanoalkyl, cycloalkyl, (cycloalkyl)alkyl, cycloalkylcarbonyl, formyl, formylalkyl, halo, haloalkoxy, haloalkyl, a second heterocyclyl group, heterocyclylalkenyl, heterocyclylalkyl, heterocyclylalkylcarbonyl, heterocyclylalkylidene, heterocyclylcarbonyl, heterocyclylcarbonylalkyl, hydroxy, hydroxyalkyl, nitro, —$NR^aR^b$, ($NR^aR^b$)alkyl, ($NR^aR^b$)alkylcarbonyl, ($NR^aR^b$)carbonyl, ($NR^aR^b$)carbonylalkyl, ($NR^aR^b$)sulfonyl, oxo, spirocyclyl, spiroheterocyclyl, and —C(NH)NH$_2$; wherein the aryl; the aryl part of the arylalkenyl, the arylalkoxyalkyl, the arylalkoxyalkylcarbonyl, the arylalkoxycarbonyl, the arylalkyl, the arylalkylcarbonyl, the arylalkylidene, the arylalkylsulfonyl, the arylcarbonyl, the aryloxy, the aryloxyalkylcarbonyl, the arylsulfanyl, the arylsulfanylalkyl, and the arylsulfonyl; the heterocyclyl; and the heterocycyl part of the heterocyclylalkenyl, the heterocyclylalkyl, the heterocyclylalkylcarbonyl, the heterocyclylalkylidene, the heterocyclylcarbonyl, and the heterocyclylcarbonylalkyl can be further optionally substituted with one, two, three, four, or five substituents independently selected from the group consisting of alkoxy, alkoxyalkoxycarbonyl, alkoxycarbonyl, alkyl, alkylcarbonyl, an additional aryl group, cyano, halo, haloalkoxy, haloalkyl, hydroxy, hydroxyalkyl, and nitro, wherein the additional aryl group can be further optionally substituted with one, two, three, four, or five substituents independently selected from the group consisting of alkoxy, alkyl, cyano, halo, haloalkoxy, haloalkyl, and nitro. In addition, the alkenyl part of the heterocyclylalkenyl can be further optionally substituted with one or two unsubstituted aryl groups.

The term "heterocyclylalkenyl," as used herein, refers to an alkenyl group substituted by one, two, or three heterocyclyl groups. The alkenyl part of the heterocyclylalkenyl can be optionally substituted with one or two aryl groups.

The term "heterocyclylalkoxy," as used herein, refers to a heterocyclyl group attached to the parent molecular moiety through an alkoxy group.

The term "heterocyclylalkyl," as used herein, refers to an alkyl group substituted with one, two, or three heterocyclyl groups.

The term "heterocyclylalkylcarbonyl," as used herein, refers to a heterocyclylalkyl group attached to the parent molecular moiety through a carbonyl group.

The term "heterocyclylalkylidene," as used herein, refers to a heterocyclyl group attached to the parent molecular moiety through an alkylidene group.

The term "heterocyclylcarbonyl," as used herein, refers to a heterocyclyl group attached to the parent molecular moiety through a carbonyl group.

The term "heterocyclylcarbonylalkenyl," as used herein, refers to an alkenyl group substituted with one, two, or three heterocyclylcarbonyl groups.

The term "heterocyclylcarbonylalkyl," as used herein, refers to an alkyl group substituted with one, two, or three heterocyclylcarbonyl groups.

The term "heterocyclyloxy," as used herein, refers to a heterocyclyl group attached to the parent molecular moiety through an oxygen atom.

The term "heterocyclylsulfanyl," as used herein, refers to a heterocyclyl group attached to the parent molecular moiety through a sulfur atom.

The term "heterocyclylsulfanylalkyl," as used herein, refers to an alkyl group substituted with one, two, or three heterocyclylsulfanyl groups.

The term "hydroxy," as used herein, refers to —OH.

The term "hydroxyalkyl," as used herein, refers to an alkyl group substituted with one, two, or three hydroxy groups.

The term "nitro," as used herein, refers to —NO$_2$.

The term "nitrogen protecting group," as used herein, refers to groups intended to protect an amino group against undesirable reactions during synthetic procedures. Common N-protecting groups comprise acyl groups such as acetyl, benzoyl, 2-bromoacetyl, 4-bromobenzoyl, tert-butylacetyl, carboxaldehyde, 2-chloroacetyl, 4-chlorobenzoyl, a-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate forming groups such as benzyloxycarbonyl, benzyloxycarbonyl (Cbz), tert-butyloxycarbonyl (Boc), p-chlorobenzyloxycarbonyl, p-methoxybenzyloxycarbonyl, and the like.

The term "—$NR^aR^b$," as used herein, refers to two groups, $R^a$ and $R^b$, which are attached to the parent molecular moiety through a nitrogen atom. $R^a$ and $R^b$ are independently selected from the group consisting of hydrogen, alkenyl, alkoxyalkyl, alkoxyalkoxyalkyl, alkoxycarbonyl, alkyl, alkylcarbonyl, aryl, arylalkoxycarbonyl, arylalkyl, arylalkylcarbonyl, arylcarbonyl, arylsulfonyl, cycloalkyl, (cycloalkyl)alkyl, cycloalkylcarbonyl, dialkylaminoalkyl, dialkylaminocarbonylalkyl, haloalkyl, haloalkylcarbonyl, heterocyclyl, heterocyclylalkyl, heterocyclylcarbonyl, hydroxyalkyl, a nitrogen protecting group, —C(NH)$NH_2$, and —C(O)$(CH_2)_n NR^5R^6$, wherein n is 0, 1, 2, or 3; and $R^5$ and $R^6$ are as previously defined; wherein the aryl; the aryl part of the arylalkoxycarbonyl, the arylalkyl, the arylalkylcarbonyl, the arylcarbonyl, and the arylsulfonyl; the cycloalkyl; the cycloalkyl part of the (cycloalkyl)alkyl and the cycloalkylcarbonyl; the heterocyclyl; and the heterocycyl part of the heterocyclylalkyl and the heterocyclylcarbonyl can be optionally substituted with one, two, three, four, or five substituents independently selected from the group consisting of alkoxy, alkyl, alkylcarbonyl, cyano, halo, haloalkoxy, haloalkyl, hydroxy, and nitro.

The term "($NR^aR^b$)alkoxy," as used herein, refers to an ($NR^aR^b$)alkyl group attached to the parent molecular moiety through an oxygen atom.

The term "($NR^aR^b$)alkyl," as used herein, refers to an alkyl group substituted with one, two, or three —$NR^aR^b$ groups.

The term "($NR^aR^b$)alkylcarbonyl," as used herein, refers to an —$NR^aR^b$ group attached to the parent molecular moiety through an alkylcarbonyl group.

The term "($NR^aR^b$)carbonyl," as used herein, refers to an —$NR^aR^b$ group attached to the parent molecular moiety through a carbonyl group.

The term "($NR^aR^b$)carbonylalkyl," as used herein, refers to an alkyl group substituted with one, two, or three ($NR^aR^b$) carbonyl groups.

The term "($NR^aR^b$)sulfonyl," as used herein, refers to an —$NR^aR^b$ group attached to the parent molecular moiety through a sulfonyl group.

The term "oxo," as used herein, refers to (=O).

The term "spirocyclyl," as used herein, refers to an alkenylene or alkylene group in which both ends of the alkenylene or alkylene group are attached to the same carbon of the parent molecular moiety to form a bicyclic group. The spirocyclyl groups of the present invention can be optionally substituted with one substituent selected from the group consisting of alkyl, aryl, arylalkoxyalkyl, arylalkyl, and aryloxyalkyl.

The term "spiroheterocyclyl," as used herein, refers to a heteroalkenylene or heteroalkylene group in which both ends of the heteroalkenylene or heteroalkylene group are attached to the same carbon of the parent molecular moiety to form a bicyclic group. The spiroheterocyclyl groups of the present invention can be optionally substituted with one substituent selected from the group consisting of alkyl, aryl, arylalkoxyalkyl, arylalkyl, and aryloxyalkyl.

The term "sulfinyl," as used herein, refers to —S(O)—.

The term "sulfonyl," as used herein, refers to —$SO_2$—.

The term "therapeutically acceptable salt," as use herein, refers to those salts which are, within the scope of sound medical judgment, suitable for use in contact with the tissues of humans and lower animals without undue toxicity, irritation, allergic response and the like and are commensurate with a reasonable benefit/risk ratio. The salts can be prepared in situ during the final isolation and purification of the compounds of the present invention or separately by reacting a free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include calcium, lithium, magnesium, potassium, sodium, and the like, as well as non-toxic ammonium, quaternary ammonium, and amine cations, including, but not limited to, ammonium, dimethylamine, ethylamine, methylamine, tetraethylammonium, tetramethylammonium, triethylamine, trimethylamine, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to induce apoptosis. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

According to methods of treatment, the compounds of the present invention can be useful for the prevention of metastases from the tumors described above either when used alone or in combination with radiotherapy and/or other chemotherapeutic treatments conventionally administered to patients for treating cancer. When using the compounds of the present invention for chemotherapy, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. For example, when used in the treatment of solid tumors, compounds of the present invention can be administered with chemotherapeutic agents such as alpha inteferon, COMP (cyclophosphamide, vincristine, methotrexate, and prednisone), etoposide, mBACOD (methortrexate, bleomycin, doxorubicin, cyclophosphamide, vincristine, and dexamethasone), PRO-MACE/MOPP (prednisone, methotrexate (w/leucovin rescue), doxorubicin, cyclophosphamide, taxol, etoposide/mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. For example, a tumor may be treated conventionally with surgery, radiation or chemotherapy and a compound of the present invention subsequently administered to extend the dormancy of micrometastases and to stabilize and inhibit the growth of any residual primary tumor.

The compounds of the present invention can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds of the present invention can be formulated with dispersing, wetting, or suspending agents. The injectable preparation can also be an injectable solution or suspension in a diluent or solvent. Among the acceptable diluents or solvents employed are water, saline, Ringer's solution, buffers, dilute acids or bases, dilute amino acid solutions, monoglycerides, diglycerides, fatty acids such as oleic acid, and fixed oils such as monoglycerides or diglycerides.

The chemotherapeutic effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents; and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes thereof.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds of the present invention with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of the present invention.

The total daily dose of the compounds of the present invention administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

Assays for the inhibition of Bcl-$X_L$ were performed in 96-well microtiter plates. Compounds of the present invention were diluted in DMSO to concentrations between 100 µM and 1 pM and introduced into each cell of the plate. A mixture totaling 125 µL per well of assay buffer (20 mM phosphate buffer (pH 7.4), 1 mM EDTA, 0.05% PEG-8000), 50 nM of BCL-$X_L$ protein (prepared according to the procedure described in Science 1997, 275, 983-986), 5 nM fluorescein-labeled BAD peptide (purchased from Synpep, CA), and the DMSO solution of the compound of the present invention was shaken for 2 minutes and placed in a LJL Analyst (LJL Bio Systems, CA). A negative control (DMSO, 5 nM BAD peptide, assay buffer) and a positive control (DMSO, 5 nM BAD peptide, 50 nM BCL-$X_L$, assay buffer) were used to determine the range of the assay. Polarization was measured at room temperature using a continuous Fluorescein lamp (excitation 485 mM, emission 530 mM). Percentage of inhibition was determined by (1−((mP value of well-negative control)/range))×100%. $IC_{50}$ values were calculated using Microsoft Excel. Compounds of the present invention have $IC_{50}$ values between about 0.010 and about 10 μM and are therefore useful for inhibiting BCL-$X_L$ and treating apoptosis-mediated diseases. Preferred compounds of the present invention have $IC_{50}$ values between about 0.010 μM and about 0.05 μM.

Assays for the inhibition of Bcl-2 were performed in 96-well microtiter plates. Compounds of the instant invention were diluted in DMSO to concentrations between 100 μM and 1 pM and introduced into each well of the plate. A mixture totaling 125 μL per well of assay buffer (20 mM phosphate buffer (pH 7.4), 1 mM EDTA, 0.05% PF-68), 30 nM of Bcl-2 protein (prepared according to the procedure described in PNAS 2001, 98, 3012-3017), 5 nM fluorescein-labeled BAX peptide (prepared in-house), and the DMSO solution of the compound of the instant invention was shaken for 2 minutes and placed in a LJL Analyst (LJL Bio Systems, CA). A negative control (DMSO, 5 nM BAX peptide, assay buffer) and a positive control (DMSO, 5 nM BAX peptide, 30 nM Bcl-2, assay buffer) were used to determine the range of the assay. Polarization was measured at room temperature using a continuous Fluorescein lamp (excitation 485 mM, emission 530 mM). Percentage of inhibition was determined by (1−((mP value of well-negative control)/range))×100%. $IC_{50}$ values were calculated using Microsoft Excel. Compounds of the present invention have $IC_{50}$ values between about 0.001 and about 10 μM and are therefore useful for inhibiting Bcl-2 and treating apoptosis-mediated diseases.

Based upon the structural and functional similarity of the Bcl antiapoptotic proteins, it is reasonable to expect that in addition to inducing apoptosis by the inhibition of Bcl-$X_L$ and Bcl-2, the current invention may induce apoptosis through their action on other antiapoptotic proteins in the Bcl family of proteins, such as Bcl-w, Bcl-b, MCL-1 and/or A1/Bfl-1.

Synthetic Methods

Abbreviations which have been used in the descriptions of the scheme and the examples that follow are: THF for tetrahydrofuran; DMSO for dimethylsulfoxide; HMPA for hexamethylphosphoramide; DMF for N,N-dimethylformamide; nBuLi for n-butyllithium; LiHMDS for lithium hexamethyldisilazide; DME for 1,2-dimethoxyethane; $PPh_3$ for triphenylphosphine; and OAc for acetate.

The compounds and processes of the present invention will be better understood in connection with the following synthetic schemes which illustrate the methods by which the compounds of the invention may be prepared. Additional methods for the formation of the compounds of the present invention can be found in commonly owned WO03/080586. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. The groups $R^1$, $R^2$, $R^3$, $R^4$, and $R^{15}$ are as defined above unless otherwise noted below. It will be readily apparent to one skilled in the art that the selective protection and deprotections steps, as well as the order of the steps themselves, can be carried out in varying order, depending on the nature of $R^1$, $R^2$, $R^3$, $R^4$, $R^{15}$, $R^a$, $R^b$, and $R^c$, to successfully complete the syntheses shown below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

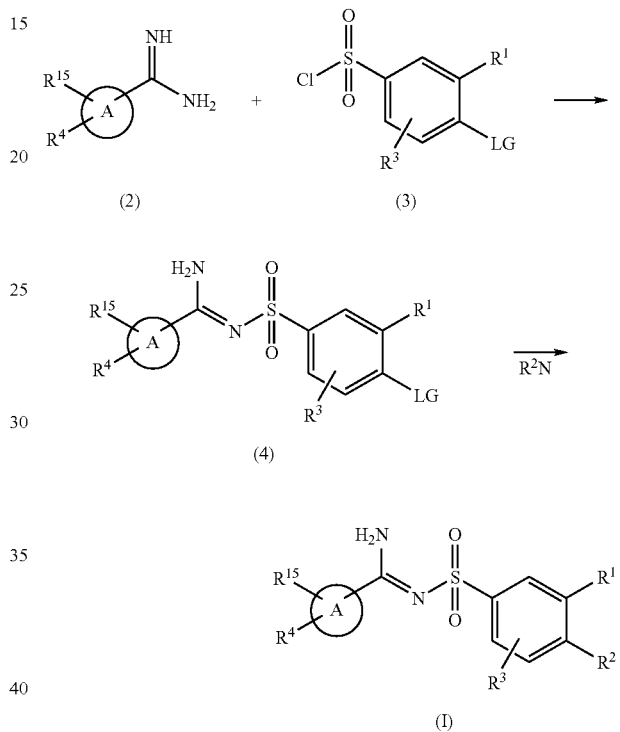

As shown in Scheme 1, compounds of formula (2) (which can be prepared according to the procedures described in Scheme 2 and examples listed below) can be reacted with compounds of formula (3) in which LG is an appropriate leaving group (which can be prepared by treatment of the appropriately substituted aromatic ring with chlorosulfonic acid) in the presence of a base such as triethylamine or diisopropylethylamine to provide compounds of formula (4) that can be reacted with a nucleophile, $R^2H$ to provide compounds of formula (I).

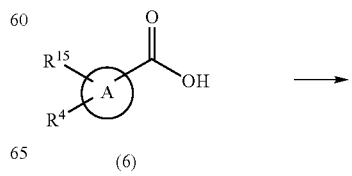

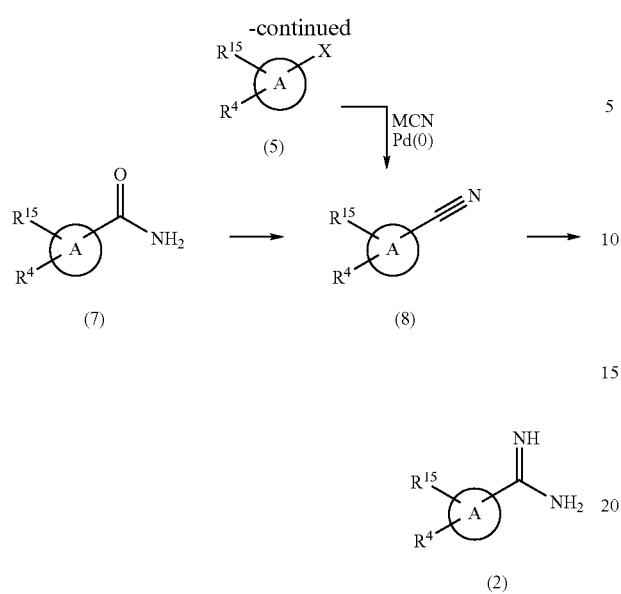

Scheme 2 shows the synthesis of compounds of formula (2). Compounds of formula (6) (which can be prepared according to procedures described in commonly owned U.S. patent application Ser. No. 09/957,256, filed Sep. 20, 2001, or by procedures described in commonly owned U.S. patent application Ser. No. 10/269,739, filed Oct. 14, 2002) can be treated with an activating agent such as thionyl chloride, oxalyl chloride or carbonyldiimidazole followed by aqueous ammonia to provide compounds of formula (7). Compounds of formula (7) can be treated with dehydrating agents such as oxalyl chloride or phosphorous oxychloride to provide nitriles of formula (8). Alternatively, compounds of formula (5) where X is bromine, iodine, or chlorine can be converted to compounds of formula (8) by treatment with an appropriate metallocyanide species in the presence of Pd(0). Nitriles of formula (8) can be converted to compounds of formula (2) by treatment with HCl in ethanol followed by ammonia, or by treatment with lithium hexamethyldisilazide followed by aqueous acid.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names which appeared to be consistent with ACD nomenclature.

EXAMPLE 1

N-((4-(((1R)-3-(dimethylamino)-1-((phenylsulfanyl)methyl)propyl)amino)-3-nitrophenyl)sulfonyl)-4-(4-(2-fluorobenzyl)-4-methoxy-1-piperidinyl)benzenecarboximidamide

EXAMPLE 1A 1-benzyl-4-(2-fluorobenzyl)-4-piperidinol

A suspension of Mg (3.50 g, 144 mmol) in diethyl ether (75 mL) was treated with 2-fluorobenzyl chloride (19.0 g, 131 mmol), stirred until all the Mg dissolved, treated with N-benzyl 4-piperidone (27.2 g, 144 mmol) in RATIO THF/diethyl ether (40 mL), and stirred at room temperature until the reaction was complete by TLC analysis. The mixture was partitioned between ethyl acetate and saturated $NH_4Cl$ and the aqueous layer was extracted with ethyl acetate twice. The combined organic layers were dried ($MgSO_4$), filtered, and concentrated to give a residue which was used without further purification. MS (ESI) m/e 300 $(M+H)^+$.

EXAMPLE 1B 4-(2-fluorobenzyl)-4-piperidinol

A solution of EXAMPLE 1A (39.0 g, 131 mmol) in ethyl acetate (500 mL) was treated with Pd/C (3.90 g), stirred under hydrogen atmosphere (60 psi) until the reaction was complete by TLC analysis, and filtered. The filtrate was concentrated to give a residue that was used without further purification. MS (ESI) m/e 210 $(M+H)^+$.

EXAMPLE 1C ethyl 4-(4-(2-fluorobenzyl)-4-hydroxy-1-piperidinyl)benzoate

A solution EXAMPLE 1B (13.75 g, 65.8 mmol) in DMSO (20 mL) was treated with ethyl 4-fluorobenzoate (8.50 g, 51.0 mmol) and $K_2CO_3$ (6.90 g, 50.0 mmol) and was heated to 110° C. overnight. The suspension was filtered and the filtrate diluted with ethyl acetate, washed with water (2×), dried ($MgSO_4$), and filtered. Concentration of the filtrate gave a residue that was purified by silica gel chromatography eluting with 30% ethyl acetate in hexanes to provide the desired product (17.89 g, 76%). MS (ESI) m/e 358 $(M+H)^+$.

EXAMPLE 1D ethyl 4-(4-(2-fluorobenzyl)-4-methoxy-1-piperidinyl)benzoate

A solution of EXAMPLE 1C (17.89 g, 50.1 mmol) in THF (150 mL) and HMPA (33 mL) was treated with NaH (4.0 g of a 60% dispersion, 100 mmol) at 0° C., stirred for 30 minutes, treated with $CH_3I$ (20 mL, 321 mmol), and stirred overnight. The reaction mixture was partitioned between ethyl acetate and saturated aqueous $NH_4Cl$. The organic layer was washed with water (2×), dried ($MgSO_4$), and filtered. Filtration of the concentrate provided the desired product which was used without further purification. MS (ESI) m/e 372 $(M+H)^+$.

EXAMPLE 1E 4-(4-(2-fluorobenzyl)-4-methoxy-1-piperidinyl)benzoic acid

A solution of EXAMPLE 1D (20.54 g, 55.4 mmol) in dioxane (100 mL) was treated with 1N NaOH (100 mL, 100 mmol), stirred overnight, acidified with 1N HCl, extracted with ethyl acetate (3×), dried (MgSO$_4$), and filtered. Concentration of the filtrate gave a residue that was purified by silica gel chromatography eluting with to provide the desired product (xx g, xx %). MS (ESI) m/e 344 (M+H)$^+$.

EXAMPLE 1F 4-(4-(2-fluorobenzyl)-4-methoxy-1-piperidinyl)benzamide

A solution of EXAMPLE 1E in dichloromethane (20 mL) was treated with oxalyl chloride (0.305 mL, 3.50 mmol) and a drop of DMF, stirred for 6 hours at room temperature, and concentrated. The resulting residue was dissolved in dichloromethane (20 mL), cooled to 0° C., treated with aqueous NH$_3$ (3 mL), stirred for 6 hours, and partitioned between ethyl acetate and saturated aqueous sodium chloride. The organic layer was separated and the aqueous layer was extracted with ethyl acetate three times. The combined organic layers were dried (MgSO$_4$) and filtered. Concentration of the filtrate gave the desired product as a residue that was utilized directly in the next step without further purification. MS

EXAMPLE 1G 4-(4-(2-fluorobenzyl)-4-methoxy-1-piperidinyl)benzonitrile

A solution of EXAMPLE 1F in acetonitrile (20 mL) at 0° C. was treated with DMF (0.543 mL, 7.02 mmol) and oxalyl chloride (0.561 mL, 6.43 mmol), stirred for 5 minutes, treated with pyridine (1.04 mL, 12.866 mmol), and stirred for another 50 minutes at 0° C. The reaction mixture was partitioned between ethyl acetate and saturated aqueous NaHCO$_3$, the aqueous layer extracted with ethyl acetate three times and the combined organic layers dried (MgSO$_4$), filtered, and concentrated to give the desired product as a residue that was utilized directly in the next step without further purification. MS (ESI) m/e 325 (M+H)$^+$.

EXAMPLE 1H 4-(4-(2-fluorobenzyl)-4-methoxy-1-piperidinyl)benzenecarboximidamide A solution of EXAMPLE 1G in ethanol (20 mL) at 0° C. was treated with gaseous HCl for 10 minutes, allowed to warm to ambient temperature, and stirred overnight. The reaction mixture was concentrated to dryness, the residue dissolved in methanol (20 mL), and the resulting solution treated with gaseous NH$_3$ for 10 minutes, stirred overnight, and concentrated to dryness. The resulting residue was purified by silica gel chromatography eluting with 10% 2N NH$_3$/methanol in dichloromethane to give the desired product. MS (ESI) m/e 342 (M+H)$^+$.

EXAMPLE 1I 4-(4-(2-fluorobenzyl)-4-methoxy-1-piperidinyl)-N-((4-fluoro-3-nitrophenyl)sulfonyl)benzenecarboximidamide A solution of EXAMPLE 1H (0.200 g, 0.587 mmol) in dichloromethane (5 mL) was treated with triethylamine (0.245 mL, 1.76 mmol) and 4-fluoro-3-nitrobenzenesulfonyl chloride (prepared according to the procedure described in U.S. patent applicaiton Ser. No. 09/957,256, 0.169 g, 0.704 mmol), stirred overnight, and concentrated. The residue was purified by silica gel chromatography eluting with 40% ethyl acetate in hexanes to provide the desired product. MS (ESI) m/e 543 (M+H)$^+$.

EXAMPLE 1J benzyl (1R)-3-(dimethylamino)-1-(hydroxymethyl)-3-oxopropylcarbamate A solution of 3-(S)-((carbobenzyloxy)amino)-γ-butyrolactone (prepared according to the procedure described in McGarvey, G. J.; Williams, J. M.; Hiner, R. N.; Matsubara, Y.; Oh, T. J. Am. Chem. Soc. 1986, 108, 4943-4952, 7.72 g, 32.8 mmol) in THF (100 mL) was saturated with gaseous dimethylamine, stirred at room temperature for 16 hours, and concentrated. The residue was filtered through a plug of silica gel eluting with 50% acetone in hexanes to give the desired product (9.16 g, 99%). MS (CI) m/e 281 (M+H)$^+$.

EXAMPLE 1K benzyl (1R)-3-(dimethylamino)-3-oxo-1-((phenylsulfanyl)methyl)propylcarbamate A solution of EXAMPLE 1J (8.45 g, 30.14 mmol) in toluene (15 mL) was treated with tributylphosphine (9.76 mL, 39.20 mmol), diphenyldisulfide (7.30 g, 39.20 mmol) and heated to 80° C. for 16 hours. The reaction mixture was concentrated and purified by column chromatography on silica gel eluting with a gradient of 0-50% ethyl acetate in hexanes to give the desired product (10.62 g, 95%). MS (CI) m/e 373 (M+H)$^+$.

EXAMPLE 1L (3R)-3-amino-N,N-dimethyl-4-(phenylsulfanyl)butanamide

A suspension of EXAMPLE 1K (10.60 g, 28.46 mmol) in 50 mL 30% HBr/acetic acid was stirred at room temperature overnight. The resulting homogeneous reaction mixture was concentrated, diluted with water (200 mL) and 5% HCl (100 mL), and washed with diethyl ether (3×). The aqueous phase was adjusted to pH ~8-9 with solid Na$_2$CO$_3$ and extracted with dichloromethane (5×). The combined organic phases were dried (MgSO$_4$), filtered, and concentrated to give the desired product (6.54 g, 96%). MS (CI) m/e 239 (M+H)$^+$.

EXAMPLE 1M

N-((3R)-3-amino-4-(phenylsulfanyl)butyl)-N,N-dimethylamine

A solution of EXAMPLE 1L (8.68 g, 36.5 mmol) in THF (200 mL) was treated with BH$_3$-dimethylsulfide (18.2 mL, 182.5 mmol) at room temperature, stirred overnight, treated slowly with methanol (20 mL), followed by 2N HCl (50 mL), stirred overnight, and concentrated. The resulting residue was purified by silica gel chromatography eluting with 5% 7N NH$_3$/CH$_3$OH in dichloromethane to give the desired product (4.50 g, 55%). MS (CI) m/e 224 (M+H)$^+$.

EXAMPLE 1N

N-((4-(((1R)-3-(dimethylamino)-1-((phenylsulfanyl)methyl)propyl)amino)-3-nitrophenyl)sulfonyl)-4-(4-(2-fluorobenzyl)-4-methoxy-1-piperidinyl)benzenecarboximidamide A solution of EXAMPLE 1I (0.072 g, 0.132 mmol) in 1:1 DMSO/diisopropylethylamine (2 mL) was treated with EXAMPLE 1M (0.044 g, 0.199 mmol) at room temperature, stirred overnight, and concentrated. The resulting residue was purified by silica gel chromatography eluting with 5% 2N NH$_3$/CH$_3$OH in dichloromethane to provide the desired product (0.072 g, 73%). MS (ESI) m/e 747 (M−H)$^-$; $^1$H NMR (400 MHz, DMSO-d$_6$) δ 8.74 (s, 1H), 8.58 (d, 1H), 8.39 (d, 1H), 7.95 (s, 1H), 7.73 (m, 3H), 7.20 (m, 3H), 7.12 (t, 2H), 7.06 (m, 3H), 6.98 (d, 1H), 6.87 (d, 2H), 4.05 (m, 1H), 3.58 (d, 2H), 3.29 (m, 4H), 3.22 (s, 3H), 2.92 (t, 2H), 2.75 (s, 2H), 2.34 (m, 1H), 2.15 (m, 1H), 2.05 (s, 6H), 1.88 (m, 1H), 1.75 (m, 1H), 1.65 (d, 2H), 1.44 (m, 2H).

EXAMPLE 2

N-((4-(((1R)-3-(dimethylamino)-1-((phenylsulfanyl)methyl)propyl)amino)-3-nitrophenyl)sulfonyl)-4-(4,4-dimethyl-1-piperidinyl)benzenecarboximidamide

EXAMPLE 2A 4-(4,4-dimethyl-1-piperidinyl)benzamide

The desired product was prepared by substituting 4-(4,4-dimethylpiperidin-1-yl)benzoic acid (prepared according to the procedure described in commonly owned U.S. patent application Ser. No. 09/957,256, filed Sep. 20, 2001) for EXAMPLE 1E in EXAMPLE 1F. MS

EXAMPLE 2B 4-(4,4-dimethyl-1-piperidinyl)benzonitrile

The desired product was prepared by substituting EXAMPLE 2A for EXAMPLE 1F in EXAMPLE 1G. MS (ESI) m/e 215 (M+H)$^+$.

EXAMPLE 2C 4-(4,4-dimethyl-1-piperidinyl)benzenecarboximidamide

The desired product was prepared by substituting EXAMPLE 2B for EXAMPLE 1G in EXAMPLE 1H. MS (ESI) m/e 232 (M+H)$^+$.

EXAMPLE 2D 4-(4,4-dimethyl-1-piperidinyl)-N-((4-fluoro-3-nitrophenyl)sulfonyl)benzenecarboximidamide The desired product was prepared by substituting EXAMPLE 2C for EXAMPLE 1H in EXAMPLE 1I. MS (ESI) m/e 435 (M+H)$^+$.

EXAMPLE 2E

N-((4-(((1R)-3-(dimethylamino)-1-((phenylsulfanyl)methyl)propyl)amino)-3-nitrophenyl)sulfonyl)-4-(4,4-dimethyl-1-piperidinyl)benzenecarboximidamide The desired product was prepared by substituting EXAMPLE 2D for EXAMPLE 1I in EXAMPLE 1N. MS (ESI) m/e 639 (M+H)$^+$; $^1$H NMR (400 MHz, DMSO-d$_6$) δ 8.76 (s, 1H), 8.60 (d, 1H), 8.43 (d, 1H), 7.98 (s, 1H), 7.78 (d, 2H), 7.28 (m, 2H), 7.14 (m, 3H), 7.04 (d, 1H), 6.93 (d, 2H), 4.11 (m, 1H), 3.35 (m, 6H), 2.40 (m, 1H), 2.24 (m, 1H), 2.12 (s, 6H), 1.94 (m, 1H), 1.80 (m, 1H), 1.38 (m, 4H), 0.95 (s, 6H).

EXAMPLE 3

N-((4-(((1R)-5-(dimethylamino)-1-((phenylsulfanyl)methyl)pentyl)amino)-3-nitrophenyl)sulfonyl)-4-(4,4-dimethyl-1-piperidinyl)benzenecarboximidamide

EXAMPLE 3A

N-((5R)-5-amino-6-(phenylsulfanyl)hexyl)-N,N-dimethylamine

The desired product was prepared by substituting (5R)-5-amino-N,N-dimethyl-6-(phenylsulfanyl)hexanamide for EXAMPLE 1L in EXAMPLE 1M. MS (ESI) m/e 253 (M+H)$^+$.

EXAMPLE 3B

N-((4-(((1R)-5-(dimethylamino)-1-((phenylsulfanyl)methyl)pentyl)amino)-3-nitrophenyl)sulfonyl)-4-(4,4-dimethyl-1-piperidinyl)benzenecarboximidamide The desired product was prepared by substituting EXAMPLE 3A and EXAMPLE 2D for EXAMPLE 1L and EXAMPLE 1I, respectively in EXAMPLE 1N. MS (ESI) m/e 667 (M+H)$^+$; $^1$H NMR (400 MHz, DMSO-d$_6$) δ 8.84 (s, 1H), 8.42 (d, 1H), 8.23 (d, 1H), 7.98 (s, 1H), 7.80 (d, 2H), 7.25 (m, 2H), 7.12 (m, 3H), 6.94 (d, 2H), 4.08 (m, 1H), 3.59 (m, 2H), 3.11 (m, 2H), 2.92 (m, 2H), 2.66 (s, 6H), 1.37 (m, 4H).

EXAMPLE 4

4-(4,4-dimethyl-1-piperidinyl)-N-((3-nitro-4-((2-(phenylsulfanyl)ethyl)amino)phenyl)sulfonyl)benzenecarboximidamide The desired product was prepared by substituting 2-phenylsulfanylethylamine and EXAMPLE 2D for EXAMPLE 1L and EXAMPLE 1I, respectively in EXAMPLE 1N. MS (ESI) m/e 568 (M+H)$^+$; $^1$H NMR (500 MHz, CD$_3$OD) δ 8.61 (d, 1H), 7.87 (dd, 1H), 7.76 (d, 2H), 7.35 (d, 2H), 7.18 (t, 2H), 7.13 (t, 1H), 7.01 (d, 1H), 6.92 (d, 2H), 5.48 (s, 1H), 4.06 (t, 1H), 3.65 (t, 2H), 3.65 (t, 2H), 3.36 (m, 4H), 3.25 (t, 2H), 1.48 (m, 4H), 1.00 (s, 6H).

EXAMPLE 5

4-(4-benzyl-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide

EXAMPLE 5A 4-(4-benzyl-4-hydroxy-1-piperidinyl)benzonitrile

A solution of benzylmagnesium chloride (1.90 mL of a 2M solution in THF, 3.80 mmol) at −78° C. was treated with 4-(4-oxo-1-piperidinyl)benzonitrile (prepared according to the procedure described in Synthesis 1981, 606-608, 0.30 g, 1.51 mmol), and was allowed to warm to room temperature overnight. The reaction mixture was partitioned between ethyl acetate and saturated aqueous NH$_4$Cl and the aqueous layer was extracted with ethyl acetate (2×). The combined organic layers were dried (MgSO$_4$), filtered, and concentrated. The resulting residue was purified by silica gel chromatography eluting with 20% ethyl acetate in hexanes to give the desired product (0.087 g, 20%). MS (ESI) m/e 293 (M+H)$^+$.

EXAMPLE 5B 4-(4-benzyl-4-methoxy-1-piperidinyl)benzonitrile

The desired product was prepared by substituting EXAMPLE 5A for EXAMPLE 1C in EXAMPLE 1D. MS (ESI) m/e (M+H)$^+$.

EXAMPLE 5C 4-(4-benzyl-4-methoxy-1-piperidinyl)benzenecarboximidamide

The desired product was prepared by substituting EXAMPLE 5B for EXAMPLE 1G in EXAMPLE 1H. MS (ESI) m/e (M+H)$^+$.

EXAMPLE 5D 4-(4-benzyl-4-methoxy-1-piperidinyl)-N-((4-fluoro-3-nitrophenyl)sulfonyl)benzenecarboximidamide The desired product was prepared by substituting EXAMPLE 5C for EXAMPLE 1H in EXAMPLE 1I. MS (ESI) m/e (M+H)$^+$.

EXAMPLE 5E 4-(4-benzyl-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide The desired product was prepared by substituting EXAMPLE 5D for EXAMPLE 1I in EXAMPLE 1N. MS (ESI) m/e 731 (M+H)$^+$; $^1$H NMR (400 MHz, DMSO-d$_6$) δ 8.76 (s, 1H), 8.60 (d, 1H), 8.43 (d, 1H), 7.98 (s, 1H), 7.78 (m, 3H), 7.27 (m, 4H), 7.16 (m, 5H), 7.04 (d, 1H), 6.92 (d, 2H), 4.11 (m, 1H), 3.62 (d, 1H), 3.36 (m, 2H), 3.28 (s, 3H), 3.01 (m, 2H), 2.78 (s, 2H), 2.40 (m, 1H), 2.22 (m, 1H), 2.11 (s, 6H), 1.93 (m, 1H), 1.82 (m, 1H), 1.67 (d, 2H), 1.48 (m, 2H).

EXAMPLE 6

4-(4-(cyclohexylmethyl)-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide

EXAMPLE 6A 4-(4-(cyclohexylmethyl)-4-hydroxy-1-piperidinyl)benzonitrile

The desired product was prepared by substituting cyclohexylmethylmagnesium bromide for benzylmagnesium chloride in EXAMPLE 5A. MS (ESI) m/e 299 (M+H)$^+$.

EXAMPLE 6B 4-(4-(cyclohexylmethyl)-4-methoxy-1-piperidinyl)benzonitrile

The desired product was prepared by substituting EXAMPLE 6A for EXAMPLE 1C in EXAMPLE 1D. MS.

EXAMPLE 6C 4-(4-(cyclohexylmethyl)-4-methoxy-1-piperidinyl)benzenecarboximidamide The desired product was prepared by substituting EXAMPLE 6B for EXAMPLE 1G in EXAMPLE 1H. MS.

EXAMPLE 6D 4-(4-(cyclohexylmethyl)-4-methoxy-1-piperidinyl)-N-((4-fluoro-3-nitrophenyl)sulfonyl)benzenecarboximidamide The desired product was prepared by substituting EXAMPLE 6C for EXAMPLE 1H in EXAMPLE 1I. MS

EXAMPLE 6E 4-(4-(cyclohexylmethyl)-4-methoxy-1-piperidinyl)-N-((4-(((1R)-3-(dimethylamino-1-((phenylsulfanyl)methyl)propyl)amino)-3-nitrophenyl)sulfonyl)benzenecarboximidamide The desired product was prepared by substituting EXAMPLE 6D for EXAMPLE 1I in EXAMPLE 1N. MS (ESI) m/e 737 (M+H)$^+$; $^1$H NMR (400 MHz, DMSO-d$_6$) δ 8.77 (s, 1H), 8.61 (d, 1H), 8.42 (d, 1H), 7.98 (s, 1H), 7.78 (d, 3H), 7.27 (d, 2H), 7.13 (m, 3H), 7.04 (d, 1H), 6.93 (d, 2H), 4.10 (m, 1H), 3.58 (d, 2H), 3.36 (m, 2H), 3.07 (s, 3H), 3.03 (m, 2H), 2.39 (m, 1H), 2.20 (m, 1H), 2.10 (s, 6H), 1.95 (m, 1H), 1.80 (m, 5H), 1.60 (m, 3H), 1.45 (m, 3H), 1.31 (d, 2H), 1.15 (m, 3H), 0.96 (m, 2H).

EXAMPLE 7

4-(4-(2,4-difluorobenzyl)-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide

EXAMPLE 7A 4-(4-(2,4-difluorobenzyl)-4-hydroxy-1-piperidinyl)benzonitrile

The desired product was prepared by substituting 2,4-difluorobenzylmagnesium bromide for benzylmagnesium chloride in EXAMPLE 5A. MS (ESI) m/e 329 (M+H)$^+$.

EXAMPLE 7B 4-(4-(2,4-difluorobenzyl)-4-methoxy-1-piperidinyl)benzonitrile

The desired product was prepared by substituting EXAMPLE 7A for EXAMPLE 1C in EXAMPLE 1D. MS

EXAMPLE 7C 4-(4-(2,4-difluorobenzyl)-4-methoxy-1-piperidinyl)benzenecarboximidamide The desired product was prepared by substituting EXAMPLE 7B for EXAMPLE 1G in EXAMPLE 1H. MS

EXAMPLE 7D 4-(4-(2,4-difluorobenzyl)-4-methoxy-1-piperidinyl)-N-((4-fluoro-3-nitrophenyl)sulfonyl)benzenecarboximidamide The desired product was prepared by substituting EXAMPLE 7C for EXAMPLE 1H in EXAMPLE 1I. MS

EXAMPLE 7E 4-(4-(2,4-difluorobenzyl)-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide The desired product was prepared by substituting EXAMPLE 7D for EXAMPLE 1I in EXAMPLE 1N. MS (ESI) m/e 767 (M+H)$^+$; $^1$H NMR (400 MHz, DMSO-d$_6$) δ 8.77 (s, 1H), 8.62 (d, 1H), 8.43 (d, 1H), 7.98 (s, 1H), 7.78 (m, 3H), 7.28 (m, 3H), 7.14 (m, 3H), 7.02 (m, 2H), 6.93 (d, 2H), 4.11 (m, 1H), 3.64 (d, 2H), 3.36 (m, 2H), 3.26 (s, 3H), 2.99 (m, 2H), 2.79 (s, 2H), 2.38 (m, 1H), 2.20 (m, 1H), 2.08 (s, 6H), 1.94 (m, 1H), 1.81 (m, 1H), 1.69 (d, 2H), 1.49 (m, 2H).

EXAMPLE 8

N-((4-(((1R)-3-(dimethylamino)-1-((phenylsulfanyl)methyl)propyl)amino)-3-nitrophenyl)sulfonyl)-4-(4-methoxy-4-(2-methylbenzyl)-1-piperidinyl)benzenecarboximidamide

EXAMPLE 8A 4-(4-hydroxy-4-(2-methylbenzyl)-1-1-piperidinyl)benzonitrile

The desired product was prepared by substituting 2-methylbenzylmagnesium bromide for benzylmagnesium chloride in EXAMPLE 5A. MS (ESI) m/e 307 (M+H)$^+$.

EXAMPLE 8B 4-(4-methoxy-4-(2-methylbenzyl)-1-piperidinyl)benzonitrile

The desired product was prepared by substituting EXAMPLE 8A for EXAMPLE 1C in EXAMPLE 1D. MS

EXAMPLE 8C 4-(4-methoxy-4-(2-methylbenzyl)-1-piperidinyl)benzenecarboximidamide The desired product was prepared by substituting EXAMPLE 8B for EXAMPLE 1G in EXAMPLE 1H. MS

EXAMPLE 8D

N-((4-fluoro-3-nitrophenyl)sulfonyl)-4-(4-methoxy-4-(2-methylbenzyl)-1-piperidinyl)benzenecarboximidamide The desired product was prepared by substituting EXAMPLE 8C for EXAMPLE 1H in EXAMPLE 1I. MS

EXAMPLE 8E

N-((4-(((1R)-3-(dimethylamino)-1-((phenylsulfanyl)methyl)propyl)amino)-3-nitrophenyl)sulfonyl)-4-(4-methoxy-4-(2-methylbenzyl)-1-piperidinyl)benzenecarboximidamide The desired product was prepared by substituting EXAMPLE 8D for EXAMPLE 1I in EXAMPLE 1L. MS (ESI) m/e 745 (M+H)$^+$; $^1$H NMR (400 MHz, DMSO-d$_6$) δ 8.75 (s, 1H), 8.61 (d, 1H), 8.42 (d, 1H), 7.97 (s, 1H), 7.77 (m, 3H), 7.27 (m, 2H), 7.11 (m, 7H), 6.91 (d, 2H), 4.10 (m, 1H), 3.64 (d, 2H), 3.36 (m, 2H), 3.28 (s, 3H), 2.96 (m, 2H), 2.80 (s, 2H), 2.39 (m, 1H), 2.27 (s, 3H), 2.20 (m, 1H), 2.10 (s, 6H), 1.93 (m, 1H), 1.79 (m, 3H), 1.49 (m, 2H).

EXAMPLE 9

N-((4-(((1R)-3-(dimethylamino)-1-((phenylsulfanyl)methyl)propyl)amino)-3-nitrophenyl)sulfonyl)-4-(4-(4-fluorobenzylidene)-1-piperidinyl)benzenecarboximidamide

EXAMPLE 9A 4-(4-(4-fluorobenzylidene)-1-piperidinyl)benzonitrile

A suspension of the 4-fluorobenzyl triphenylphosphonium chloride (0.737 g, 1.81 mmol) in THF (10 mL) was treated with nBuLi (724 μL of a 1.6M solution in hexanes, 1.81 mmol) at 0° C., treated with 1-(4'-cyanophenyl)-4-oxopiperidine (prepared according to the procedure described in Synthesis 1981, 606-608, 0.300 g, 1.51 mmol), and gradually warmed to room temperature overnight. The reaction mixture was partitioned between ethyl acetate and saturated aqueous NH$_4$Cl and the aqueous layer was extracted with ethyl acetate (2×). The combined organic layers were dried (MgSO$_4$), filtered, and concentrated. The resulting residue was purified by silica gel chromatography eluting with 10% ethyl acetate in hexanes to give the desired product. (0.268 g, 61%). MS (ESI) m/e 292 (M+H)+.

EXAMPLE 9B 4-(4-(4-fluorobenzylidene)-1-piperidinyl)benzenecarboximidamide

The desired product was prepared by substituting EXAMPLE 9A for EXAMPLE 1G in EXAMPLE 1H. MS

EXAMPLE 9C 4-(4-(4-fluorobenzylidene)-1-piperidinyl)-N-((4-fluoro-3-nitrophenyl)sulfonyl)benzenecarboximidamide The desired product was prepared by substituting EXAMPLE 9B for EXAMPLE 1H in EXAMPLE 1I. MS

EXAMPLE 9D

N-((4-(((1R)-3-(dimethylamino)-1-((phenylsulfanyl)methyl)propyl)amino)-3-nitrophenyl)sulfonyl)-4-(4-(4-fluorobenzylidene)-1-piperidinyl)benzenecarboximidamide The desired product was prepared by substituting EXAMPLE 9C for EXAMPLE 1I in EXAMPLE 1N. MS (ESI) m/e 717 (M+H)+; $^1$H NMR (400 MHz, DMSO-d$_6$) δ 8.78 (s, 1H), 8.61 (d, 1H), 8.44 (d, 1H), 8.00 (d, 1H), 7.80 (m, 3H), 7.27 (m, 4H), 7.15 (m, 5H), 7.05 (d, 1H), 6.97 (d, 2H), 6.37 (s, 1H), 4.11 (m, 1H), 3.51 (m, 2H), 3.43 (m, 2H), 3.36 (m, 2H), 2.50 (m, 2H), 2.39 (m, 3H), 2.21 (m, 1H), 2.11 (s, 6H), 1.94 (m, 1H), 1.80 (m, 1H).

EXAMPLE 10

N-((4-(((1R)-3-(dimethylamino)-1-((phenylsulfanyl)methyl)propyl)amino)-3-nitrophenyl)sulfonyl)-4-(4-(2-(trifluoromethyl)benzylidene)-1-piperidinyl)benzenecarboximidamide

EXAMPLE 10A 4-(4-(2-(trifluoromethyl)benzylidene)-1-piperidinyl)benzonitrile The desired product was prepared by substituting 2-(trifluoromethyl)benzyl triphenylphosphonium bromide (prepared according to the procedure described in J. Chem. Soc. Perkin Trans. I 1995, 18, 2293-2308) for 4-fluorobenzyl triphenylphosphoniumchloride in EXAMPLE 9A. MS (ESI) m/e 343 (M+H)+.

EXAMPLE 10B 4-(4-(2-(trifluoromethyl)benzylidene)-1-piperidinyl)benzenecarboximidamide The desired product was prepared by substituting EXAMPLE 10A for EXAMPLE 1G in EXAMPLE 1H. MS

EXAMPLE 10C

N-((4-fluoro-3-nitrophenyl)sulfonyl)-4-(4-(2-(trifluoromethyl)benzylidene)-1-piperidinyl)benzenecarboximidamide The desired product was prepared by substituting EXAMPLE 10B for EXAMPLE 1H in EXAMPLE 1I. MS

EXAMPLE 10D

N-((4-(((1R)-3-(dimethylamino)-1-((phenylsulfanyl)methyl)propyl)amino)-3-nitrophenyl)sulfonyl)-4-(4-(2-(trifluoromethyl)benzylidene)-1-piperidinyl)benzenecarboximidamide The desired product was prepared by substituting EXAMPLE 10C for EXAMPLE 1I in EXAMPLE 1N. MS (ESI) m/e 765 (M−H)−; $^1$H NMR (400 MHz, DMSO-d$_6$) δ 8.79 (s, 1H), 8.62 (d, 1H), 8.44 (d, 1H), 8.01 (s, 1H), 7.79 (m, 3H), 7.73 (d, 1H), 7.64 (t, 1H), 7.47 (t, 1H), 7.36 (d, 1H), 7.28 (m, 2H), 7.14 (m, 3H), 7.04 (d, 1H), 6.98 (d, 1H), 6.50 (s, 1H), 4.12 (m, 1H), 3.51 (m, 2H), 3.36 (m, 4H), 2.40 (m, 3H), 2.22 (m, 3H), 2.10 (s, 6H), 1.93 (m, 1H), 1.80 (m, 1H).

EXAMPLE 11

N-((4-(((1R)-3-(dimethylamino)-1-((phenylsulfanyl)methyl)propyl)amino)-3-nitrophenyl)sulfonyl)-4-(4-(3-thienylmethylene)-1-piperidinyl)benzenecarboximidamide

EXAMPLE 11A 4-(4-(3-thienylmethylene)-1-piperidinyl)benzonitrile

The desired product was prepared by substituting thiophen-3-ylmethyltriphenyl phosphonium bromide for 4-fluorobenzyl triphenylphosphonium chloride in EXAMPLE 9A. MS

EXAMPLE 11B 4-(4-(3-thienylmethylene)-1-piperidinyl)benzenecarboximidamide

The desired product was prepared by substituting EXAMPLE 11A for EXAMPLE 1G in EXAMPLE 1H. MS

EXAMPLE 11C

N-((4-fluoro-3-nitrophenyl)sulfonyl)-4-(4-(3-thienylmethylene)-1-piperidinyl)benzenecarboximidamide The desired product was prepared by substituting EXAMPLE 11B for EXAMPLE 1I in EXAMPLE 1N. MS

EXAMPLE 11D

N-((4-(((1R)-3-(dimethylamino)-1-((phenylsulfanyl)methyl)propyl)amino)-3-nitrophenyl)sulfonyl)-4-(4-(3-thienylmethylene)-1-piperidinyl)benzenecarboximidamide The desired product was prepared by substituting EXAMPLE 11C for EXAMPLE 1I in EXAMPLE 1N. MS (ESI) m/e 705 (M+H)+; $^1$H NMR (400 MHz, DMSO-d$_6$) δ 8.78 (s, 1H), 8.61 (d, 1H), 8.43 (d, 1H), 7.99 (s, 1H), 7.81 (d, 2H), 7.78 (d, 1H), 7.51 (dd, 1H), 7.32 (m, 1H), 7.28 (m, 2H), 7.13 (m, 4H), 7.04 (d, 1H), 6.95 (d, 2H), 6.32 (s, 1H), 4.11 (m, 1H), 3.48 (m, 4H), 3.37 (m, 2H), 2.58 (t, 2H), 2.39 (m, 3H), 2.21 (m, 1H), 2.11 (s, 6H), 1.93 (m, 1H), 1.81 (m, 1H).

EXAMPLE 12

N-((4-(((1R)-3-(dimethylamino)-1-((phenylsulfanyl)methyl)propyl)amino)-3-nitrophenyl)sulfonyl)-4-(4-(3,3-diphenyl-2-propenyl)-1-piperazinyl)benzenecarboximidamide

EXAMPLE 12A 4-(4-(3,3-diphenyl-2-propenyl)-1-piperazinyl)benzonitrile

A suspension of 4-piperazin-1-ylbenzonitrile hydrochloride (1.30 g, 5.00 mmol) and 3,3-diphenylacrylaldehyde (1.56 g, 7.50 mmol)) in dichloromethane (10 mL) and methanol (10 mL) was neutralized to pH 5 with diisopropylethylamine, treated with polymer-supported cyanoborohydride (2.47 mmol/g, 6 g, 14.82 mmol), shaken at room temperature for 24 hours, and filtered. The resin was washed with 1:1 dichloromethane/methanol (10 mL×3) and the combined filtrates were concentrated. The concentrate was purified by silica gel chromatography eluting with a gradient from 10%-50% ethyl acetate/hexanes to provide the desired product (1.60 g, 84%). MS (CI) m/e 380 (M+H)$^+$.

EXAMPLE 12B 4-(4-(3,3-diphenyl-2-propenyl)-1-piperazinyl)benzenecarboximidamide A solution of EXAMPLE 12A (0.515 g, 1.36 mmol) in dry tetrahydrofuran (6 mL) was treated dropwise with LiHMDS (1M, 6.8 mL, 6.8 mmol), stirred for 16 hours, quenched with 1N HCl (8 mL), and filtered. The filter cake was collected to provide the desired product (0.45 g, 71%) that was used without further purification. MS (CI) m/e 397 (M+H)$^+$.

EXAMPLE 12C

N-((4-chloro-3-nitrophenyl)sulfonyl)-4-(4-(3,3-diphenyl-2-propenyl)-1-piperazinyl)benzenecarboximidamide A suspension of EXAMPLE 12B (0.421 g, 0.897 mmol) and diisopropylethylamine (0.50 mL) in dichloromethane (5 mL) was treated with 4-chloro-3-nitrobenzenesulfonyl chloride (0.252 g, 0.99 mmol), stirred at room temperature for 24 hours and concentrated. The resulting residue was purified by silica gel chromatography eluting with a gradient from 0%-10% methanol/dichloromethane to give the desired product (0.33 g, 60%). MS (ESI) m/e 614 (M−H)$^−$.

EXAMPLE 12D

N-((4-(((1R)-3-(dimethylamino)-1-((phenylsulfanyl)methyl)propyl)amino)-3-nitrophenyl)sulfonyl)-4-(4-(3,3-diphenyl-2-propenyl)-1-piperazinyl)benzenecarboximidamide The desired product was prepared by substituting EXAMPLE 12C for EXAMPLE 1I in EXAMPLE 1N. MS (ESI) m/e 802 (M−H)$^−$; $^1$H NMR (500 MHz, DMSO-d$_6$) δ 10.32 (br s, 1H), 9.64 (s, 1H), 8.90 (s, 1H), 8.44 (d, 1H), 8.20 (d, 1H), 8.09 (s, 1H), 7.83 (m, 3H), 7.47 (t, 2H), 7.42 (m, 1H), 7.37 (m, 3H), 7.26 (m, 4H), 7.17 (m, 3H), 7.14 (d, 2H), 7.11 (m, 2H), 7.02 (d, 2H), 6.27 (t, 1H), 4.16 (m, 1H), 4.02 (br s, 1H), 3.85 (d, 2H), 3.54 (br s, 1H), 3.12 (m, 6H), 2.74 (s, 6H), 2.14 (q, 2H).

EXAMPLE 13

4-(4-benzyl-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide

EXAMPLE 13A methyl 4-(4-benzyl-4-methoxycyclohexyl)-N-cyano-1-piperazinecarbimidothioate A solution of 1-(4-benzyl-4-methoxycyclohexyl)piperazine (prepared according to the procedure described in commonly owned U.S. patent application Ser. No. 10/269,739, filed Oct. 14, 2002, 0.052 g, 0.181 mmol) in dichloromethane (5 mL) was treated with dimethyl cyanothioiminocarbonate (0.026 mg, 0.181 mmol), heated to 40° C. overnight and concentrated. The crude material was used without further purification. MS.

EXAMPLE 13B 4-(4-benzyl-4-methoxycyclohexyl)-N-cyano-N'-((4-(((1R)-3-(dimethylamino)-1-((phenylsulfanyl)methyl)propyl)amino)-3-nitrophenyl)sulfonyl)-1-piperazinecarboximidamide A solution of the EXAMPLE 13A (0.070 g, 0.181 mmol) in methanol (4.5 mL) and water (0.5 mL) was treated with 4-(((1R)-3-(dimethylamino)-1-((phenylthio)methyl)propyl)amino)-3-nitrobenzenesulfonamide (prepared according to the procedure described in commonly owned U.S. patent application Ser. No. 09/957,256, filed Sep. 20, 2001, 0.069 g, 0.181 mmol) and NaOH (0.022 g, 0.543 mmol) and was heated to 50° C. overnight. The solution was partitioned between dichloromethane and saturated NaHCO$_3$. The organic layer was separated and the aqueous layer was extracted with dichloromethane three times. The combined organic layers were dried (MgSO$_4$), filtered, and concentrated. The resulting residue was purified by C18 reverse phase HPLC eluting with a gradient from 10-100% acetonitrile in 0.1% aqueous TFA to give the desired product. MS

EXAMPLE 13C 4-(4-benzyl-4-methoxycyclohexyl)-N-((4-(((1R)-3-(dimethylamino)-1-((phenylsulfanyl)methylpropyl)amino)-3-nitrophenyl)sulfonyl)-1-piperazinecarboximidamide A solution of EXAMPLE 13B (0.020 g, 0.026 mmol) in 2N HCl (1 mL) and CH$_3$OH (1 mL) was heated to 50° C. overnight and concentrated. The resulting residue was purified by C18 reverse phase HPLC eluting with a gradient from 10-100% acetonitrile in 0.1% aqueous TFA to give the desired product (0.0084 g, 42%). MS; $^1$H NMR (300 MHz, CD$_3$OD) δ 8.44 (m, 1H), 7.74 (m, 1H), 7.22 (m, 10H), 6.97

(m, 1H), 4.12 (m, 1H), 3.45 (m, 10H), 3.30 (s, 3H), 3.25 (m, 1H), 3.13 (s, 6H), 2.74 (m, 2H), 2.56 (m, 3H), 2.32 (m, 3H), 1.52 (m, 10H).

EXAMPLE 14

N-((4-(((1R)-3-(dimethylamino)-1-((phenylsulfanyl)methyl)propyl)amino)-3-nitrophenyl)sulfonyl)-4-phenyl-1-piperazinecarboximidamide

EXAMPLE 14A methyl N-cyano-4-phenyl-1-piperazinecarbimidothioate

The desired product was prepared by substituting 1-phenylpiperazine for 1-(4-benzyl-4-methoxycyclohexyl)piperazine in EXAMPLE 13A. MS

EXAMPLE 14B

N-cyano-N'-((4-(((1R)-3-(dimethylamino)-1-((phenylsulfanyl)methyl)propyl)amino)-3-nitrophenyl)sulfonyl)-4-phenyl-1-piperazinecarboximidamide The desired product was obtained by substituting EXAMPLE 14A for EXAMPLE 13A in EXAMPLE 13B. MS

EXAMPLE 14C

N-((4-(((1R)-3-(dimethylamino)-1-((phenylsulfanyl)methyl)propyl)amino)-3-nitrophenyl)sulfonyl)-4-phenyl-1-piperazinecarboximidamide The desired product was obtained by substituting EXAMPLE 14B for EXAMPLE 13B in EXAMPLE 13C. MS; $^1$H NMR (300 MHz, CD$_3$OD) δ 8.47 (d, 1H), 7.76 (dd, 1H), 7.25 (m, 4H), 7.14 (m, 3H), 6.96 (m, 3H), 6.86 (t, 1H), 4.12 (m, 1H), 3.71 (m, 4H), 3.44 (m, 4H), 3.16 (m, 4H), 3.12 (s, 6H), 2.36 (m, 2H).

EXAMPLE 15

N-((4-(((1R)-3-(dimethylamino)-1-((phenylsulfanyl)methyl)propyl)amino)-3-nitrophenyl)sulfonyl)-4-(4-methoxy-4-(2-methylbenzyl)cyclohexyl)-1-piperazinecarboximidamide

EXAMPLE 15A 8-(2-methylbenzyl)-1,4-dioxaspiro(4.5)decan-8-ol

A solution of 2-methylbenzyl chloride (0.579 g, 4.12 mmol) in THF (20 mL) was treated with Mg (0.180 g, 7.50 mmol) and stirred at room temperature until all the Mg had dissolved. The mixture was cooled to 0° C., treated with a solution of 1,4-cyclohexanedione mono-ethylene ketal (0.579 g, 4.12 mmol) in THF (50 mL), warmed to room temperature, stirred overnight, quenched with saturated NH$_4$Cl (100 mL), and extracted with ethyl acetate (3×100 mL). The combined extracts were washed with water and brine, dried (Na$_2$SO$_4$), filtered, and concentrated. The concentrate was purified by flash column chromatography on silica gel with 6:1 hexanes/ethyl acetate to provide the desired product (0.48 g, 44%) MS (ESI) m/e 262 (M+H)$^+$.

EXAMPLE 15B 8-methoxy-8-(2-methylbenzyl)-1,4-dioxaspiro(4.5)decane

The desired product was obtained by substituting EXAMPLE 15A for EXAMPLE 1C in EXAMPLE 1D. MS (ESI) m/e 294 (M+NH$_4$)$^+$.

EXAMPLE 15C 4-methoxy-4-(2-methylbenzyl)cyclohexanone

A solution of EXAMPLE 15B (0.51 g, 1.80 mmol) in acetone (10 mL) was treated with water (5 mL) and p-toluenesulfonic acid monohydrate (0.20 g), heated to reflux, stirred overnight, and concentrated to remove the acetone. The remaining aqueous solution was extracted with ethyl acetate (3×100 mL) and the combined extracts were washed sequentially with 1N NaOH, water, and brine, dried (Na$_2$SO$_4$), filtered, and concentrated to provide the desired product (0.42 g, 100%). MS (ESI) m/e 233 (M+H)$^+$.

EXAMPLE 15D tert-butyl 4-(4-methoxy-4-(2-methylbenzyl)cyclohexyl)-1-piperazinecarboxylate A solution of EXAMPLE 15C (0.42 g, 1.80 mmol) and 1-tert-butoxycarbonylpiperazine (0.391 g, 2.10 mmol) in dichloroethane (10 mL) at room temperature was treated with acetic acid (500 μL) and sodium triacetoxyborohydride (10.89 g, 4.2 mmol), stirred overnight, diluted with ethyl acetate (300 mL), washed sequentially with 1N NaOH, water, and brine, dried (Na$_2$SO$_4$), filtered, and concentrated to provide the desired product (0.51 g, 70%); MS (ESI) m/e 403 (M+H)$^+$.

EXAMPLE 15E 1-(4-methoxy-4-(2-methylbenzyl)cyclohexyl)piperazine

A solution of EXAMPLE 15D (0.51 g, 1.26 mmol) in dichloromethane (5 mL) at room temperature was treated with 2M HCl in diethyl ether (5 mL), stirred overnight, and concentrated to provide the desired product (0.38 g, 100%). MS (ESI) m/e 303 (M+H)$^+$.

EXAMPLE 15F methyl N-cyano-4-(4-methoxy-4-(2-methylbenzyl)cyclohexyl)-1-piperazinecarbimidothioate The desired product was prepared by substituting EXAMPLE 15E for 1-(4-benzyl-4-methoxycyclohexyl)piperazine in EXAMPLE 13A. MS

EXAMPLE 15G

N-cyano-N'-((4-(((1R)-3-(dimethylamino)-1-((phenylsulfanyl)methyl)propyl)amino)-3-nitrophenyl)sulfonyl)-4-(4-methoxy-4-(2-methylbenzyl)cyclohexyl)-1-piperazinecarboximidamide The desired product was obtained by substituting EXAMPLE 15F for EXAMPLE 13A in EXAMPLE 13B. MS

EXAMPLE 15H

N-((4-(((1R)-3-(dimethylamino)-1-((phenylsulfanyl)methyl)propyl)amino)-3-nitrophenyl)sulfonyl)-4-(4-methoxy-4-(2-methylbenzyl)cyclohexyl)-1-piperazinecarboximidamide The desired product was obtained by substituting EXAMPLE 15G for EXAMPLE 13B in EXAMPLE 13C. MS; $^1$H NMR (300 MHz, CD$_3$OD) δ 8.46 (d, 1H), 8.21 (d, 1H), 7.76 (dd, 1H), 7.29 (m, 2H), 7.12 (m, 6H), 6.97 (d, 1H), 4.13 (m, 1H), 3.37 (m, 12H), 3.15 (m, 8H), 2.85 (m, 2H), 2.34 (m, 5H), 1.30-2.0 (m, 10H).

EXAMPLE 16

4-(4-(2-chlorobenzyl)-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide

EXAMPLE 16A 8-(2-chlorobenzyl)-1,4-dioxaspiro(4.5)decan-8-ol

The desired product was prepared by substituting 2-chlorobenzylbromide for 2-methylbenzyl chloride in EXAMPLE 15A. MS (ESI) m/e 300 (M+H)$^+$.

EXAMPLE 16B 8-(2-chlorobenzyl)-8-methoxy-1,4-dioxaspiro(4.5)decane

The desired product was prepared by substituting EXAMPLE 16A for EXAMPLE 1C in EXAMPLE 1D. MS (ESI) m/e 332 (M+NH$_4$)$^+$.

EXAMPLE 16C 4-(2-chlorobenzyl)-4-methoxycyclohexanone

The desired product was prepared by substituting EXAMPLE 16B for EXAMPLE 15B in EXAMPLE 15C. MS (ESI) m/e 270 (M+NH$_4$)$^+$.

EXAMPLE 16D tert-butyl 4-(4-(2-chlorobenzyl)-4-methoxycyclohexyl)-1-piperazinecarboxylate The desired product was prepared by substituting EXAMPLE 16C for EXAMPLE 15C in EXAMPLE 15D. MS (ESI) m/e 423 (M+H)$^+$.

EXAMPLE 16E 1-(4-(2-chlorobenzyl)-4-methoxycyclohexyl)piperazine

The desired product was prepared by substituting EXAMPLE 16D for EXAMPLE 15D in EXAMPLE 15E. MS (ESI) m/e 323 (M+H)$^+$.

EXAMPLE 16F methyl 4-(4-(2-chlorobenzyl)-4-methoxycyclohexyl)-N-cyano-1-piperazinecarbimidothioate The desired product was prepared by substituting EXAMPLE 16E for 1-(4-benzyl-4-methoxycyclohexyl)piperazine in EXAMPLE 13A. MS

EXAMPLE 16G 4-(4-(2-chlorobenzyl)-4-methoxycyclohexyl)-N-cyano-N'-((4-(((1R)-3-(dimethylamino)-1-((phenylsulfanyl)methyl)propyl)amino)-3-nitrophenyl)sulfonyl)-1-piperazinecarboximidamide The desired product was prepared by substituting EXAMPLE 16F for EXAMPLE 13A in EXAMPLE 13B. MS

EXAMPLE 16H 4-(4-(2-chlorobenzyl)-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide The desired product was prepared by substituting EXAMPLE 16G for EXAMPLE 13B in EXAMPLE 13C. MS; $^1$H NMR (300 MHz, CD$_3$OD) δ 8.46 (d, 1H), 8.21 (d, 1H), 7.76 (m, 1H), 7.35 (m, 1H), 7.29 (m, 3H), 7.19 (m, 4H), 6.98 (m, 1H), 4.14 (m, 1H), 3.45 (m, 3H), 3.35 (s, 3H), 3.21 (m, 3H), 3.13 (m, 7H), 3.03 (m, 6H), 2.34 (m, 2H), 1.68 (m, 10H).

EXAMPLE 17

N-((4-(((1R)-3-(dimethylamino)-1-((phenylsulfanyl)methyl)propyl)amino)-3-nitrophenyl)sulfonyl)-4-(4-(2-fluorobenzyl)-4-methoxycyclohexyl)-1-piperazinecarboximidamide

EXAMPLE 17A 8-(2-fluorobenzyl)-1,4-dioxaspiro(4.5)decan-8-ol

The desired product was prepared by substituting 2-fluorobenzyl bromide for 2-methylbenzyl chloride in EXAMPLE 15A. MS (ESI) m/e 284 (M+NH$_4$)$^+$.

EXAMPLE 17B 8-(2-fluorobenzyl)-8-methoxy-1,4-dioxaspiro(4.5)decane

The desired product was prepared by substituting EXAMPLE 17A for EXAMPLE 1C in EXAMPLE 1D. MS (ESI) m/e 298 (M+NH$_4$)$^+$.

EXAMPLE 17C 4-(2-fluorobenzyl)-4-methoxycyclohexanone

The desired product was prepared by substituting EXAMPLE 16B for EXAMPLE 15B in EXAMPLE 15C. MS (ESI) m/e 254 (M+NH$_4$)$^+$.

EXAMPLE 17D tert-butyl 4-(4-(2-fluorobenzyl)-4-methoxycyclohexyl)-1-piperazinecarboxylate The desired product was prepared by substituting EXAMPLE 17C for EXAMPLE 15C in EXAMPLE 15D. MS (ESI) m/e 407 (M+H)$^+$.

EXAMPLE 17E 1-(4-(2-fluorobenzyl)-4-methoxycyclohexyl)piperazine

The desired product was prepared by substituting EXAMPLE 17D for EXAMPLE 15D in EXAMPLE 15E. MS (ESI) m/e 307 (M+H)$^+$.

EXAMPLE 17F methyl N-cyano-4-(4-(2-fluorobenzyl)-4-methoxycyclohexyl)-1-piperazinecarbimidothioate The desired product was prepared by substituting EXAMPLE 17E for 1-(4-benzyl-4-methoxycyclohexyl)piperazine in EXAMPLE 13A. MS

EXAMPLE 17G

N-cyano-N'-((4-(((1R)-3-(dimethylamino)-1-((phenylsulfanyl)methyl)propyl)amino)-3-nitrophenyl)sulfonyl)-4-(4-(2-fluorobenzyl)-4-methoxycyclohexyl)-1-piperazinecarboximidamide The desired product was prepared by substituting EXAMPLE 17F for EXAMPLE 13A in EXAMPLE 13B. MS

EXAMPLE 17H

N-((4-(((1R)-3-(dimethylamino)-1-((phenylsulfanyl)methyl)propyl)amino)-3-nitrophenyl)sulfonyl)-4-(4-(2-fluorobenzyl)-4-methoxycyclohexyl)-1-piperazinecarboximidamide The desired product was prepared by substituting EXAMPLE 17G for EXAMPLE 13B in EXAMPLE 13C. MS; $^1$H NMR (300 MHz, CD$_3$OD) δ 8.48 (m, 1H), 8.22 (d, 1H), 7.77 (m, 10H), 7.30 (m, 2H), 7.20 (m, 4H), 7.03 (m, 3H), 4.14 (m, 1H), 3.45 (m, 6H), 3.34 (s, 3H), 3.24 (m, 5H), 3.13 (s, 6H), 2.86 (d, 2H), 2.32 (m, 2H), 1.73 (m, 10H).

EXAMPLE 18

4-(4-(2-bromobenzyl)-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide

EXAMPLE 18A 8-(2-bromobenzyl)-1,4-dioxaspiro(4.5)decan-8-ol

The desired product was prepared by substituting 2-bromobenzyl bromide for 2-methylbenzyl chloride in EXAMPLE 15A. MS (ESI) m/e 328 (M+H)$^+$.

EXAMPLE 18B 8-(2-bromobenzyl)-8-methoxy-1,4-dioxaspiro(4.5)decane

The desired product was prepared by substituting EXAMPLE 18A for EXAMPLE 1C in EXAMPLE 1D. MS (ESI) m/e 360 (M+NH$_4$)$^+$.

EXAMPLE 18C 4-(2-bromobenzyl)-4-methoxycyclohexanone

The desired product was prepared by substituting EXAMPLE 18B for EXAMPLE 15B in EXAMPLE 15C. MS (ESI) m/e 315 (M+NH$_4$)$^+$.

EXAMPLE 18D tert-butyl 4-(4-(2-bromobenzyl)-4-methoxycyclohexyl)-1-piperazinecarboxylate The desired product was prepared by substituting EXAMPLE 18C for EXAMPLE 15C in EXAMPLE 15D. MS (ESI) m/e 468 (M+H)$^+$.

EXAMPLE 18E 1-(4-(2-bromobenzyl)-4-methoxycyclohexyl)piperazine

The desired product was prepared by substituting EXAMPLE 18D for EXAMPLE 15D in EXAMPLE 15E. MS (ESI) m/e 367 (M+H)$^+$.

EXAMPLE 18F methyl 4-(4-(2-bromobenzyl)-4-methoxycyclohexyl)-N-cyano-1-piperazinecarbimidothioate The desired product was prepared by substituting EXAMPLE 18E for 1-(4-benzyl-4-methoxycyclohexyl)piperazine in EXAMPLE 13A. MS

EXAMPLE 18G 4-(4-(2-bromobenzyl)-4-methoxycyclohexyl)-N-cyano-N'-((4-(((1R)-3-(dimethylamino)-1-((phenylsulfanyl)methyl)propyl)amino)-3-nitrophenyl)sulfonyl)-1-piperazinecarboximidamide The desired product was prepared by substituting EXAMPLE 18F for EXAMPLE 13A in EXAMPLE 13B. MS

EXAMPLE 18H 4-(4-(2-bromobenzyl)-4-methoxycyclohexyl)-N-((4-(((1R)-3-(dimethylamino)-1-((phenylsulfanyl)methyl)propyl)amino)-3-nitrophenyl)sulfonyl)-1-piperazinecarboximidamide The desired product was prepared by substituting EXAMPLE 18G for EXAMPLE 13B in EXAMPLE 13C. MS; $^1$H NMR (300 MHz, CD$_3$OD) δ 8.44 (d, 1H), 7.75 (m, 1H), 7.53 (m, 1H), 7.29 (m, 4H), 7.16 (m, 3H), 7.09 (m, 1H), 6.97 (m, 1H), 4.11 (m, 1H), 3.44 (m, 9H), 3.34 (d, 3H), 3.15

(m, 8H), 3.00 (d, 2H), 2.60 (m, 2H), 2.31 (m, 2H), 1.91 (m, 1H), 1.69 (m, 3H), 1.42 (m, 3H).

EXAMPLE 19

4-(4-methoxy-4-(2-methylbenzyl)-1-piperidinyl)-N-((3-nitro-4-((2-(phenylsulfanyl)ethyl)amino)phenyl)sulfonyl)benzenecarboximidamide The desired product was prepared by substituting 2-phenylsulfanylethylamine (prepared according to the procedure described in Chem. Pharm. Bull 1995, 43, 2091-2094) and EXAMPLE 8D for EXAMPLE 1M and EXAMPLE 1I, respectively, in EXAMPLE 1N. MS (ESI) m/e 672 (M–H)$^-$; $^1$H NMR (500 MHz, CDCl$_3$) δ 8.76 (d, 1H), 8.53 (t, 1H), 8.16 (br s, 1H), 7.93 (dd, 1H), 7.68 (d, 2H), 7.40 (d, 2H), 7.26 (m, 2H), 7.13 (m, 4H), 6.88 (d, 2H), 6.77 (d, 1H), 3.55 (m, 4H), 3.36 (s, 3H), 3.16 (m, 4H), 2.85 (s, 2H), 2.32 (s, 3H), 1.87 (d, 2H), 1.69 (m, 2H).

EXAMPLE 20

N-((4-((1,1-dimethyl-2-(phenylsulfanyl)ethyl)amino)-3-nitrophenyl)sulfonyl)-4-(4-methoxy-4-(2-methylbenzyl)-1-piperidinyl)benzenecarboximidamide The desired product was prepared by substituting 1,1-dimethyl-2-phenylsulfanyl-ethylamine (prepared according to the procedure described in commonly owned U.S. patent application Ser. No. 09/957,256, filed Sep. 20, 2001) and EXAMPLE 8D for EXAMPLE 1M and EXAMPLE 1I, respectively, in EXAMPLE 1N. MS (ESI) m/e 702 (M+H)$^+$; $^1$H NMR (500 MHz, DMSO-d$_6$) δ 8.79 (s, 1H), 8.45 (s, 1H), 8.39 (d, 1H), 8.00 (s, 1H), 7.79 (d, 2H), 7.75 (dd, 1H), 7.32 (d, 1H), 7.25 (d, 2H), 7.11 (m, 4H), 7.00 (t, 2H), 6.93 (m, 3H), 3.64 (d, 2H), 3.52 (s, 2H), 3.28 (s, 3H), 2.97 (m, 2H), 2.80 (s, 2H), 2.27 (s, 3H), 1.75 (d, 2H), 1.55 (s, 6H), 1.50 (m, 2H).

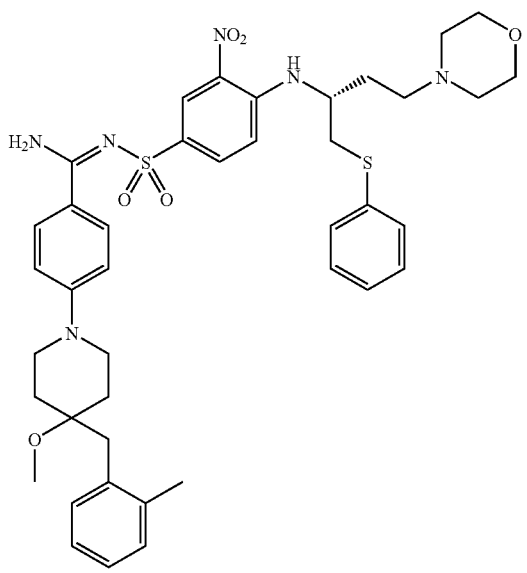

EXAMPLE 21

4-(4-methoxy-4-(2-methylbenzyl)-1-piperidinyl)-N-((4-(((1R)-3-(4-morpholinyl)-1-((phenylsulfanyl)methyl)propyl)amino)-3-nitrophenyl)sulfonyl)benzenecarboximidamide

EXAMPLE 21A benzyl (3R)-2,5-dioxotetrahydro-3-furanylcarbamate

A stirred suspension of N-(benzyloxycarbonyl)-D-aspartic acid (14.7 g, 55.1 mmol) in ethyl acetate (100 mL) was treated dropwise with thionyl chloride (40 mL, 511 mmol) and the resulting homogeneous mixture was stirred at room temperature for 16 hours, and concentrated. The resulting solid was triturated in 1:1 diethyl ether/hexanes (200 mL) for 2 hours and filtered. The solid was dried to provide the desired product (13.7 g, 99%).

EXAMPLE 21B benzyl (3R)-5-oxotetrahydro-3-furanylcarbamate

A suspension of NaBH$_4$ (2.71 g, 71.5 mmol) in THF (50 mL) was cooled to 0° C., treated dropwise with a solution of EXAMPLE 21A (16.21 g, 65.0 mmol) in THF (50 mL), allowed to warm to room temperature, and stirred for 2 hours. The resulting mixture was treated with concentrated HCl (13.1 mL) and ethanol (13.1 mL), heated to reflux for 12 hours, allowed to cool to room temperature, poured into brine (100 mL) and the layers were separated. The aqueous phase was extracted with ethyl acetate and the combined organic layers were washed with water and brine, dried (MgSO$_4$), filtered, and concentrated. The concentrate was triturated with diethyl ether (50 mL) for 2 hours, cooled overnight, and the solid collected by filtration to provide the desired product (7.81 g, 51%).

EXAMPLE 21C benzyl (1R)-1-(hydroxymethyl)-3-(4-morpholinyl)-3-oxopropylcarbamate A solution of EXAMPLE 21B (13.5 g, 57.4 mmol) and morpholine (10.0 mL, 115 mmol) in dioxane (100 mL) was stirred at 70° C. for 18 hours. The solution was concentrated and purified by silica gel chromatography eluting with 10% methanol/ethyl acetate to provide the desired product 6.0 g, 86%).

EXAMPLE 21D benzyl (1R)-3-(4-morpholinyl)-3-oxo-1-((phenylsulfanyl)methyl)propylcarbamate A solution of EXAMPLE 21C (16.5 g, 51.2 mmol), diphenyldisulfide (14.5 g, 66.5 mmol) and tributylphosphine (16.6 mL, 66.5 mmol) in toluene (250 mL) was heated to 80° C. for 24 hours, concentrated, and purified by silica gel chromatography eluting with 50% ethyl acetate/hexanes to provide a mixture of the desired product containing approximately 10% tributylphosphine oxide (18.0 g mixture, ~76%) that was carried on without further purification.

EXAMPLE 21E (1R)-3-(4-morpholinyl)-3-oxo-1-((phenylsulfanyl)methyl)propylamine A solution of EXAMPLE 21D (18.0 g, ~39 mmol) in 30% HBr in acetic acid (250 mL) was stirred for 24 hours at room temperature, concentrated to half its volume, poured into 1M HCl (300 mL), washed with diethyl ether (3×200 mL), and extracted with 1M HCl (150 mL). The combined aqueous layers were cooled to 0° C., adjusted to pH ~12 with solid KOH, and extracted with dichloromethane (5×100 mL). The combined extracts were washed with brine, dried ($Na_2SO_4$), filtered, and concentrated to provide the desired product (10.8 g, 98%).

EXAMPLE 21F (1R)-3-(4-morpholinyl)-1-((phenylsulfanyl)methyl)propylamine

A solution of EXAMPLE 21E (6.00 g, 21.4 mmol) in THF (80 mL) was heated to 55° C. and treated dropwise with a solution of 1M borane in THF (85 mL, 85.0 mmol) over a 1 hour period. The resulting reaction mixture was stirred at 55° C. for 18 hours, cooled to 0° C., treated dropwise with methanol (10 mL), treated with 150 mL additional methanol, and concentrated. The crude residue was dissolved in methanol (70 mL), treated with methanolic HCl (100 mL), and heated to reflux for 24 hours. The mixture was allowed to cool to room temperature, concentrated, diluted with 2M NaOH (200 mL), and extracted with ethyl acetate (3×250 mL). The combined extracts were washed with 1M NaOH and brine, dried ($Na_2SO_4$), filtered, concentrated, and purified by silica gel chromatography eluting with 5% triethylamine/10% methanol/0% acetonitrile/ethyl acetate to provide the desired product (3.45 g, 73%).

EXAMPLE 21G 4-(4-methoxy-4-(2-methylbenzyl)-1-piperidinyl)-N-((4-(((1R)-3-(4-morpholinyl)-1-((phenylsulfanyl)methyl)propyl)amino)-3-nitrophenyl)sulfonyl)benzenecarboximidamide The desired product was prepared by substituting EXAMPLE 21F and EXAMPLE 8D for EXAMPLE 1M and EXAMPLE 1I, respectively, in EXAMPLE 1N. MS (ESI) m/e 785 (M−H)$^-$; $^1$H NMR (500 MHz, $CDCl_3$) δ 8.65 (d, 1H), 8.21 (d, 1H), 8.12 (br, 1H), 7.83 (dd, 1H), 7.68 (d, 2H), 7.30 (m, 2H), 7.15 (m, 6H), 6.85 (d, 2H), 6.67 (d, 1H), 6.37 (br, 1H), 4.01 (br, 2H), 3.95 (br, 4H), 3.56 (d, 2H), 3.36 (s, 3H), 3.14 (m, 7H), 2.84 (s, 2H), 2.84 (br, 2H), 2.40 (m, 1H), 2.32 (s, 3H), 2.17 (m, 1H), 1.86 (d, 2H), 1.65 (m, 2H).

EXAMPLE 22

4-(4-((4'-chloro-1,1'-biphenyl-2-yl)methyl)-1-piperazinyl)-N-((3-nitro-4-((2-(phenylsulfanyl)ethyl)amino)phenyl)sulfonyl)benzenecarboximidamide

EXAMPLE 22A tert-butyl 4-(2-bromobenzyl)-1-piperazinecarboxylate

A solution of tert-butyl 1-piperazinecarboxylate (5.51 g, 29.623 mmol) in acetonitrile (60 mL) at 0° C. was treated with diisopropylethylamine and 2-bromobenzyl bromide (7.776 g, 31.105 mmol), warmed to room temperature, stirred for 2 hours, and concentrated. The residue was partitioned between ethyl acetate and aqueous $NaHCO_3$. The aqueous layer was extracted with ethyl acetate and the combined extracts were dried ($MgSO_4$), filtered, and concentrated. The concentrate was used directly in the next step without further purification.

EXAMPLE 22B tert-butyl 4-((4'-chloro-1,1'-biphenyl-2-yl)methyl)-1-piperazinecarboxylate A solution of EXAMPLE 22A (5.82 g, 16.394 mmol) in DME (80 mL) was treated with 4-chlorophenylboronic acid (3.089 g, 19.673 mmol), CsF (7.476 g, 49.182 mmol) and $(Ph_3P)_2Pd(OAc)_2$ (1.228 g, 1.639 mmol), heated to reflux for 4 hours, and filtered. The filtrate was partitioned between aqueous $NaHCO_3$ and ethyl acetate. The aqueous layer was extracted with ethyl acetate and the combined extracts were dried ($MgSO_4$), filtered, and concentrated. The residue was purified by silica gel column chromatography with 15% ethyl acetate/hexane to provide the desired product. MS (ESI) m/e 386, 388 (M+H)$^+$.

EXAMPLE 22C 1-((4'-chloro-1,1'-biphenyl-2-yl)methyl)piperazine

A solution of EXAMPLE 22B (1.00 g, 2.59 mmol) in dioxane (20 mL) at room temperature was treated with 4N HCl in dioxane (19.4 mL, 77.7 mmol), stirred overnight. Solvent was removed under reduced pressure. The residue was further dried under vacuum and used for the next step without further purification.

EXAMPLE 22D 4-(4-((4'-chloro-1,1'-biphenyl-2-yl)methyl)-1-piperazinyl)benzonitrile A solution of EXAMPLE 22C (932 mg, 2.591 mmol) in DMSO (13 mL) was treated with 4-fluorobenzonitrile (408 mg, 3.368 mmol) and $K_2CO_3$ (1.788 g, 12.955 mmol), heated at 130° C. for 4 hours, and filtered. The filtrate was partitioned between aqueous $NaHCO_3$ and ethyl acetate. The aqueous layer was extracted with ethyl acetate. The combined extracts were dried ($MgSO_4$), filtered, and concentrated. The residue was purified by silica gel column chromatography with 20% ethyl acetate/hexanes to provide the desired product. MS (ESI) m/e 388, 390 (M+H)$^+$.

EXAMPLE 22E 4-(4-((4'-chloro-1,1'-biphenyl-2-yl)methyl)-1-piperazinyl)benzenecarboximidamide The desired product was prepared by substituting EXAMPLE 22D for EXAMPLE 12A in EXAMPLE 12B.

EXAMPLE 22F 4-(4-((4'-chloro-1,1'-biphenyl-2-yl)methyl)-1-piperazinyl)-N-((4-fluoro-3-nitrophenyl)sulfonyl)benzenecarboximidamide The desired product was prepared by substituting EXAMPLE 22E for EXAMPLE 1H in EXAMPLE 1I. MS (ESI) m/e 608, 610 (M+H)$^+$.

EXAMPLE 22G 4-(4-((4'-chloro-1,1'-biphenyl-2-yl)methyl)-1-piperazinyl)-N-((3-nitro-4-((2-(phenylsulfanyl)ethyl)amino)phenyl)sulfonyl)benzenecarboximidamide The desired product was prepared by substituting EXAMPLE 22F and 2-phenylsulfanyl-ethylamine for EXAMPLE 1I and EXAMPLE 1M, respectively, in EXAMPLE 1N. MS (APCI) m/e 741, 743 (M+H)$^+$; $^1$H NMR (300 MHz, CDCl$_3$) δ 8.76 (d, 1H), 8.56 (t, 1H), 8.22 (br, 1H), 7.93 (dd, 1H), 7.77 (m, 1H), 7.68 (d, 2H), 7.45 (m, 4H), 7.26 (m, 7H), 6.77 (dd, 3H), 6.16 (br, 1H), 4.31 (s, 2H), 3.56 (q, 2H), 3.47 (br, 4H), 3.19 (t, 2H), 1.65 (br, 4H).

EXAMPLE 23

4-(4-((4'-chloro-1,1'-biphenyl-2-yl)methyl)-1-piperazinyl)-N-((4-(((1,1-dimethyl-2-(phenylsulfanyl)ethyl)amino)-3-nitrophenyl)sulfonyl)benzenecarboximidamide The desired product was prepared by substituting EXAMPLE 22F and 1,1-dimethyl-2-phenylsulfanylethylamine for EXAMPLE 1I and EXAMPLE 1M, respectively, in EXAMPLE 1N. MS (APCI) m/e 769, 771 (M+H); $^1$H NMR (300 MHz, CDCl$_3$) δ 8.84 (s, 1H), 8.46 (s, 1H), 8.39 (d, 1H), 8.04 (s, 1H), 7.81 (d, 2H), 7.75 (dd, 1H), 7.50 (m, 4H), 7.36 (m, 3H), 7.25 (m, 3H), 6.97 (m, 5H), 3.52 (s, 2H), 3.33 (m, 6H), 2.39 (m, 4H), 1.55 (s, 6H).

EXAMPLE 24

4-(4-((4'-chloro-1,1'-biphenyl-2-yl)methyl)-1-piperazinyl)-N-((4-(((1R)-3-(4-morpholinyl)-1-((phenylsulfanyl)methyl)propyl)amino)-3-nitrophenyl)sulfonyl)benzenecarboximidamide The desired product was prepared by substituting EXAMPLE 22F and EXAMPLE 21D for EXAMPLE 1I and EXAMPLE 1M, respectively, in EXAMPLE 1N. MS (ESI) m/e 852, 854 (M−H)$^-$; $^1$H NMR (300 MHz, CDCl$_3$) δ 8.72 (d, 1H), 8.50 (d, 1H), 8.21 (br, 1H), 7.82 (dd, 1H), 7.69 (d, 2H), 7.49 (m, 1H), 7.28 (m, 11H), 6.81 (d, 2H), 6.71 (d, 1H), 6.08 (br, 1H), 4.00 (br, 1H), 3.67 (s, 4H), 3.41 (s, 2H), 3.26 (t, 4H), 3.12 (t, 2H), 2.43 (m, 10H), 2.14 (m, 1H), 1.77 (m, 1H).

EXAMPLE 25

4-(4-(1,1'-biphenyl-2-ylmethyl)-4-methoxy-1-piperidinyl)-N-((3-nitro-4-((2-(phenylsulfanyl)ethyl)amino)phenyl)sulfonyl)benzenecarboximidamide

EXAMPLE 25A 4-(4-(2-bromobenzyl)-4-hydroxy-1-piperidinyl)benzonitrile

The desired product was prepared by substituting 2-bromobenzylmagnesium bromide for benzylmagnesium chloride in EXAMPLE 5A. MS (ESI) m/e 371, 373 (M+H)$^+$.

EXAMPLE 25B 4-(4-(2-bromobenzyl)-4-methoxy-1-piperidinyl)benzonitrile

The desired product was prepared by substituting EXAMPLE 25A for EXAMPLE 1C in EXAMPLE 1D. MS (ESI) m/e 385, 387 (M+H)$^+$.

EXAMPLE 25C 4-(4-(1,1'-biphenyl-2-ylmethyl)-4-methoxy-1-piperidinyl)benzonitrile The desired product was prepared by substituting EXAMPLE 25B and phenylboronic acid for EXAMPLE 22A and 4-chlorophenylboronic acid, respectively, in EXAMPLE 22B. MS (ESI) m/e 383 (M+H)$^+$.

EXAMPLE 25D 4-(4-(1,1'-biphenyl-2-ylmethyl)-4-methoxy-1-piperidinyl)benzenecarboximidamide The desired product was obtained by substituting EXAMPLE 25C for EXAMPLE 12A in EXAMPLE 12B.

EXAMPLE 25E 4-(4-(1,1'-biphenyl-2-ylmethyl)-4-methoxy-1-piperidinyl)-N-((4-fluoro-3-nitrophenyl)sulfonyl)benzenecarboximidamide The desired product was obtained by substituting EXAMPLE 25D for EXAMPLE 1H in EXAMPLE 1I. MS (ESI) m/e 603 (M+H)$^+$.

EXAMPLE 25F 4-(4-(1,1'-biphenyl-2-ylmethyl)-4-methoxy-1-piperidinyl)-N-((3-nitro-4-((2-(phenylsulfanyl)ethyl)amino)phenyl)sulfonyl)benzenecarboximidamide The desired product was prepared by substituting EXAMPLE 25E and 2-phenylsulfanyl-ethylamine for EXAMPLE 1I and EXAMPLE 1M, respectively in EXAMPLE 1N. MS (ESI) m/e 731 (M−H); $^1$H NMR (500 MHz, CDCl$_3$) δ 8.75 (d, 1H), 8.53 (t, 1H), 8.15 (br, 1H), 7.93 (dd, 1H), 7.65 (d, 2H), 7.40 (m, 3H), 7.27 (m, 10H), 6.81 (d, 2H), 6.77 (d, 1H), 6.21 (br, 1H), 3.55 (q, 2H), 3.35 (d, 2H), 3.18 (t, 2H), 3.12 (s, 3H), 2.99 (m, 2H), 2.94 (s, 2H), 1.59 (d, 2H), 1.40 (m, 2H).

EXAMPLE 26

4-(4-(1,1'-biphenyl-2-ylmethyl)-4-methoxy-1-piperidinyl)-N-((4-((1,1-dimethyl-2-(phenylsulfanyl)ethyl)amino)-3-nitrophenyl)sulfonyl)benzenecarboximidamide The desired product was prepared by substituting EXAMPLE 25E and 1,1-dimethyl-2-phenylsulfanylethylamine for EXAMPLE 1I and EXAMPLE 1M, respectively in EXAMPLE 1N. MS (ESI) m/e 762 (M−H)$^-$; $^1$H NMR (500 MHz, CDCl$_3$) δ 8.65 (d, 1H), 8.18 (br, 1H), 7.81 (dd, 1H), 7.67 (d, 2H), 7.37 (m, 3H), 7.27 (m, 8H), 7.03 (m, 3H), 6.94

(d, 1H), 6.78 (d, 2H), 6.14 (br, 1H), 3.35 (br, 4H), 3.12 (s, 3H), 2.97 (t, 2H), 2.94 (s, 2H), 1.59 (s, 6H), 1.57 (br, 2H), 1.36 (br, 2H).

EXAMPLE 27

4-(4-(1,1'-biphenyl-2-ylmethyl)-4-methoxy-1-piperidinyl)-N-((4-(((1R)-3-(4-morpholinyl)-1-((phenylsulfanyl)methyl)propyl)amino)-3-nitrophenyl)sulfonyl)benzenecarboximidamide The desired product was prepared by substituting EXAMPLE 25E and EXAMPLE 21D for EXAMPLE 1I and EXAMPLE 1M, respectively in EXAMPLE 1N. MS (ESI) m/e 847 (M−H)−; $^1$H NMR (500 MHz, CDCl$_3$) δ 8.64 (d, 1H), 8.21 (d, 1H), 8.12 (br, 1H), 7.83 (dd, 1H), 7.67 (d, 2H), 7.39 (t, 2H), 7.29 (m, 8H), 7.20 (m, 3H), 6.85 (d, 2H), 6.67 (d, 1H), 6.38 (br, 1H), 3.99 (br, 6H), 3.35 (d, 2H), 3.15 (m, 8H), 3.02 (m, 2H), 2.94 (s, 2H), 2.82 (br, 2H), 2.40 (m, 1H), 2.18 (m, 1H), 1.60 (d, 2H), 1.41 (m, 2H).

EXAMPLE 28

4-(4-(1,1'-biphenyl-2-ylmethylene)-1-piperidinyl)-N'-((3-nitro-4-((2-(phenylsulfanyl)ethyl)amino)phenyl)sulfonyl)benzenecarboximidamide

EXAMPLE 28A 4-(4-(1,1'-biphenyl-2-ylmethylene)-1-piperidinyl) benzonitrile

The desired product was prepared by substituting biphenyl-2-ylmethyl triphenylphosphonium bromide (prepared according to the procedure described in J. Org. Chem. 2000, 65, 543-577) for 4-fluorobenzyl triphenylphosphonium chloride in EXAMPLE 9A. MS (ESI) m/e 351 (M+H)$^+$.

EXAMPLE 28B 4-(4-(1,1'-biphenyl-2-ylmethylene)-1-piperidinyl) benzenecarboximidamide The desired product was prepared by substituting EXAMPLE 28A for EXAMPLE 12A in EXAMPLE 12B. MS (DCI) m/e 368 (M+H)$^+$.

EXAMPLE 28C 4-(4-(1,1'-biphenyl-2-ylmethylene)-1-piperidinyl)-N'-((4-fluoro-3-nitrophenyl)sulfonyl)benzenecarboximidamide The desired product was prepared by substituting EXAMPLE 28B for EXAMPLE 1H in EXAMPLE 1I. MS (ESI) m/e 571 (M+H)$^+$.

EXAMPLE 28D 4-(4-(1,1'-biphenyl-2-ylmethylene)-1-piperidinyl)-N'-((3-nitro-4-((2-(phenylsulfanyl)ethyl)amino)phenyl)sulfonyl)benzenecarboximidamide The desired product was prepared by substituting EXAMPLE 28C and 2-phenylsulfanyl-ethylamine for EXAMPLE 1I and EXAMPLE 1M, respectively, in EXAMPLE 1N. MS (ESI) m/e 702 (M−H)−; $^1$H NMR (400 MHz, DMSO-d$_6$) δ 8.78 (s, 1H), 8.64 (t, 1H), 8.48 (d, 1H), 7.98 (s, 1H), 7.85 (dd, 1H), 7.77 (d, 2H), 7.33 (m, 11H), 7.28 (m, 2H), 7.15 (m, 2H), 6.92 (d, 2H), 6.17 (s, 1H), 3.63 (m, 2H), 3.40 (t, 2H), 3.26 (t, 2H), 3.21 (t, 2H), 2.25 (t, 4H).

EXAMPLE 29

4-(4-(1,1'-biphenyl-2-ylmethylene)-1-piperidinyl)-N'-((4-((1,1-dimethyl-2-(phenylsulfanyl)ethyl) amino)-3-nitrophenyl)sulfonyl)benzenecarboximidamide The desired product was prepared by substituting EXAMPLE 28C and 1,1-dimethyl-2-phenylsulfanylethylamine for EXAMPLE 1I and EXAMPLE 1M, respectively, in EXAMPLE 1N. MS (ESI) m/e 73) (M−H)−; $^1$H NMR (400 MHz, DMSO-d$_6$) δ 8.80 (s, 1H), 8.65 (s, 1H), 8.39 (d, 1H), 8.02 (s, 1H), 7.81 (d, 2H), 7.75 (dd, 10H), 7.35 (m, 10H), 7.24 (m, 3H), 7.01 (m, 2H), 6.94 (d, 2H), 6.16 (s, 1H), 3.52 (s, 2H), 3.40 (t, 2H), 3.22 (t, 2H), 2.26 (t, 4H), 1.55 (s, 6H).

EXAMPLE 30

4-(4-(1,1'-biphenyl-2-ylmethylene)-1-piperidinyl)-N'-((4-(((1R)-3-(4-morpholinyl)-1-((phenylsulfanyl) methyl)propyl)amino)-3-nitrophenyl)sulfonyl)benzenecarboximidamide The desired product was prepared by substituting EXAMPLE 28C and EXAMPLE 21D for EXAMPLE 1I and EXAMPLE 1M, respectively, in EXAMPLE 1N. MS (ESI) m/e 815 (M−H)−; $^1$H NMR (400 MHz, DMSO-d$_6$) δ 8.77 (s, 1H), 8.43 (d, 1H), 8.38 (d, 1H), 7.98 (s, 1H), 7.77 (m, 3H), 7.33 (m, 11H), 7.13 (m, 4H), 6.93 (d, 2H), 6.16 (s, 1H), 4.15 (m, 1H), 3.48 (m, 4H), 3.40 (t, 2H), 3.35 (t, 2H), 3.28 (t, 2H), 3.21 (t, 2H), 2.28 (m, 6H), 2.18 (m, 2H), 1.98 (m, 1H), 1.90 (m, 1H).

EXAMPLE 31

N'-((3-nitro-4-((2-(phenylsulfanyl)ethyl)amino)phenyl)sulfonyl)-4-(4-(2-(trifluoromethyl)benzylidene)-1-piperidinyl)benzenecarboximidamide The desired product was prepared by substituting EXAMPLE 10C and 2-phenylsulfanyl-ethylamine for EXAMPLE 1I and EXAMPLE 1M, respectively, in EXAMPLE 1N. MS (ESI) m/e 693 (M−H)−; $^1$H NMR (400 MHz, DMSO-d$_6$) δ 8.80 (s, 1H), 8.65 (t, 1H), 8.48 (d, 1H), 8.01 (s, 1H), 7.85 (dd, 1H), 7.79 (d, 2H), 7.72 (d, 1H), 7.63 (m, 1H), 7.47 (m, 1H), 7.35 (m, 3H), 7.26 (m, 2H), 7.15 (m, 2H), 6.97 (d, 2H), 6.50 (s, 1H), 3.64 (m, 2H), 3.51 (t, 2H), 3.38 (t, 2H), 3.26 (t, 2H), 2.42 (t, 2H), 2.24 (t, 2H).

EXAMPLE 32

N'-((4-((1,1-dimethyl-2-(phenylsulfanyl)ethyl) amino)-3-nitrophenyl)sulfonyl)-4-(4-(2-(trifluoromethyl)benzylidene)-1-piperidinyl)benzenecarboximidamide The desired product was prepared by substituting EXAMPLE 10C and 1,1-dimethyl-2-phenylsulfanylethylamine for EXAMPLE 1I and EXAMPLE 1M, respectively, in EXAMPLE 1N. MS (ESI) m/e 722 (M−H)−; $^1$H NMR (400 MHz, DMSO-d$_6$) δ 8.83 (s, 1H), 8.46 (s, 1H), 8.39 (d, 1H), 8.04 (s, 1H), 7.84 (d, 2H), 7.75 (m, 2H), 7.63 (m, 1H), 7.46

(m, 1H), 7.34 (m, 2H), 7.23 (d, 2H), 6.97 (m, 5H), 6.50 (s, 1H), 3.52 (m, 4H), 3.38 (t, 2H), 2.43 (t, 2H), 2.25 (t, 4H), 1.55 (s, 6H).

EXAMPLE 33

N'-((4-(((1R)-3-(4-morpholinyl)-1-((phenylsulfanyl) methyl)propyl)amino)-3-nitrophenyl)sulfonyl)-4-(4-(2-(trifluoromethyl)benzylidene)-1-piperidinyl)benzenecarboximidamide The desired product was prepared by substituting EXAMPLE 10C and EXAMPLE 21D for EXAMPLE 1I and EXAMPLE 1M, respectively, in EXAMPLE 1N. MS (ESI) m/e 806 (M−H)⁻; $^1$H NMR (400 MHz, DMSO-$d_6$) δ 8.79 (s, 1H), 8.43 (d, 1H), 8.38 (d, 1H), 8.00 (s, 1H), 7.77 (m, 4H), 7.63 (m, 1H), 7.47 (m, 1H), 7.36 (m, 1H), 7.27 (m, 2H), 7.13 (m, 4H), 6.97 (d, 2H), 6.49 (s, 1H), 4.15 (m, 1H), 3.49 (m, 6H), 3.38 (m, 4H), 2.42 (t, 2H), 2.25 (m, 8H), 1.96 (m, 1H), 1.89 (m, 1H).

EXAMPLE 34

4-(4-(3,3-diphenyl-2-propenyl)-1-piperazinyl)-N'-((3-nitro-4-((2-(phenylsulfanyl)ethyl)amino)phenyl) sulfonyl)benzenecarboximidamide

EXAMPLE 34A 4-(4-(3,3-diphenyl-2-propenyl)-1-piperazinyl)-N'-((4-fluoro-3-nitrophenyl)sulfonyl)benzenecarboximidamide The desired compound was prepared by substituting EXAMPLE 12B for EXAMPLE 1H in EXAMPLE 1I. MS (ESI) m/e 600 (M+H)⁺.

EXAMPLE 34B 4-(4-(3,3-diphenyl-2-propenyl)-1-piperazinyl)-N'-((3-nitro-4-((2-(phenylsulfanyl)ethyl)amino)phenyl) sulfonyl)benzenecarboximidamide The desired product was prepared by substituting EXAMPLE 34A and 2-phenylsulfanyl-ethylamine for EXAMPLE 1I and EXAMPLE 1M, respectively, in EXAMPLE 1N. MS (ESI) m/e 731 (M−H)⁻; $^1$H NMR (400 MHz, DMSO-$d_6$) δ 8.78 (s, 1H), 8.64 (t, 1H), 8.48 (d, 1H), 8.01 (s, 1H), 7.85 (dd, 1H), 7.75 (d, 2H), 7.40-7.10 (m, 16H), 6.97 (d, 2H), 6.18 (t, 1H), 3.64 (m, 2H), 3.27 (m, 6H), 3.01 (d, 2H), 2.44 (t, 4H).

EXAMPLE 35

N'-((4-((1,1-dimethyl-2-(phenylsulfanyl)ethyl) amino)-3-nitrophenyl)sulfonyl)-4-(4-(3,3-diphenyl-2-propenyl)-1-piperazinyl)benzenecarboximidamide The desired product was prepared by substituting EXAMPLE 34A and 1,1-dimethyl-2-phenylsulfanylethylamine for EXAMPLE 1I and EXAMPLE 1M, respectively, in EXAMPLE 1N. MS (ESI) m/e 759 (M−H); $^1$H NMR (400 MHz, DMSO-$d_6$) δ 8.83 (s, 1H), 8.45 (s, 1H), 8.39 (d, 1H), 8.04 (s, 10H), 7.81 (d, 2H), 7.75 (dd, 10H), 7.43-7.20 (m, 12H), 7.13 (d, 2H), 6.97 (m, 4H), 6.19 (t, 1H), 3.51 (s, 2H), 3.30 (m, 4H), 3.01 (d, 2H), 2.45 (t, 4H), 1.55 (s, 6H).

EXAMPLE 36

4-(4-(3,3-diphenyl-2-propenyl)-1-piperazinyl)-N'-((4-(((1R)-3-(4-morpholinyl)-1-((phenylsulfanyl) methyl)propyl)amino)-3-nitrophenyl)sulfonyl)benzenecarboximidamide The desired product was prepared by substituting EXAMPLE 34A and EXAMPLE 21D for EXAMPLE 1I and EXAMPLE 1M, respectively, in EXAMPLE 1N. MS (ESI) m/e 844 (M−H)⁻; $^1$H NMR (400 MHz, DMSO-$d_6$) δ 8.79 (s, 1H), 8.43 (d, 1H), 8.38 (d, 1H), 8.00 (s, 1H), 7.77 (m, 3H), 7.45-7.10 (m, 16H), 6.92 (d, 2H), 6.19 (t, 1H), 4.15 (m, 1H), 3.47 (m, 4H), 3.38 (m, 2H), 3.29 (m, 4H), 3.01 (d, 2H), 2.45 (m, 4H), 2.31 (m, 4H), 2.18 (m, 2H), 1.96 (m, 1H), 1.81 (m, 1H).

Following the procedures described in the EXAMPLEs and the schemes, the following compounds may be prepared:

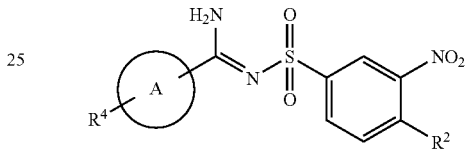

wherein $R^2$ is one of the following structures:

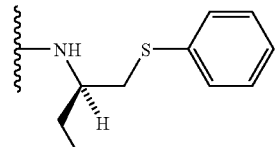

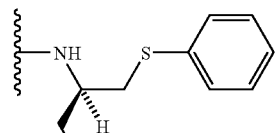

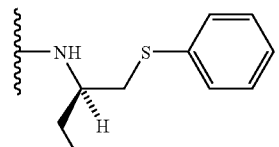

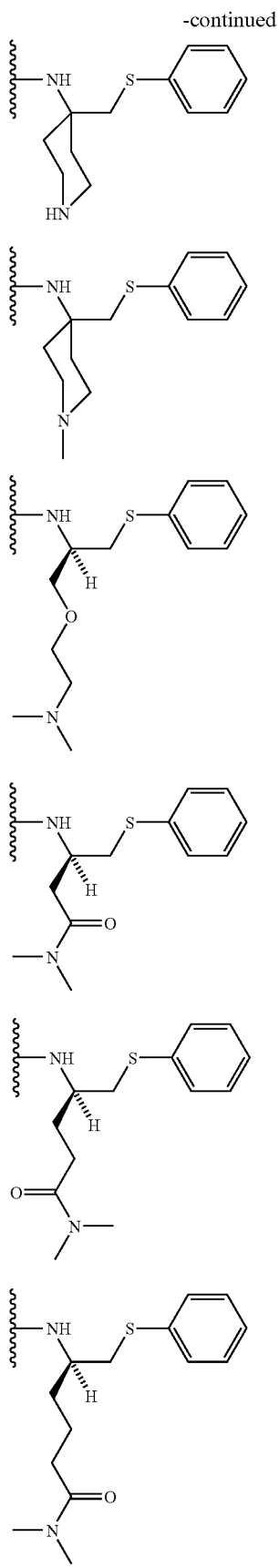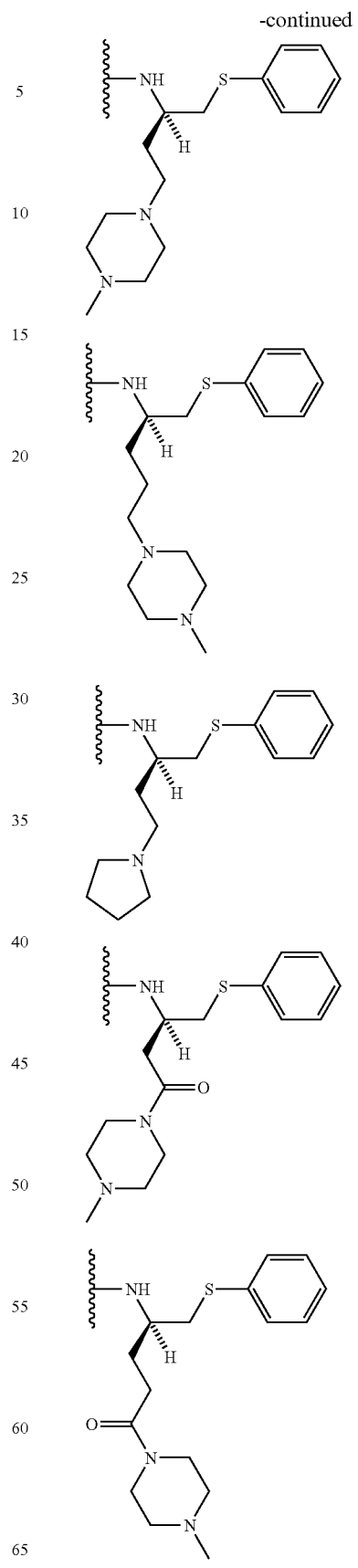

-continued
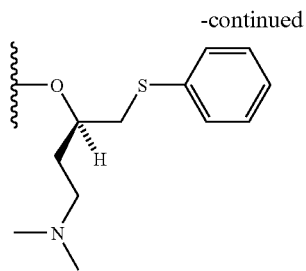
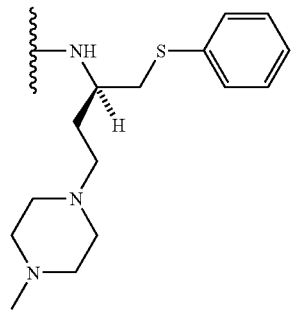
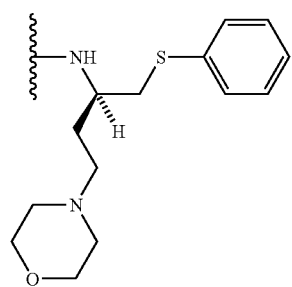
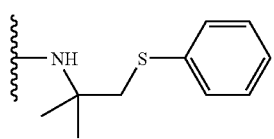
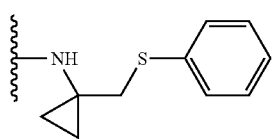
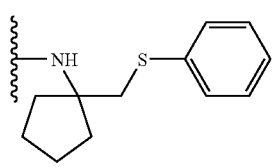
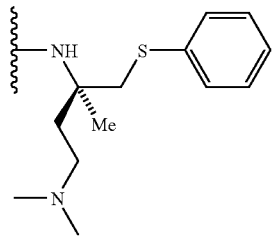
-continued
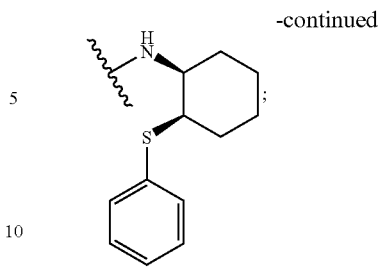
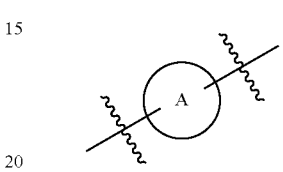
is one of the following structures:
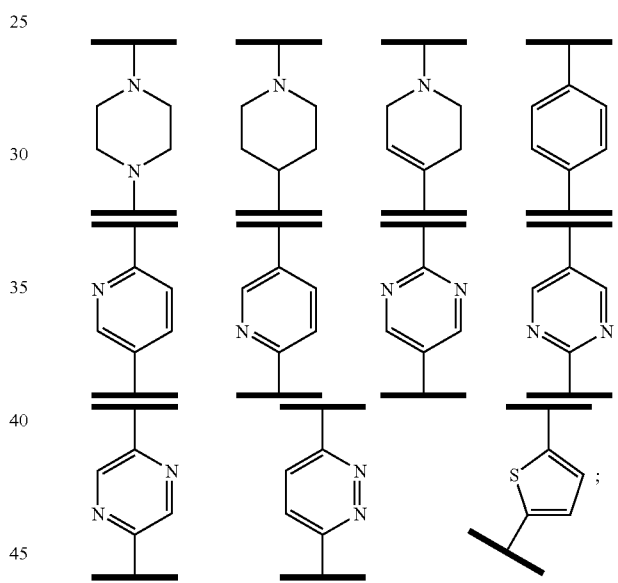
and
$R^4$ is one of the following structures:
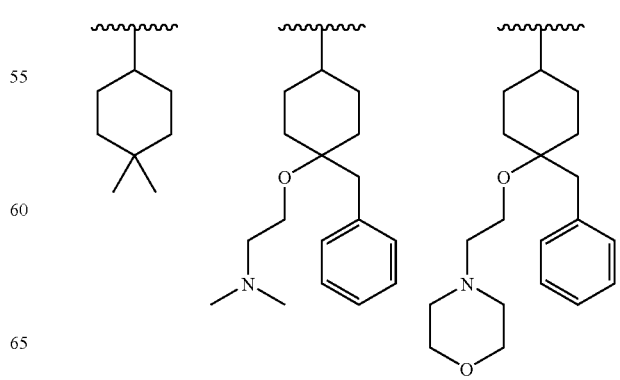

-continued
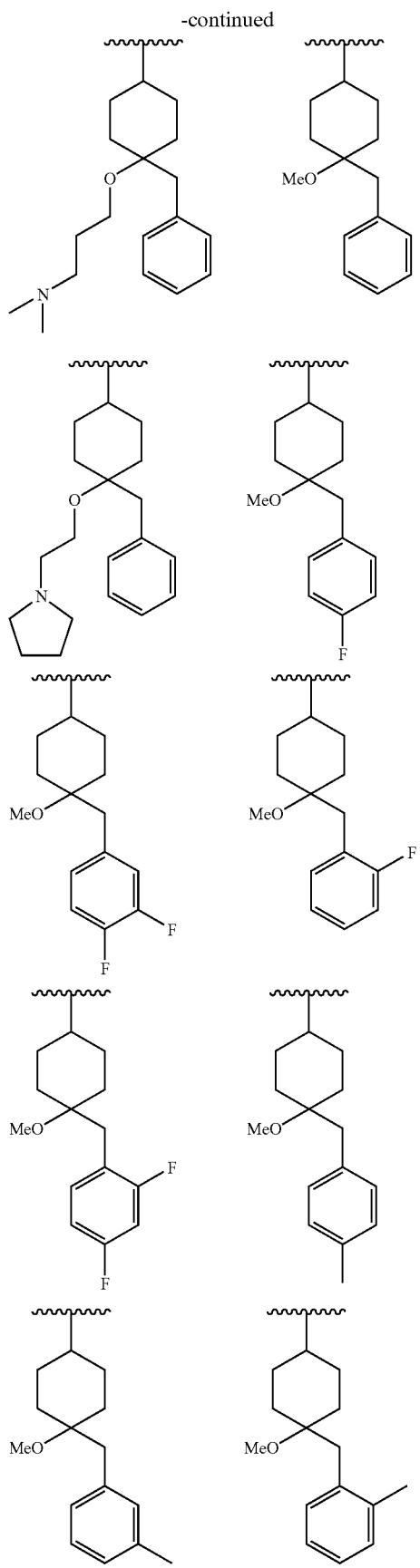
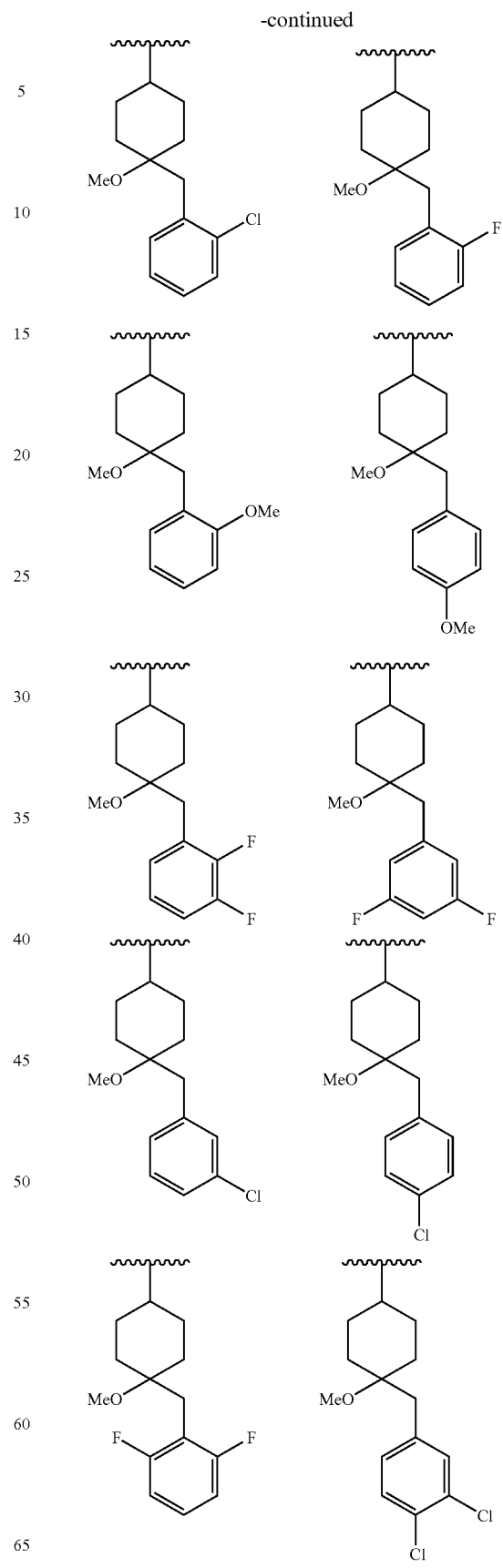

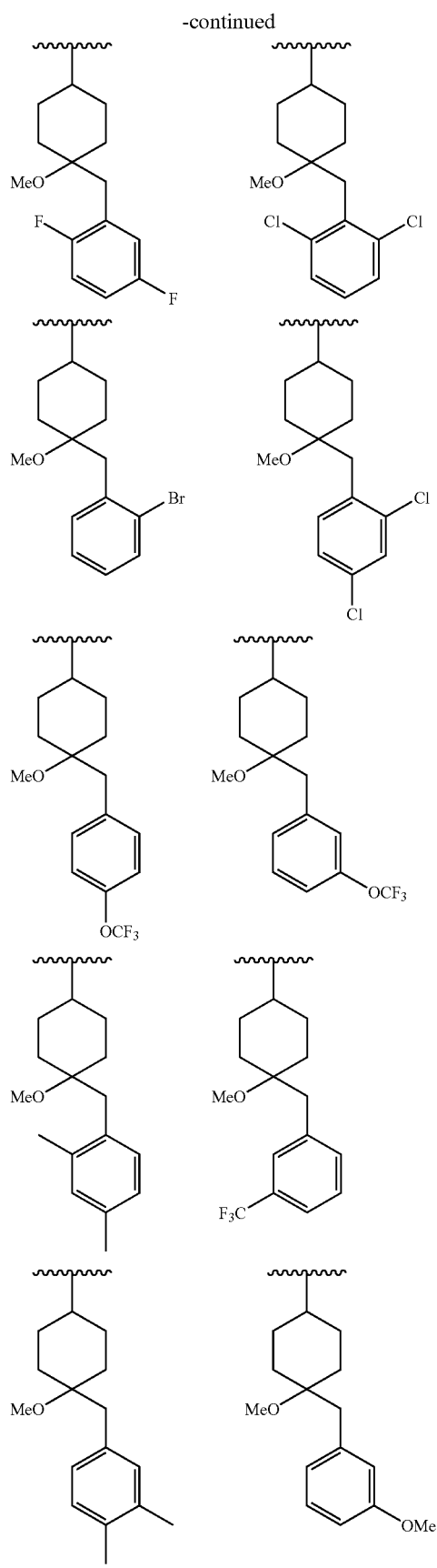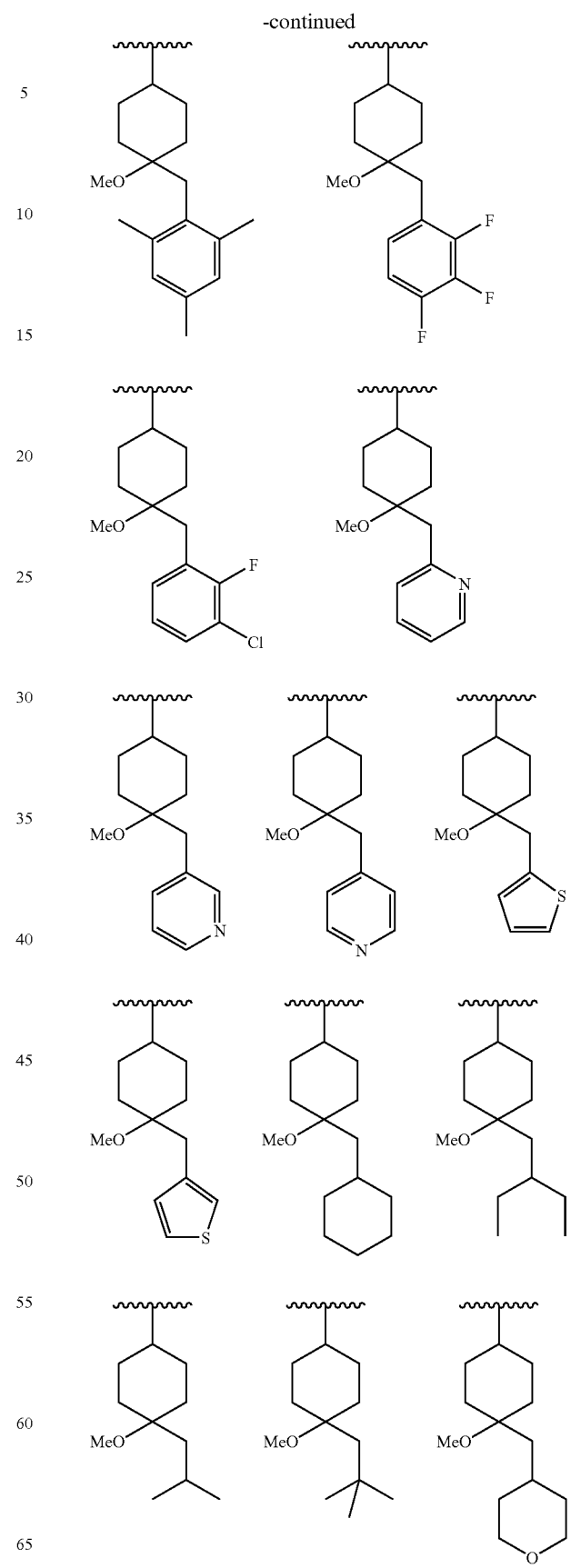

-continued
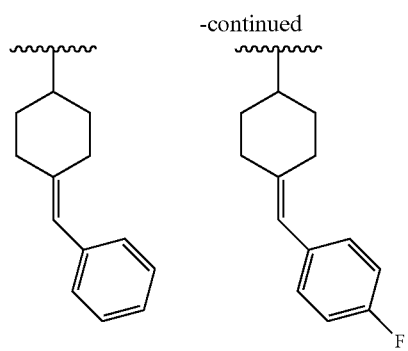
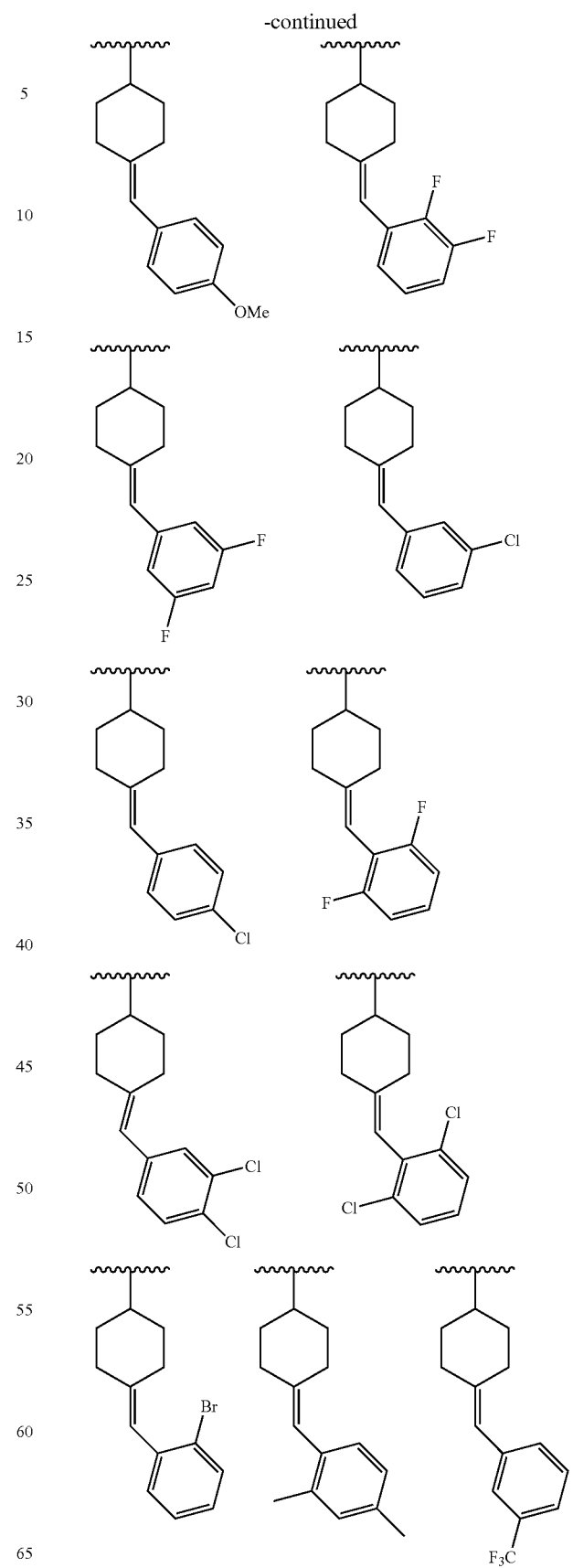

-continued
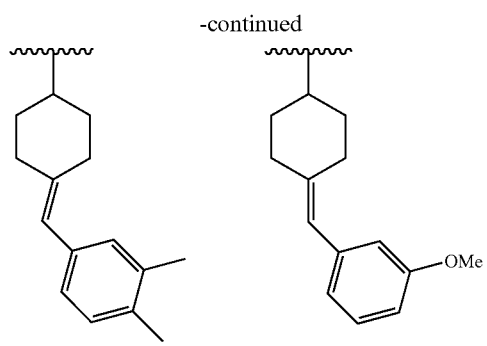
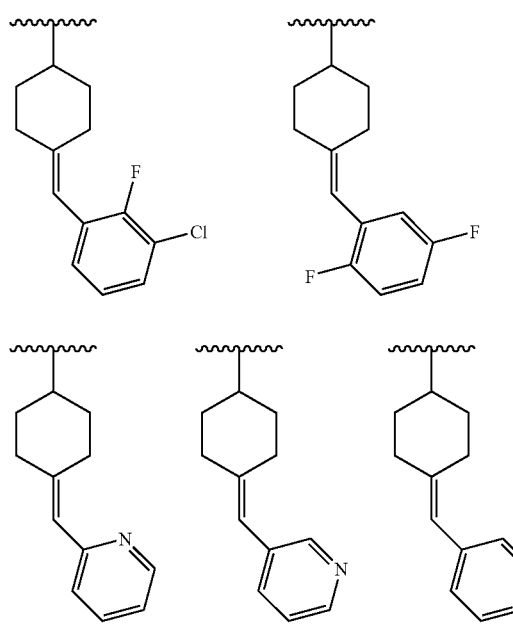
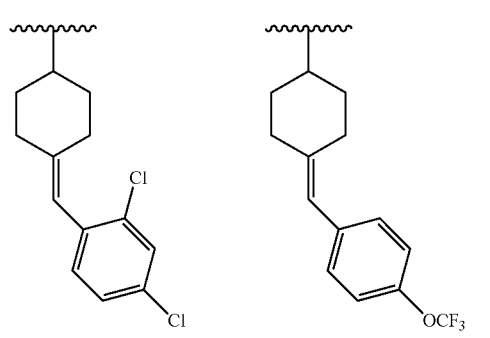
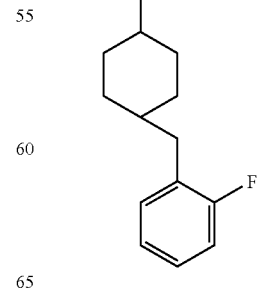
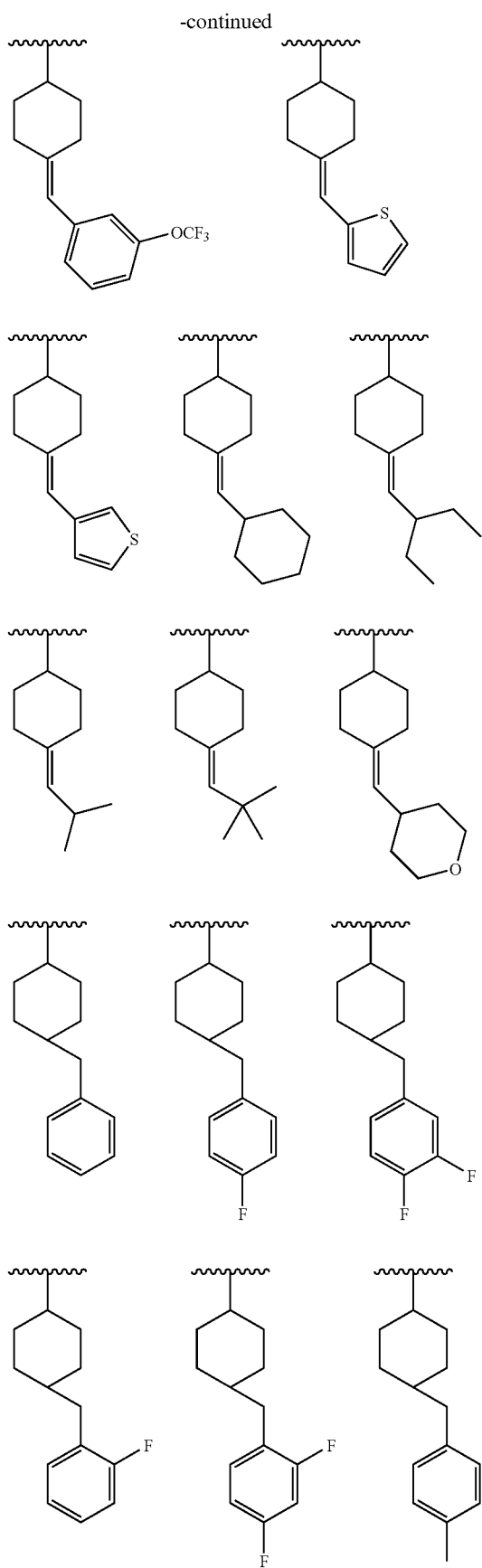

-continued
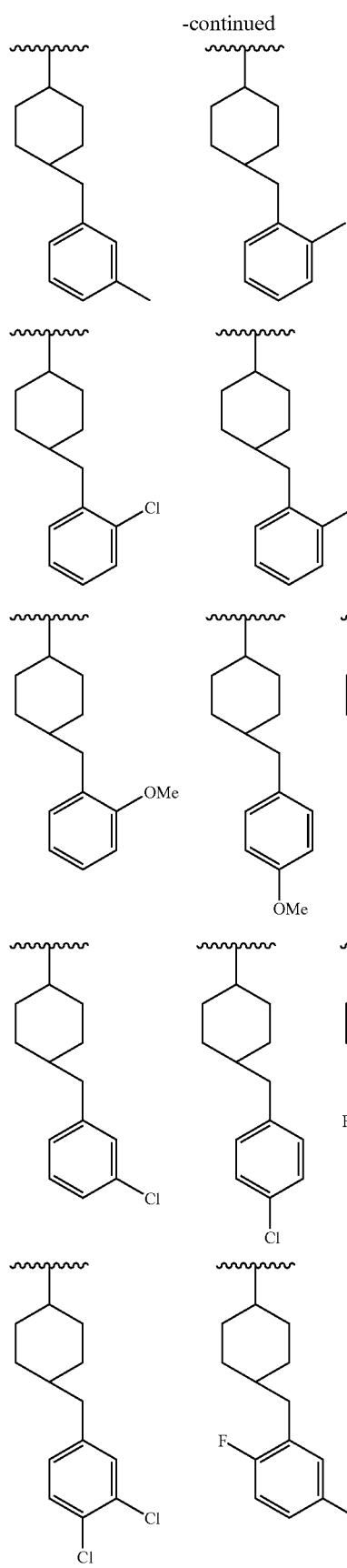
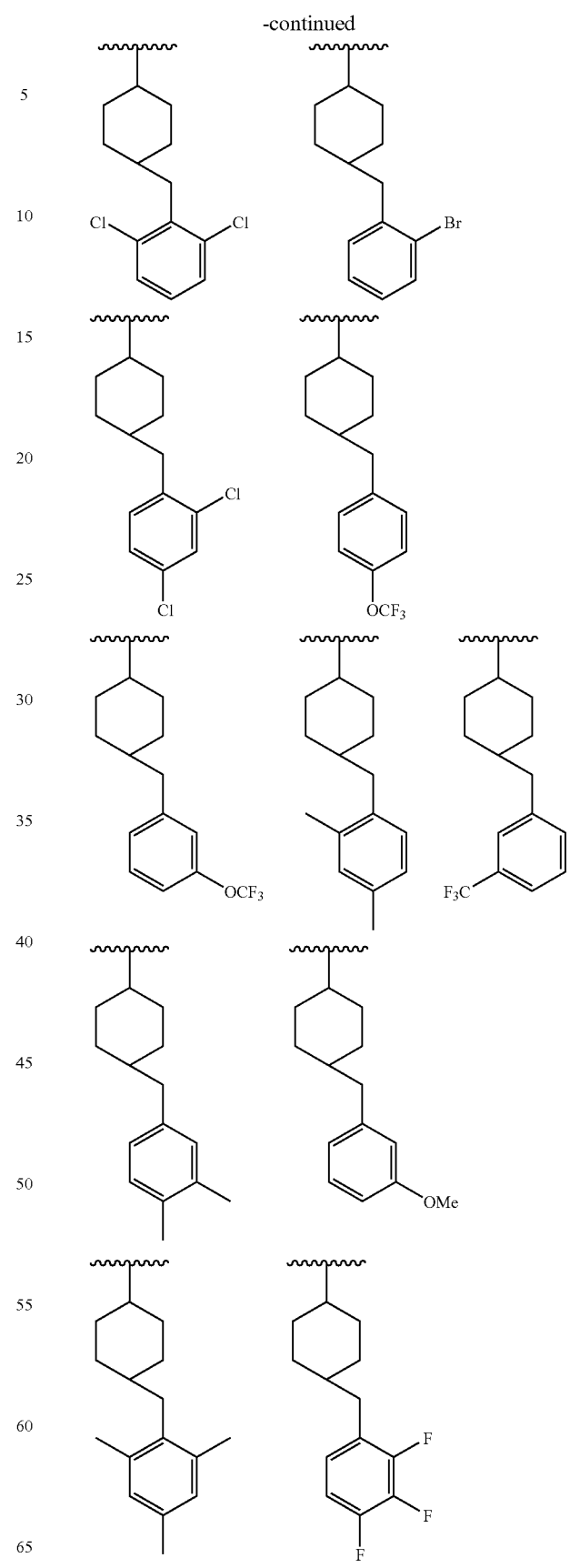

-continued
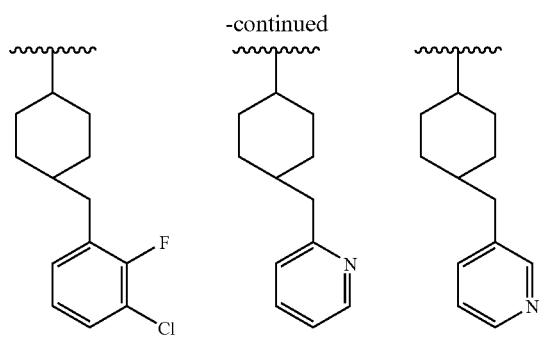
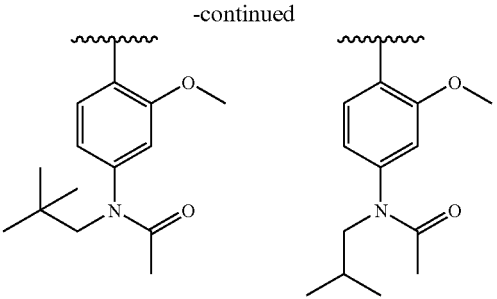
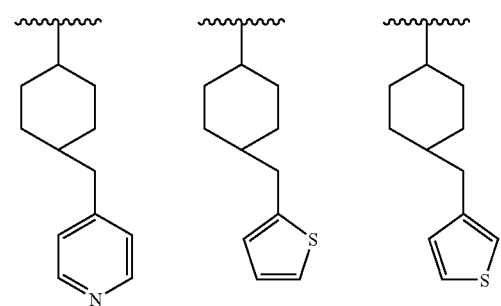
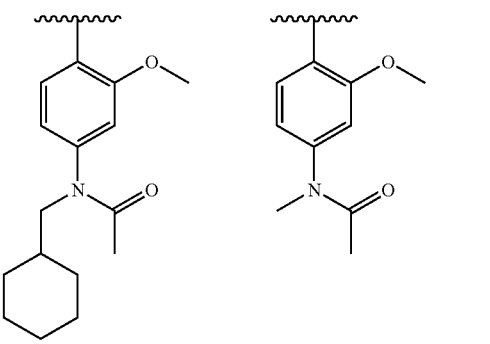
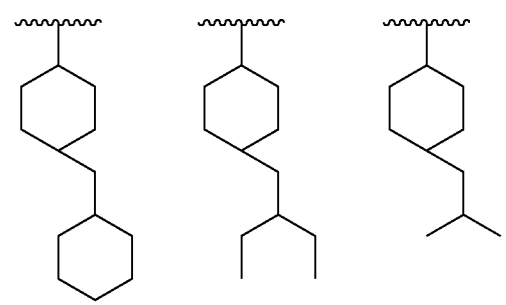
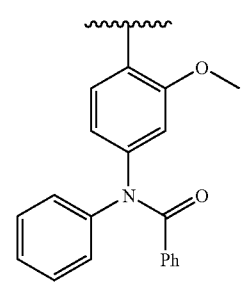
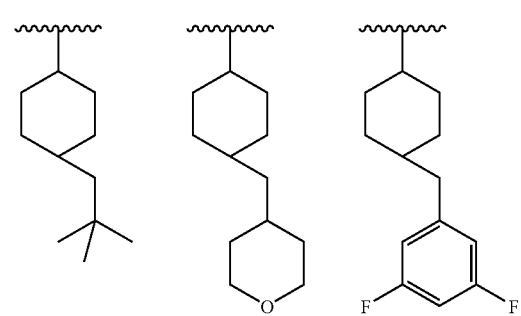
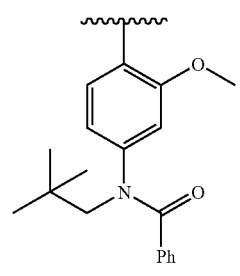
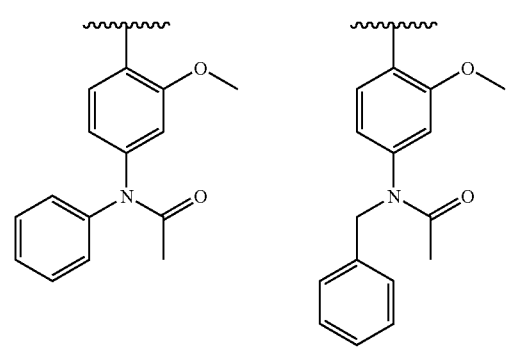
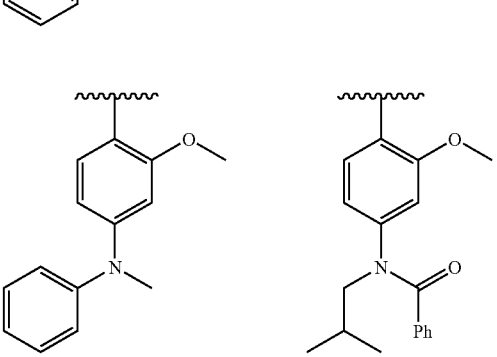

-continued
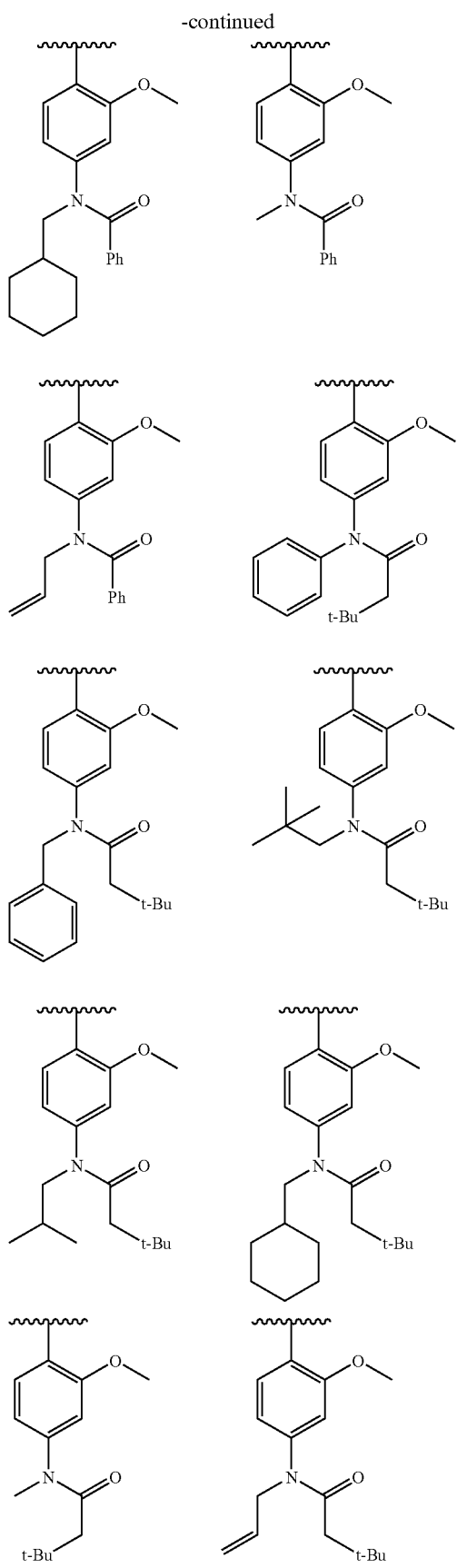
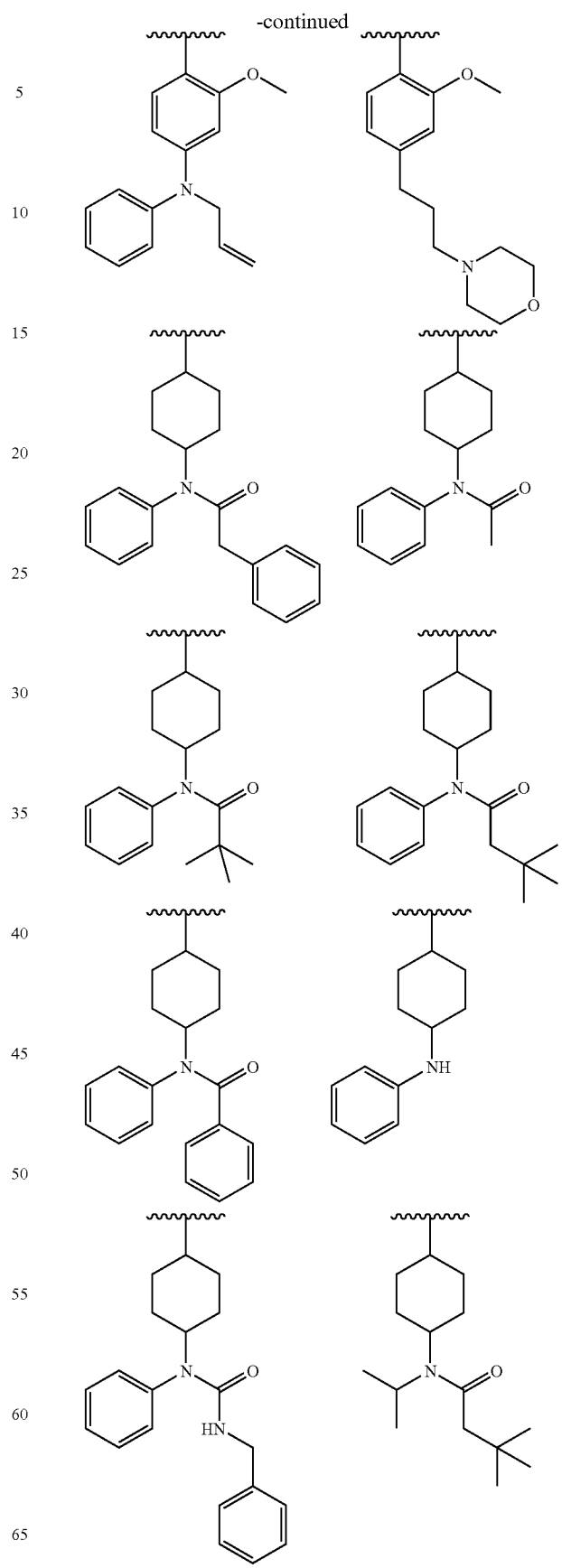

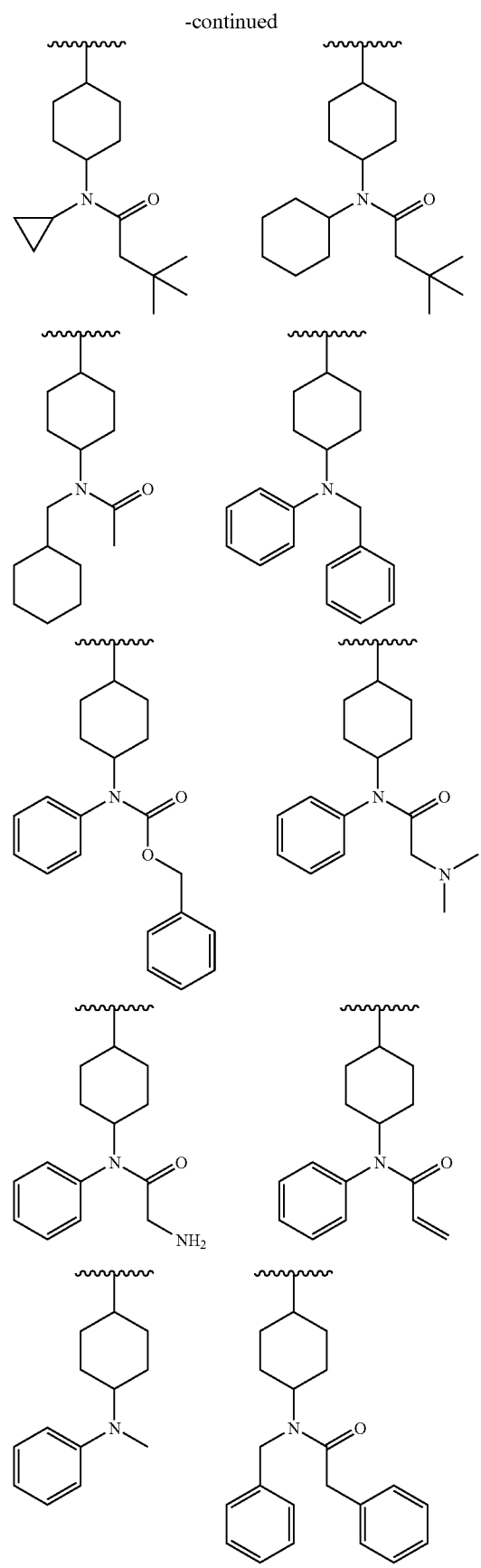
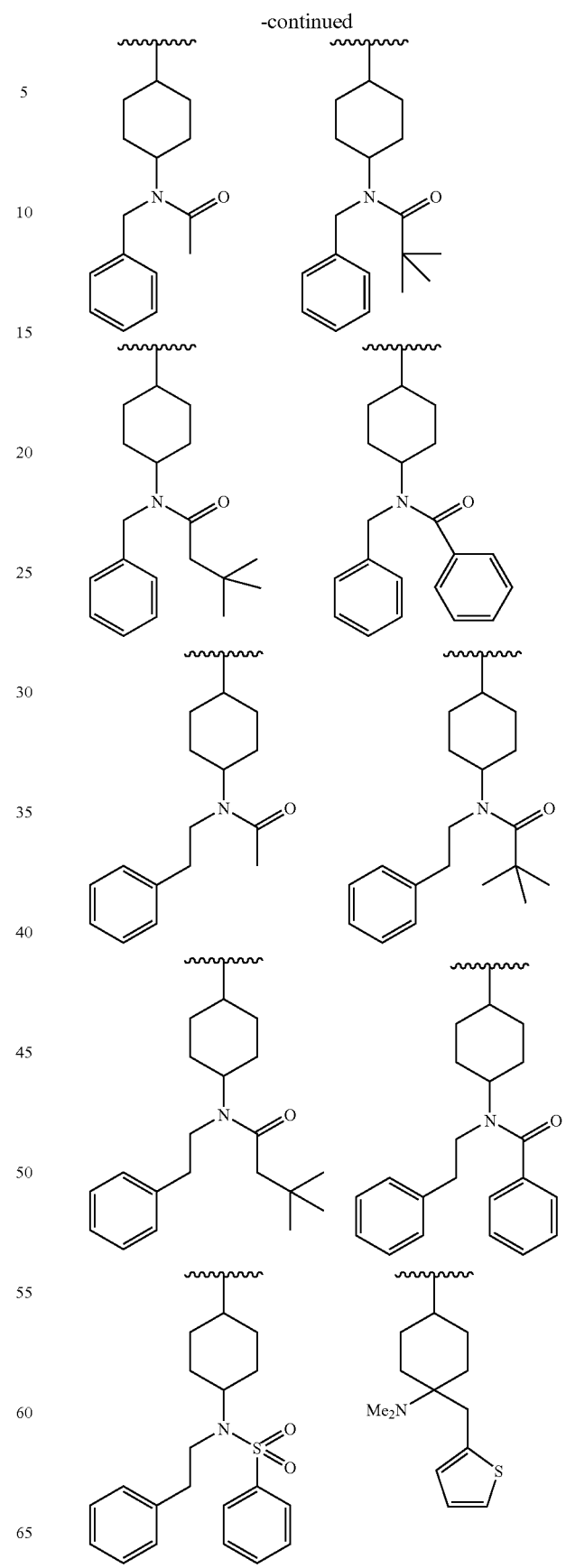

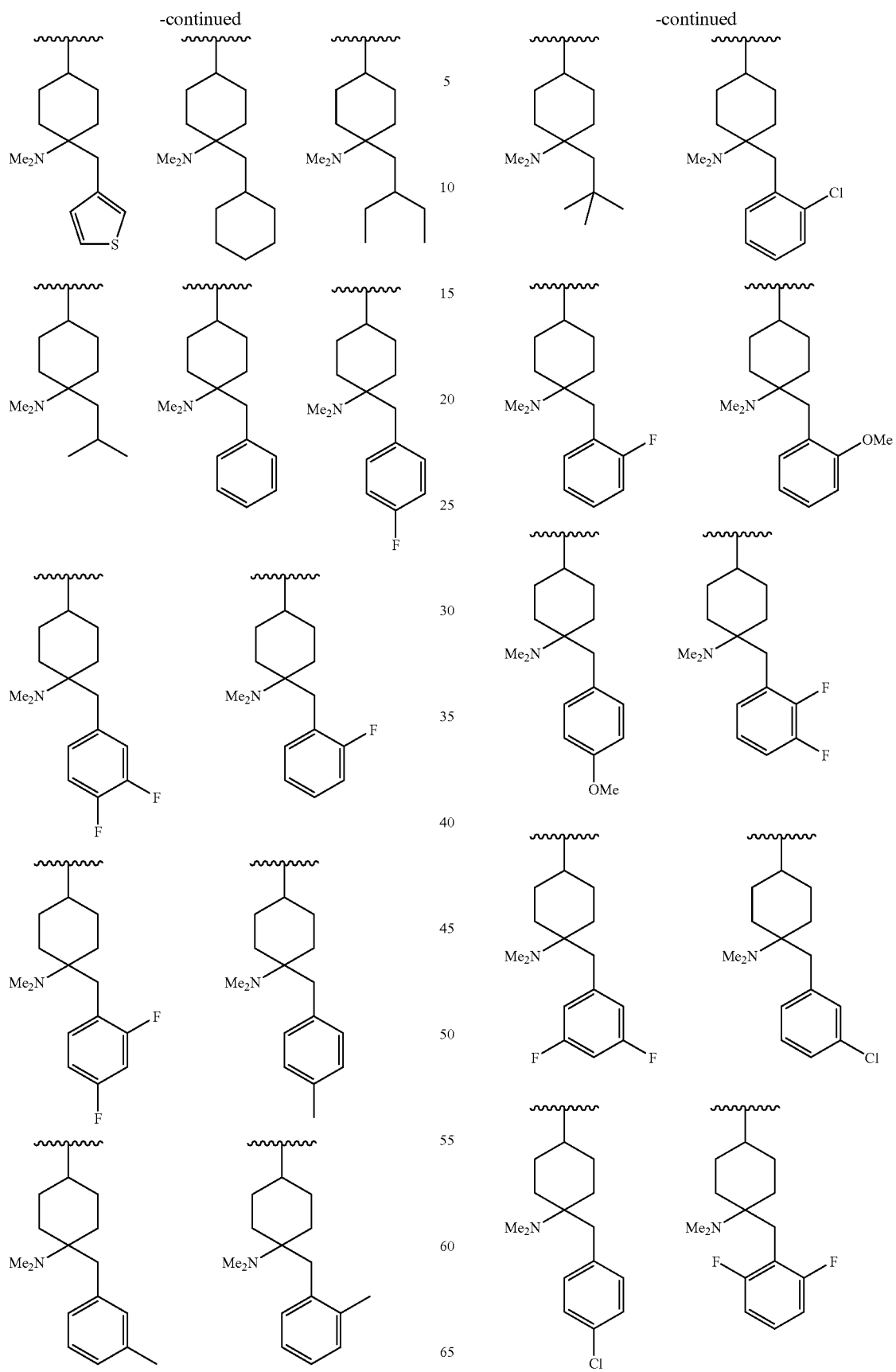

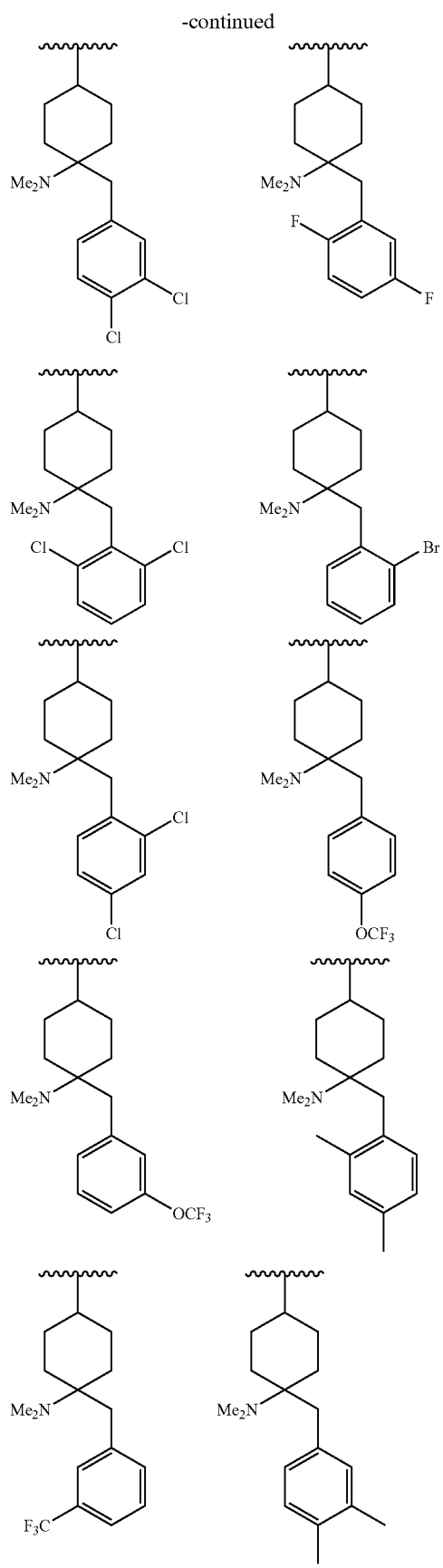
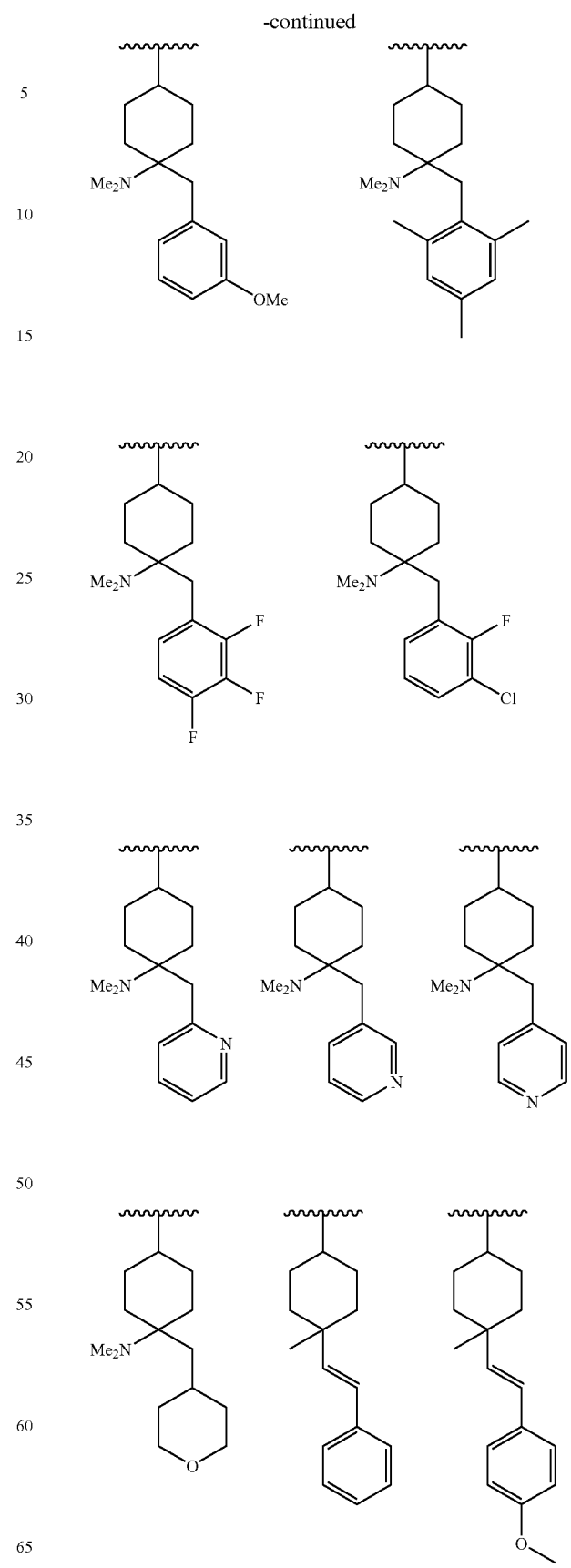

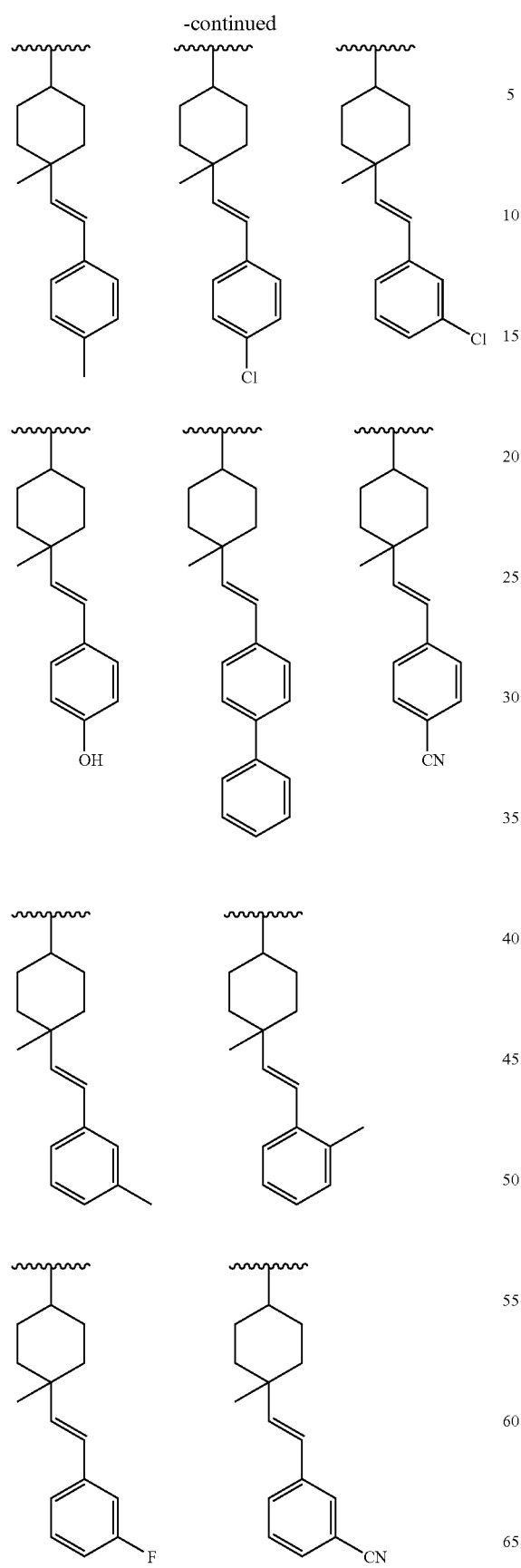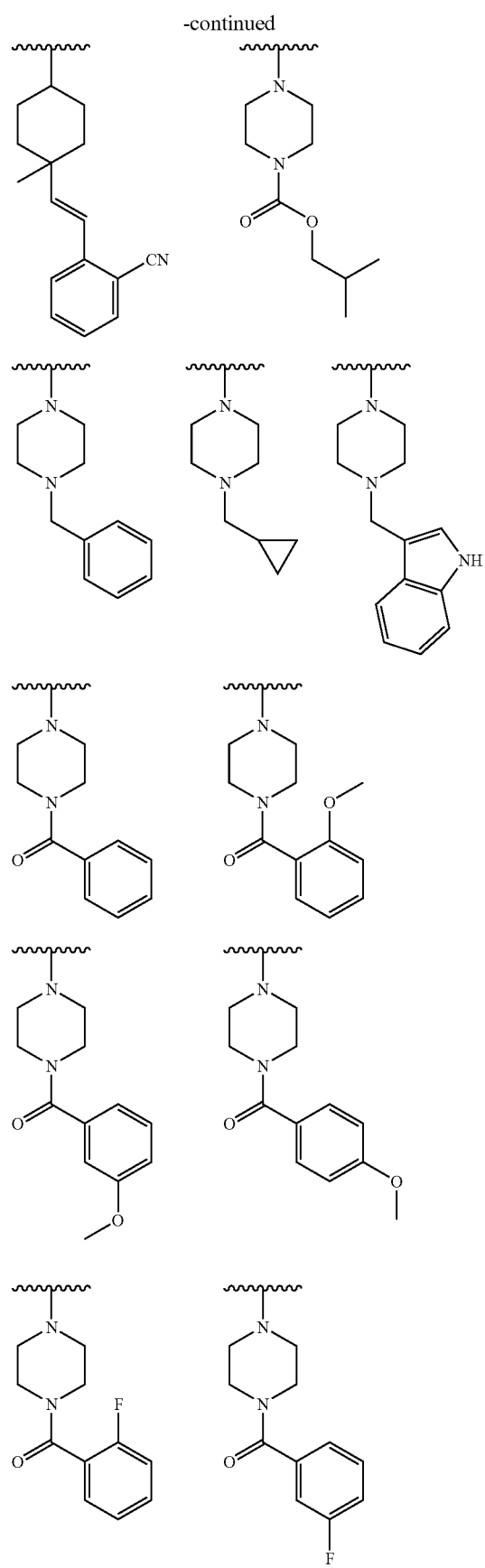

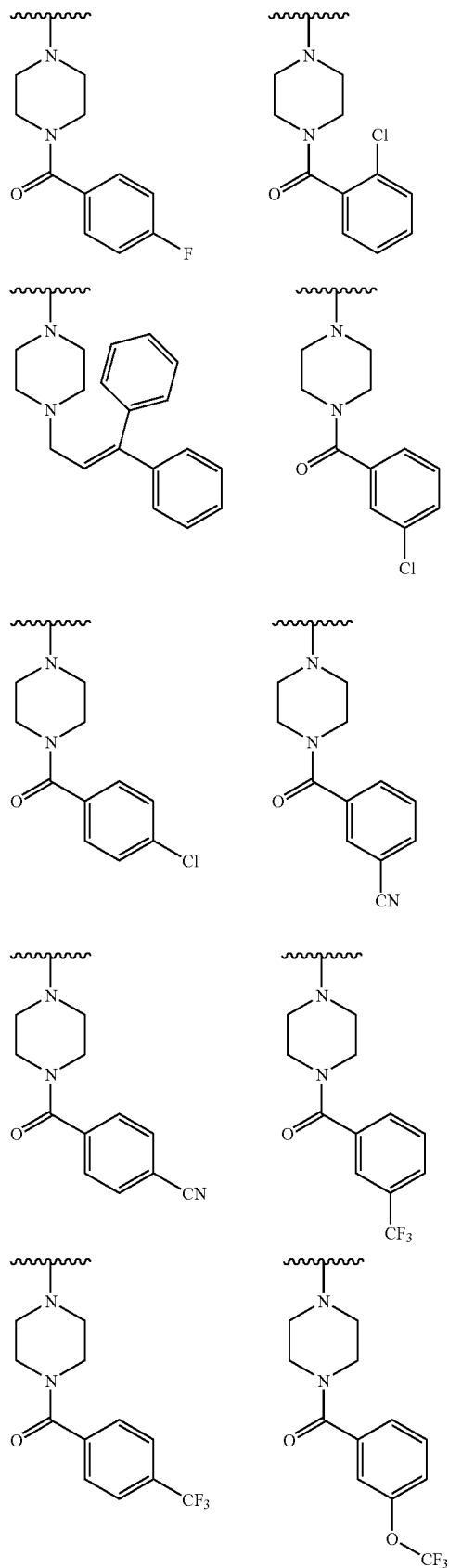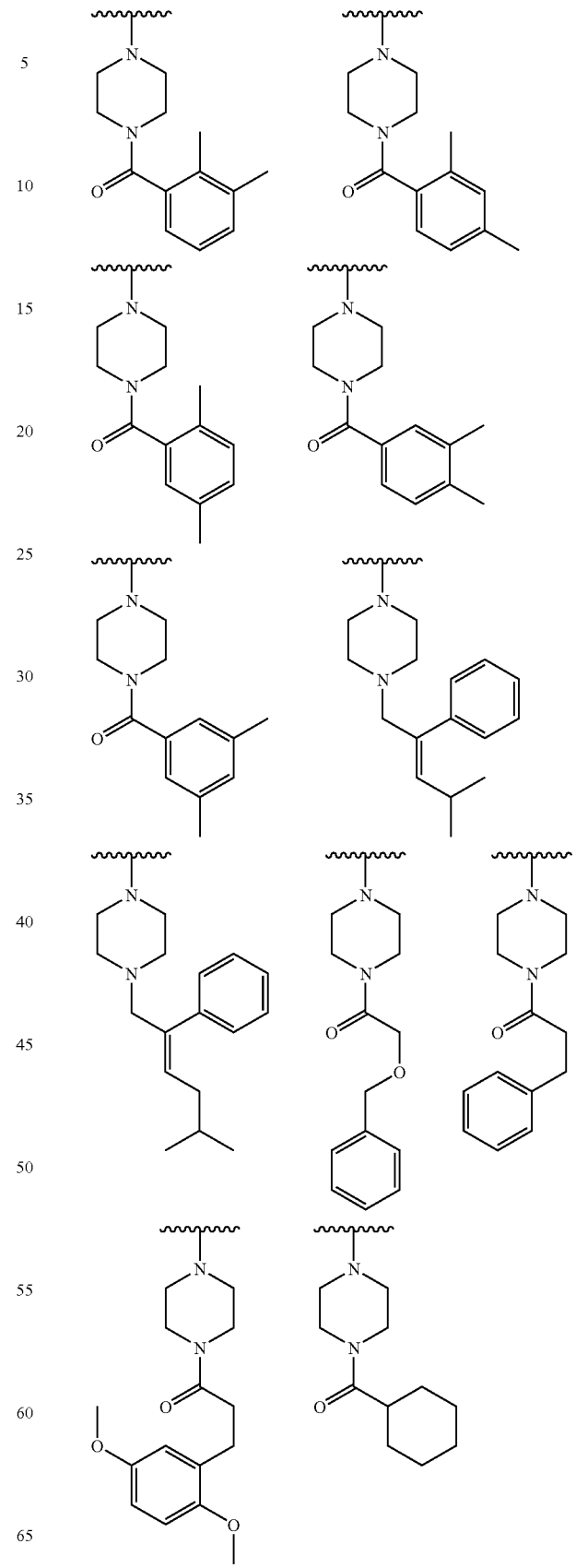

75
-continued
76
-continued
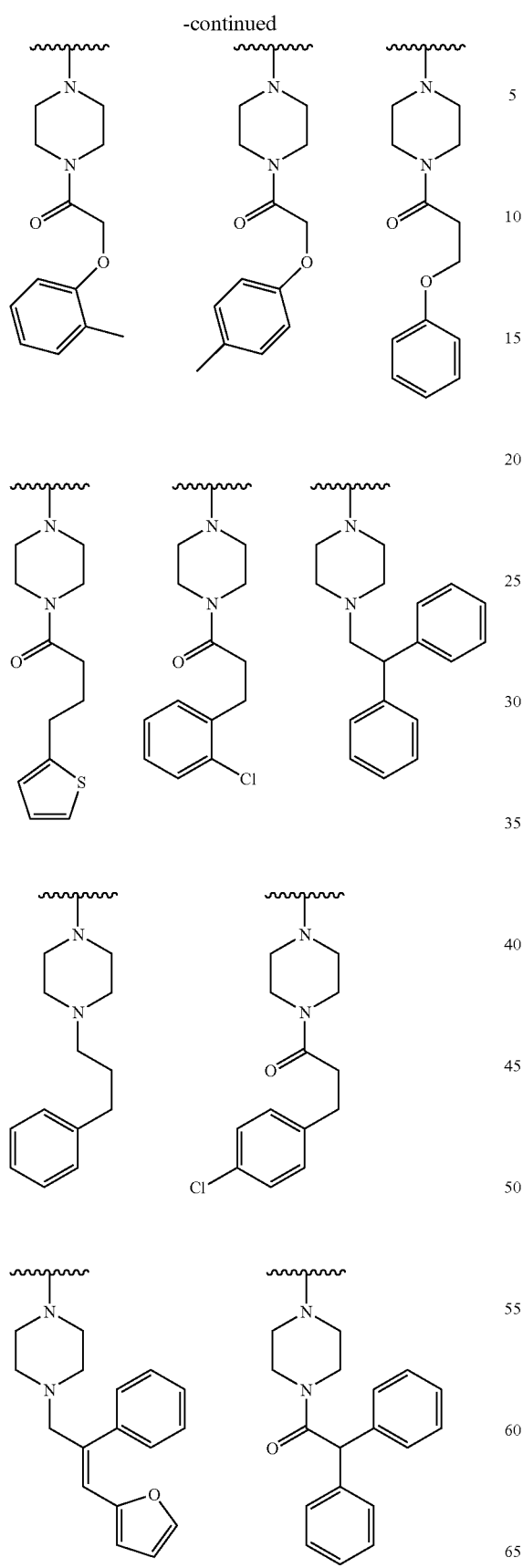
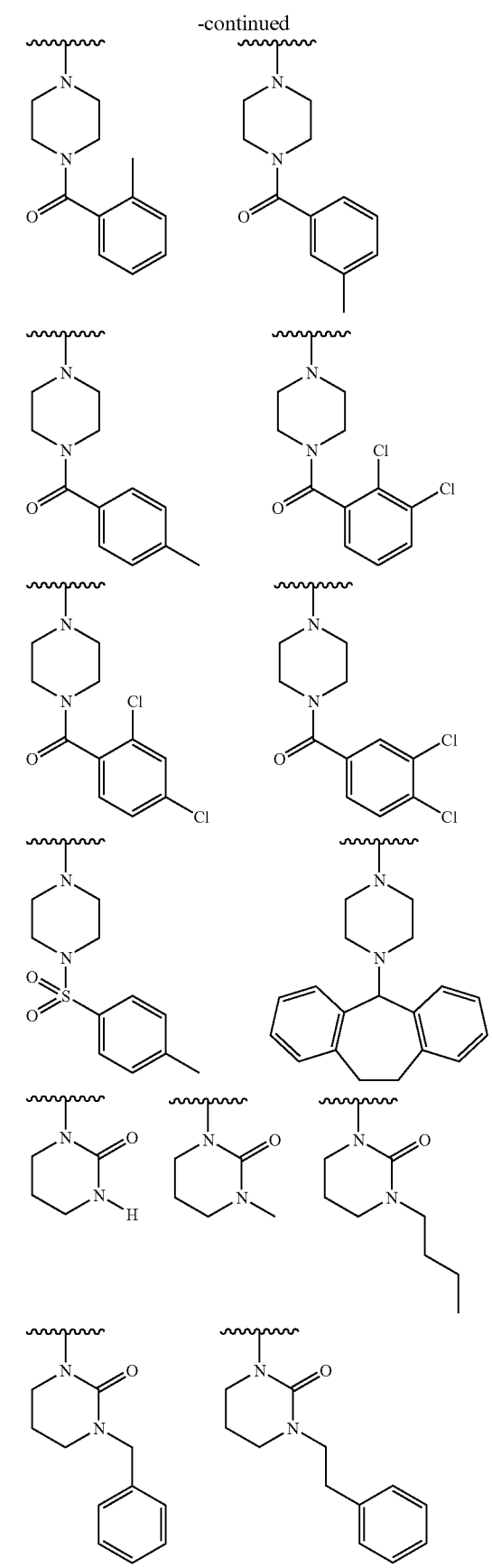

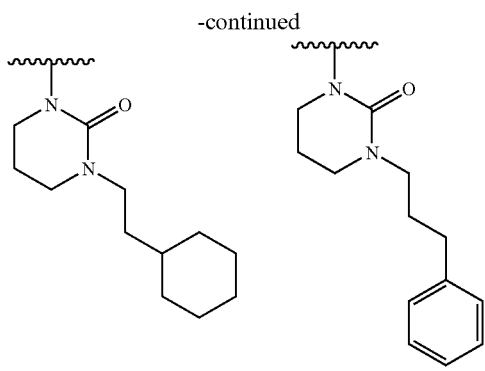
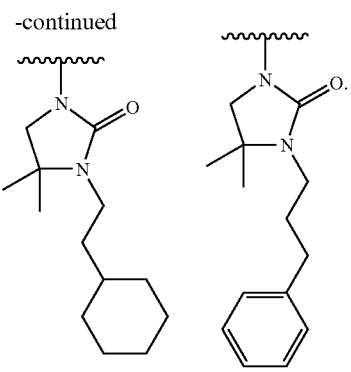
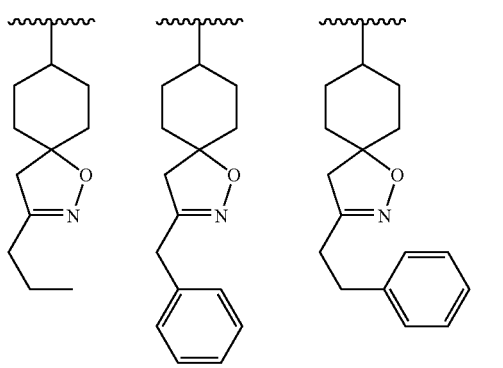

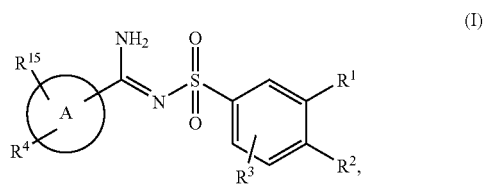

What is claimed is:
1. A compound of formula (I)

$$\text{(I)}$$

or a therapeutically acceptable salt thereof, wherein
A is phenyl;
$R^1$ is selected from the group consisting of alkyl, cyano, halo, haloalkyl and nitro;
$R^2$ is —$NR^5R^6$;
$R^3$ is hydrogen;
$R^4$ is piperidinyl;
$R^5$ is hydrogen and and $R^6$ is arylsulfanylalkyl, the alkyl part of which can be further optionally substituted with morpholinyl or $NR^aR^b$, wherein $R^a$ and $R^b$ are alkyl; and
$R^{15}$ is selected from the group consisting of hydrogen, alkoxy, alkyl, and halo.
2. The compound of claim 1 wherein $R^{15}$ is hydrogen.
3. A compound selected from the group consisting of
N-((4-(((1R)-3-(dimethylamino)-1-((phenylsulfanyl)methyl)propyl)amino)-3-nitrophenyl)sulfonyl)-4-(4-(2-fluorobenzyl)-4-methoxy-1-piperidinyl)benzenecarboximidamide;
N-((4-(((1R)-3-(dimethylamino)-1-((phenylsulfanyl)methyl)propyl)amino)-3-nitrophenyl)sulfonyl)-4-(4,4-dimethyl-1-piperidinyl)benzenecarboximidamide;
N((4-(((1R)-5-(dimethylamino)-1-(phenylsulfanyl)methyl)pentyl)amino)-3-nitrophenyl)sulfonyl)-4-(4,4-dimethyl-1-piperidinyl)benzenecarboximidamide;
4-(4,4-dimethyl-1-piperidinyl)-N-((3-nitro-4-((2-(phenylsulfanyl)ethyl)amino)phenyl)sulfonyl)benzenecarboximidamide;
4-(4-benzyl-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide;
4-(4-(cyclohexylmethyl)-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide;

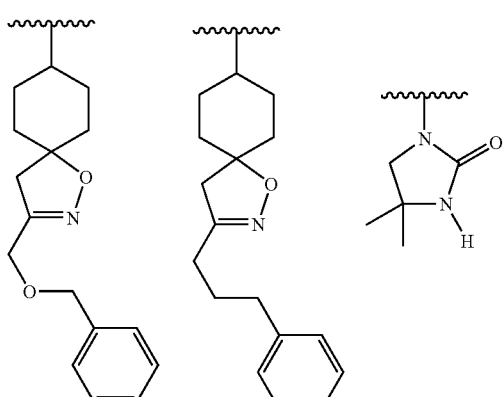
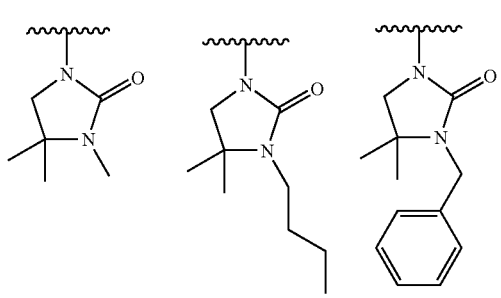

4-(4-(2,4-difluorobenzyl)-4-methoxy-1-piperidinyl)-N-((4-(((1R)-3-(dimethylamino)-1-((phenylsulfanyl)methyl)propyl)amino)-3-nitrophenyl)sulfonyl)benzenecarboximidamide;

N-((4(((1R)-3-(dimethylamino)-1-(phenylsulfanyl)methyl)propyl)amino)-3-nitrophenyl)sulfonyl)-4-(4-methoxy-4-(2-methylbenzyl)-1-piperidinyl)benzenecarboximidamide;

N-((4-(((1R)-3-(dimethylamino)-1-(phenylsulfanyl)methyl)propyl)amino)-3-nitrophenyl)sulfonyl)-4-(4-(4-fluorobenzylidene)-1-piperidinyl)benzenecarboximidamide;

N-((4-(((1R)-3-(dimethylamino)-1-((phenylsulfanyl)methyl)propyl)amino)-3-nitrophenyl)sulfonyl)-4-(4-(2-(trifluoromethyl)benzylidene)-1-piperidinyl)benzenecarboximidamide;

N-((4-(((1R)-3-(dimethylamino)-1-((phenylsulfanyl)methyl)propyl)amino)-3-nitrophenyl)sulfonyl)-4-(4-(3-thienylmethylene)-1-piperidinyl)benzenecarboximidamide;

4-(4-methoxy-4-(2-methylbenzyl)-1-piperidinyl)-N-((3-nitro-4-((2-(phenylsulfanyl)ethyl)amino)phenyl)sulfonyl)benzenecarboximidamide;

N-((4-((1,1-dimethyl-2-(phenylsulfanyl)ethyl)amino)-3-nitrophenyl)sulfonyl)-4-(4-methoxy-4-(2-methylbenzyl)-1-piperidinyl)benzenecarboximidamide;

4-(4-methoxy-4-(2-methylbenzyl)-1-piperidinyl)-N-((4-(((1R)-3-(4-morpholinyl) 1((phenylsulfanyl)methyl)propyl)amino)-3-nitrophenyl)sulfonyl)benzenecarboximidamide;

4-(4-(1,1'-biphenyl-2-ylmethyl)-4-methoxy-1-piperidinyl)-N-((3-nitro-4-((2-(phenylsulfanyl)ethyl)amino)phenyl)sulfonyl)benzenecarboximidamide;

4-(4-(1,1'-biphenyl-2-ylmethyl)-4-methoxy-1-piperidinyl)-N-((4-((1,1-dimethyl-2-(phenylsulfanyl)ethyl)amino)-3-nitrophenyl)sulfonyl)benzenecarboximidamide;

4-(4-(1,1'-biphenyl-2-ylmethyl)-4-methoxy-1-piperidinyl)-N-((4-(((1R)-3-(4-morpholinyl)-1-((phenylsulfanyl)methyl)propyl)amino)-3-nitrophenyl)sulfonyl)benzenecarboximidamide;

4-(4-(1,1'-biphenyl-2-ylmethylene)-1-piperidinyl)-N'-((3-nitro-4-((2-(phenylsulfanyl)ethyl)amino)phenyl)sulfonyl)benzenecarboximidamide;

4-(4-(1,1'-biphenyl-2-ylmethylene)-1-piperidinyl)-N'-((4-((1,1-dimethyl-2-(phenylsulfanyl)ethyl)amino)-3-nitrophenyl)sulfonyl)benzenecarboximidamide;

4-(4-(1,1'-biphenyl-2-ylmethylene)-1-piperidinyl)-N'-((4-(((1R)-3-(4-morpholinyl)-1-((phenylsulfanyl)methyl)propyl)amino)-3-nitrophenyl)sulfonyl)benzenecarboximidamide;

N'-((3-nitro-4-((2-(phenylsulfanyl)ethyl)amino)phenyl)sulfonyl)-4-(4-(2-(trifluoromethyl)benzylidene)-1-piperidinyl)benzenecarboximidamide;

N'-((4-((1,1-dimethyl-2-(phenylsulfanyl)ethyl)amino)-3-nitrophenyl)sulfonyl)-4-(4-(2-(trifluoromethyl)benzylidene)-1-piperidinyl)benzenecarboximidamide; and N'-((4-(((1R)-3-(4-morpholinyl)-1-((phenylsulfanyl)methyl)propyl)amino)-3-nitrophenyl)sulfonyl)-4-(4-(2-(trifluoromethyl,)benzylidene)-1-piperidinyl)benzenecarboximidamide.

4. A pharmaceutical composition comprising a compound of claim 1 or a therapeutically acceptable salt thereof, in combination with a therapeutically acceptable carrier.

\* \* \* \* \*